(12) United States Patent
Rigo

(10) Patent No.: US 10,138,482 B2
(45) Date of Patent: Nov. 27, 2018

(54) COMPOSITIONS FOR MODULATING C9ORF72 EXPRESSION

(71) Applicant: Ionis Pharmaceuticals, Inc., Carlsbad, CA (US)

(72) Inventor: Frank Rigo, Carlsbd, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/404,979

(22) Filed: Jan. 12, 2017

(65) Prior Publication Data

US 2017/0349897 A1 Dec. 7, 2017

Related U.S. Application Data

(63) Continuation of application No. 15/130,818, filed on Apr. 15, 2016, now Pat. No. 9,605,263.

(60) Provisional application No. 62/239,400, filed on Oct. 9, 2015, provisional application No. 62/232,941, filed on Sep. 25, 2015, provisional application No. 62/148,691, filed on Apr. 16, 2015.

(51) Int. Cl.
| | | |
|---|---|---|
| *C07H 21/04* | (2006.01) | |
| *C07H 21/02* | (2006.01) | |
| *C12N 15/113* | (2010.01) | |

(52) U.S. Cl.
CPC ........ *C12N 15/113* (2013.01); *C12N 2310/11* (2013.01); *C12N 2310/315* (2013.01); *C12N 2310/322* (2013.01); *C12N 2310/3231* (2013.01); *C12N 2310/3341* (2013.01); *C12N 2310/341* (2013.01); *C12N 2310/346* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 9,963,699 B2 | 5/2018 | Bennett et al. | |
| 2004/0038274 A1 | 2/2004 | Cook et al. | |
| 2010/0216864 A1 | 8/2010 | Straarup et al. | |
| 2013/0035366 A1* | 2/2013 | Swayze .............. | C12N 15/1131 514/44 A |
| 2016/0251655 A1* | 9/2016 | Freier ................ | G01N 33/6896 514/44 A |

FOREIGN PATENT DOCUMENTS

| | | |
|---|---|---|
| WO | WO 1996/014329 | 5/1996 |
| WO | WO 2005/113016 | 12/2005 |
| WO | WO 2005/121368 | 12/2005 |
| WO | WO 2007/089584 | 8/2007 |
| WO | WO 2007/131237 | 11/2007 |
| WO | WO 2008/076324 | 6/2008 |
| WO | WO 2009/007855 | 1/2009 |
| WO | WO 2012/005898 | 1/2012 |
| WO | WO 2012/012443 | 1/2012 |
| WO | WO 2012/087983 | 6/2012 |
| WO | WO 2012/135736 | 10/2012 |
| WO | WO 2013/036833 | 3/2013 |
| WO | WO-2015054676 A2 * | 4/2015 ......... G01N 33/6896 |
| WO | WO 2017/079291 | 5/2017 |
| WO | WO 2017/180835 | 10/2017 |

OTHER PUBLICATIONS

Fernandes et al., "Oligonucleotide-Based Therapy for FTD/ALS Caused by the C9orf72 Repeat Expansion: A Perspective" Journal of Nucleic Acids (2013) :1-11.
Gendron et al., "Poly(GP) proteins are a useful pharmacodynamic marker for C9ORF72-associated amyotrophic lateral sclerosis" Sci Tran Med (2017) 9(383):1-12.
Lee et al., "Antisense Therapy in Neurology" Journal of Personalized Medicine (2013) 3(3): 144-176.
Sha et al., "Treatment implications of C9ORF72" Alzheimers Res Ther (2012) 4(6): 46.
Thomsen, "Dramatically improved RNA in 1-15 situ hybridization signals using LNA-modified probes" RNA (2005) 11(11): 1745-1748.
Ash et al., "Unconventional Translation of C9ORF72 GGGGCC Expansion Generates Insoluble Ploypeptides Specific to c9FTD/ALS" Neuron (2013) 77(4): 639-646.
Extended European Search Report for application No. 14852924.1 dated Jun. 20, 2017.
International Search Report for application No. PCT/US17/27355 dated Jul. 26, 2017.
Mahoney et al., "Frontotemporal dementia with the C9ORF72 hexanucleotide repeat expansion: clinical, neuroanatomical and neuropathological features" Brain (2012) 135: 736-750.
GenBank: Accession No. NT_008413, Jul. 24, 2012, 5 pages.
International Search Report for Application No. PCT/US2016/060106, dated Feb. 1, 2017, 10 pages.
Bennett et al., "Antisense oligonucleotides as a tool for gene functionalization and target validation," Biochimica et Biophysica Acta (1999) 1489: 19-30.
Jeong et al., "Rapid Identification of Monospecific Monoclonal Antibodies Using a Human Proteome Microarray." Mol. Cell. Proteomics (2012) 11(6): O111.016253-1 to O111.016253-10.
Watts et al., "Silencing disease genes in the laboratory and the clinic" J Pathol (2012) 226(2): 365-379.

\* cited by examiner

*Primary Examiner* — Richard A Schnizer
(74) *Attorney, Agent, or Firm* — McNeill Baur PLLC

(57) ABSTRACT

Disclosed herein are compositions and methods for reducing expression of C9ORF72 mRNA and protein in an animal. Such methods are useful to treat, prevent, ameliorate, or slow progression of neurodegenerative diseases in an individual in need thereof.

20 Claims, No Drawings
Specification includes a Sequence Listing.

US 10,138,482 B2

COMPOSITIONS FOR MODULATING C9ORF72 EXPRESSION

SEQUENCE LISTING

The present application is being filed along with a Sequence Listing in electronic format. The Sequence Listing is provided as a file entitled BIOL0269USC1SEQ_ST25.txt created Jan. 12, 2017, which is 104 Kb in size. The information in the electronic format of the sequence listing is incorporated herein by reference in its entirety.

FIELD

Provided are compositions and methods for modulating expression of C9ORF72 mRNA and protein in cells and animals. Such compositions and methods are useful to treat, prevent, ameliorate, or slow progression of neurodegenerative diseases, including amyotrophic lateral sclerosis (ALS), frontotemporal dementia (FTD), corticobasal degeneration syndrome (CBD), atypical Parkinsonian syndrome, and olivopontocerebellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). The mutation in the C9ORF72 gene is the most common genetic cause of ALS and FTD. The ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

A founder haplotype, covering the C9ORF72 gene, is present in the majority of cases linked to this region.

There are currently no effective therapies to treat such neurodegenerative diseases. Therefore, it is an object to provide compositions and methods for the treatment of such neurodegenerative diseases.

SUMMARY

Certain embodiments provide methods, compounds, and compositions for inhibiting expression of C9ORF72 mRNA and protein in cells, tissues, and animals. Certain embodiments provide methods, compounds, and compositions for reducing C9ORF72 mRNA and protein levels in cells, tissues, and animals. Certain embodiments provide antisense compounds targeted to a C9ORF72 nucleic acid. In certain embodiments, the antisense compounds are modified oligonucleotides. In certain embodiments, the modified oligonucleotides are single-stranded.

In certain embodiments, C9ORF72 associated Repeat Associated Non-ATG Translation (RAN translation) products are reduced. In certain embodiments, the C9ORF72 associated RAN translation products are poly-(glycine-proline), poly-(glycine-alanine), and poly-(glycine-arginine). In certain embodiments, certain C9ORF72 mRNA variants are preferentially reduced. In certain embodiments, the C9ORF72 mRNA variants preferentially reduced are variants processed from a pre-mRNA containing intron 1. In certain embodiments, intron 1 contains a hexanucleotide repeat expansion. In certain embodiments, the C9ORF72 mRNA variant preferentially reduced is a C9ORF72 pathogenic associated mRNA variant. In certain embodiments, the C9ORF72 pathogenic associated mRNA variant is NM_001256054.1 (SEQ ID NO: 1). In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 30 GGGGCC repeats, more than 30 GGGGCC repeats, more than 100 GGGGCC repeats, more than 500 GGGGCC repeats, or more than 1000 GGGGCC repeats. In certain embodiments, the hexanucleotide repeat expansion is associated with nuclear foci. In certain embodiments, C9ORF72 associated RAN translation products are associated with nuclear foci. In certain embodiments, the C9ORF72 associated RAN translation products are are poly-(glycine-proline), poly-(glycine-alanine), and poly-(glycine-arginine). In certain embodiments, the compositions and methods described herein are useful for reducing C9ORF72 mRNA levels, C9ORF72 protein levels, C9ORF72 RAN translation products, and nuclear foci. In certain embodiments, the compositions and methods described herein are useful for selectively reducing C9ORF72 pathogenic associated mRNA variants. Such reduction can occur in a time-dependent manner or in a dose-dependent manner.

Also provided are methods useful for preventing, treating, ameliorating, and slowing progression of diseases associated with C9ORF72. In certain embodiments, such C9ORF72 associated diseases are neurodegenerative diseases. In certain embodiments, the neurodegenerative disease is amyotrophic lateral sclerosis (ALS), frontotemporal dementia (FTD), corticobasal degeneration syndrome (CBD), atypical Parkinsonian syndrome, and olivopontocerebellar degeneration (OPCD).

Such diseases can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 antisense compound to an individual in need thereof. In certain embodiments, the antisense compound is a single-stranded modified oligonucleotide. In certain embodiments, the single-stranded modified oligonucleotide is complementary to a C9ORF72 nucleic acid.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

Compounds of the invention include variations of the disclosed compounds in which one or more hydrogen, carbon, nitrogen, oxygen, or sulfur atoms is replaced with a stable isotope of the same element.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxy-ethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a MOE modified sugar moiety.

"2'-substituted nucleoside" means a nucleoside comprising a substituent at the 2'-position of the furanose ring other than H or OH. In certain embodiments, 2'-substituted nucleosides include nucleosides with bicyclic sugar modifications.

"5-methylcytosine" means a cytosine modified with a methyl group attached to the 5' position. A 5-methylcytosine is a modified nucleobase.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 antisense transcript" means transcripts produced from the non-coding strand (also antisense strand and template strand) of the C9ORF72 gene. The C9ORF72 antisense transcript differs from the canonically transcribed "C9ORF72 sense transcript", which is produced from the coding strand (also sense strand) of the C9ORF72 gene. In certain embodiments, a C9ORF72 antisense transcript is SEQ ID NO: 18.

"C9ORF72 antisense transcript specific inhibitor" refers to any agent capable of specifically inhibiting the expression of C9ORF72 antisense transcript and/or its expression products at the molecular level. As used herein, "specific" means reducing or inhibiting expression of C9ORF72 antisense transcript without reducing non-target transcript to an appreciable degree (e.g., a C9ORF72 antisense transcript specific inhibitor reduces expression of C9ORF72 antisense transcript, but does not reduce expression of C9ORF72 sense transcript to an appreciable degree). C9ORF72 specific antisense transcript inhibitors include antisense compounds, siRNAs, aptamers, antibodies, peptides, small molecules, and other agents capable of inhibiting the expression of C9ORF72 antisense transcript and/or its expression products, such as C9ORF72 antisense transcript associated RAN translation products.

"C9ORF72 associated disease" means any disease associated with any C9ORF72 nucleic acid or expression product thereof. Such diseases may include a neurodegenerative disease. Such neurodegenerative diseases may include ALS and FTD. In certain embodiments, the C9ORF72 associated disease is caused by (or is associated with) a hexanucleotide repeat expansion. In certain embodiments, the hexanucleotide repeat expansion may comprise GGGGCC, GGGGGG, GGGGGC, or GGGGCG repeated at least 30 times, more than 30 times, more than 100 times, more than 500 times, or more than 1000 times.

"C9ORF72 associated RAN translation products" means aberrant peptide or di-peptide polymers translated through RAN translation (i.e., repeat-associated, and non-ATG-dependent translation). In certain embodiments, the C9ORF72 associated RAN translation products are any of poly-(glycine-proline), poly-(glycine-alanine), and poly-(glycine-arginine).

"C9ORF72 nucleic acid" means any nucleic acid encoding C9ORF72. For example, in certain embodiments, a C9ORF72 nucleic acid includes a DNA sequence encoding C9ORF72, an RNA sequence transcribed from DNA encoding C9ORF72 including genomic DNA comprising introns and exons (i.e., pre-mRNA), and an mRNA sequence encoding C9ORF72. "C9ORF72 mRNA" means an mRNA encoding a C9ORF72 protein.

"C9ORF72 pathogenic associated mRNA variant" means the C9ORF72 mRNA variant processed from a C9ORF72 pre-mRNA variant containing the hexanucleotide repeat. A C9ORF72 pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). In certain embodiments, the level of a C9ORF72 pathogenic associated mRNA variant is measured to determine the level of a C9ORF72 pre-mRNA containing the hexanucleotide repeat in a sample.

"C9ORF72 specific inhibitor" refers to any agent capable of specifically inhibiting the expression of C9ORF72 mRNA and/or C9ORF72 protein at the molecular level. For example, C9ORF72 specific inhibitors include nucleic acids (including antisense compounds), siRNAs, aptamers, antibodies, peptides, small molecules, and other agents capable of inhibiting the expression of C9ORF72 mRNA and/or C9ORF72 protein. Similarly, in certain embodiments, C9ORF72 specific inhibitors may affect other molecular processes in an animal.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH($CH_3$)—O-2'.

"Constrained ethyl nucleoside" (also cEt nucleoside) means a nucleoside comprising a bicyclic sugar moiety comprising a 4'-CH($CH_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Focus" or "foci" means a nuclear or cytoplasmic body comprising a C9ORF72 transcript.

In certain embodiments, a focus comprises at least one C9ORF72 transcript. In certain embodiments, C9ORF72 foci comprise transcripts comprising any of the following hexanucleotide repeats: GGGGCC, GGGGGG, GGGGGC, and/or GGGGCG.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Hexanucleotide repeat expansion" means a series of six bases (for example, GGGGCC, GGGGGG, GGGGCG, or GGGGGC) repeated at least twice. In certain embodiments, the hexanucleotide repeat expansion may be located in intron 1 of a C9ORF72 nucleic acid. In certain embodiments, a pathogenic hexanucleotide repeat expansion includes at least 30, more than 30, more than 100, more than 500, or more than 1000 repeats of GGGGCC, GGGGGG, GGGGCG, or GGGGGC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 23 or fewer repeats of GGGGCC, GGGGGG, GGGGCG, or GGGGGC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting C9ORF72" means reducing the level or expression of a C9ORF72 mRNA and/or protein. In certain embodiments, C9ORF72 mRNA and/or protein levels are inhibited in the presence of an antisense compound targeting C9ORF72, including an antisense oligonucleotide targeting C9ORF72, as compared to expression of C9ORF72 mRNA and/or protein levels in the absence of a C9ORF72 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

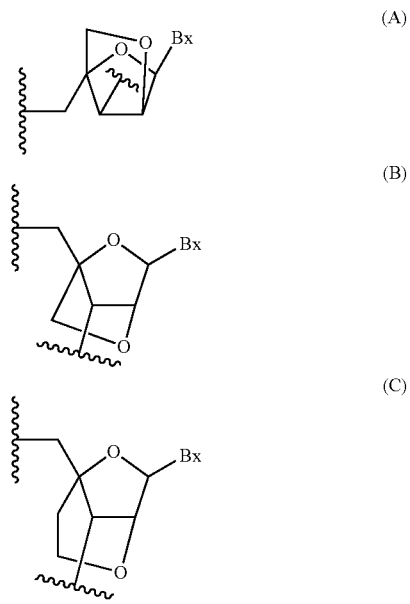

-continued

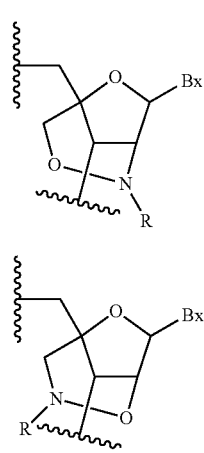

As used herein, LNA compounds include, but are not limited to, compounds having at least one bridge between the 4' and the 2' position of the sugar wherein each of the bridges independently comprises 1 or from 2 to 4 linked groups independently selected from —[C($R_1$)($R_2$)]$_n$—, —C($R_1$)=C($R_2$)—, —C($R_1$)=N—, —C(=N$R_1$)—, —C(=O)—, —C(=S)—, —O—, —Si($R_1$)$_2$—, —S(=O)$_x$— and —N($R_1$)—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, O$J_1$, N$J_1$$J_2$, S$J_1$, $N_3$, COO$J_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: —[C($R_1$)($R_2$)]$_n$—, —[C($R_1$)($R_2$)]$_n$—O—, —C($R_1$$R_2$)—N($R_1$)—O— or —C($R_1$$R_2$)—O—N($R_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N($R_1$)-2' and 4'-CH$_2$—N($R_1$)—O-2'-bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleoside in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to C9ORF72 is a pharmaceutical agent.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form within the body or cells thereof by the action of endogenous enzymes or other chemicals or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand. A "single-stranded modified oligonucleotide" means a modified oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" means administering a composition to effect an alteration or improvement of a disease or condition.

"Unmodified nucleobases" means the purine bases adenine (A) and guanine (G), and the pyrimidine bases (T), cytosine (C), and uracil (U).

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide compositions and methods for reducing total C9ORF72 mRNA and protein expression.

Certain embodiments provide compositions and methods for reducing C9ORF72 pathogenic associated mRNA variants.

Certain embodiments provide methods for the treatment, prevention, amelioration, or slowing progression of diseases associated with C9ORF72 in an individual in need thereof. Also contemplated are methods for the preparation of a medicament for the treatment, prevention, or amelioration of a disease associated with C9ORF72. C9ORF72 associated diseases include neurodegenerative diseases. In certain embodiments, the neurodegenerative disease may be ALS or FTD. In certain embodiments, the neurodegenerative disease may be familial or sporadic.

The present disclosure provided the following non-limiting numbered embodiments:

Embodiment 1

A compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 22-55.

Embodiment 2

The compound of embodiment 1, wherein the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1 or SEQ ID NO: 2.

Embodiment 3

The compound of embodiments 1 and 2, wherein the modified oligonucleotide is a single-stranded modified oligonucleotide.

Embodiment 4

The compound of any of embodiments 1-3, wherein the modified oligonucleotide comprises at least one modified internucleoside linkage.

Embodiment 5

The compound of embodiment 4, wherein the at least one modified internucleoside linkage is a phosphorothioate internucleoside linkage.

Embodiment 6

The compound of embodiments 4 and 5, wherein the modified oligonucleotide comprises at least one phosphodiester linkage.

Embodiment 7

The compound of embodiment 5, wherein each modified internucleoside linkage is a phosphorothioate internucleoside linkage.

Embodiment 8

The compound of any of embodiments 1-7, wherein at least one nucleoside comprises a modified nucleobase.

Embodiment 9

The compound of embodiment 8, wherein the modified nucleobase is a 5-methylcytosine.

Embodiment 10

The compound of any of embodiments 1-9, wherein at least one nucleoside of the modified oligonucleotide comprises a modified sugar.

Embodiment 11

The compound of embodiment 10, wherein each nucleoside of the modified oligonucleotide comprises a modified sugar.

Embodiment 12

The compound of embodiments 10 or 11, wherein the at least one modified sugar is a bicyclic sugar.

Embodiment 13

The compound of embodiment 12, wherein the bicyclic sugar comprises a chemical bridge between the 4' and 2' positions of the sugar, wherein the chemical bridge is selected from: 4'-CH(R)—O-2' and 4'-(CH$_2$)$_2$—O-2', wherein R is independently H, C$_1$-C$_6$ alkyl, and C$_1$-C$_6$ alkoxy.

Embodiment 14

The compound of embodiment 13, wherein the chemical bridge is 4'-CH(R)—O-2' and wherein R is methyl.

Embodiment 15

The compound of embodiment 13, wherein the chemical bridge is 4'-CH(R)—O-2' and wherein R is H.

Embodiment 16

The compound of embodiment 13, wherein the chemical bridge is 4'-CH(R)—O-2' and wherein R is —CH$_2$—O—CH$_3$.

Embodiment 17

The compound of embodiments 10 or 11, wherein the at least one modified sugar comprises a 2'-O-methoxyethyl group.

Embodiment 18

The compound of any of embodiments 1-10 or 12-16, wherein the modified oligonucleotide is a gapmer.

Embodiment 19

The compound of embodiment 18, wherein the gapmer is any of a 3-8-7 MOE gapmer, a 3-10-7 MOE gapmer, a 4-8-6 MOE gapmer, a 4-10-6 MOE gapmer, a 6-10-4 MOE gapmer, a 6-8-4 MOE gapmer, a 7-8-3 MOE gapmer, or a 7-10-3 MOE gapmer.

Embodiment 20

The compound of claim 5, wherein the modified oligonucleotide comprises internucleoside linkages in any of the following patterns: sooosssssssssoooooss, sooossssssssss-soooss, soooooosssssssssoss, soooooosssssssssss, sooooossssssssoooss, sooossssssssoooss, sooooooSssssssss-soss, sooosssssssoooss, soooosssssssssoss, sosssssssss-sooooss, or sooooossssssssss, wherein,
s=a phosphorothioate linkage, and
o=a phosphodiester linkage.

Embodiment 19

A composition comprising the compound of any preceding embodiment or salt thereof and at least one of a pharmaceutically acceptable carrier or diluent.

Embodiment 20

The composition of embodiment 19, further comprising a C9ORF72 antisense transcript specific inhibitor.

Embodiment 21

The composition of embodiment 20, wherein the C9ORF72 antisense transcript specific inhibitor is an antisense compound.

Embodiment 22

The composition of embodiment 21, wherein the antisense compound is a modified oligonucleotide.

Embodiment 23

The composition of embodiment 22, wherein the modified oligonucleotide is single-stranded.

Embodiment 24

The composition of embodiments 22 or 23, wherein the modified oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

Embodiment 25

The composition of embodiment 24, wherein the C9ORF72 antisense transcript has the nucleobase sequence of SEQ ID NO: 18.

Embodiment 26

A method comprising administering to an animal the compound or composition of any preceding embodiment.

Embodiment 27

The method of embodiment 26, wherein the animal is a human.

Embodiment 28

The method of embodiments 26 and 27, wherein administering the compound prevents, treats, ameliorates, or slows progression of a C9ORF72 associated disease.

Embodiment 29

The method of embodiment 28, wherein the C9ORF72 associated disease is caused by a hexanucleotide repeat expansion.

Embodiment 30

The method of embodiment 28, wherein the C9ORF72 associated disease is amyotrophic lateral sclerosis (ALS), frontotemporal dementia (FTD), corticobasal degeneration syndrome (CBD), atypical Parkinsonian syndrome, and olivopontocerebellar degeneration (OPCD).

Embodiment 31

The method of embodiments 26-30, wherein the administering reduces nuclear foci.

Embodiment 32

The method of embodiments 26-31, wherein the administering reduces expression of C9ORF72 associated RAN translation products.

Embodiment 33

The method of embodiment 32, wherein the C9ORF72 associated RAN translation products are any of poly-(glycine-proline), poly-(glycine-alanine), and poly-(glycine-arginine).

Embodiment 34

Use of the compound or composition of any of embodiments 1-33 for the manufacture of a medicament for treating a neurodegenerative disorder.

Embodiment 35
A compound consisting of a modified oligonucleotide according to the following formula, or a salt thereof:
(SEQ ID NO: 33)
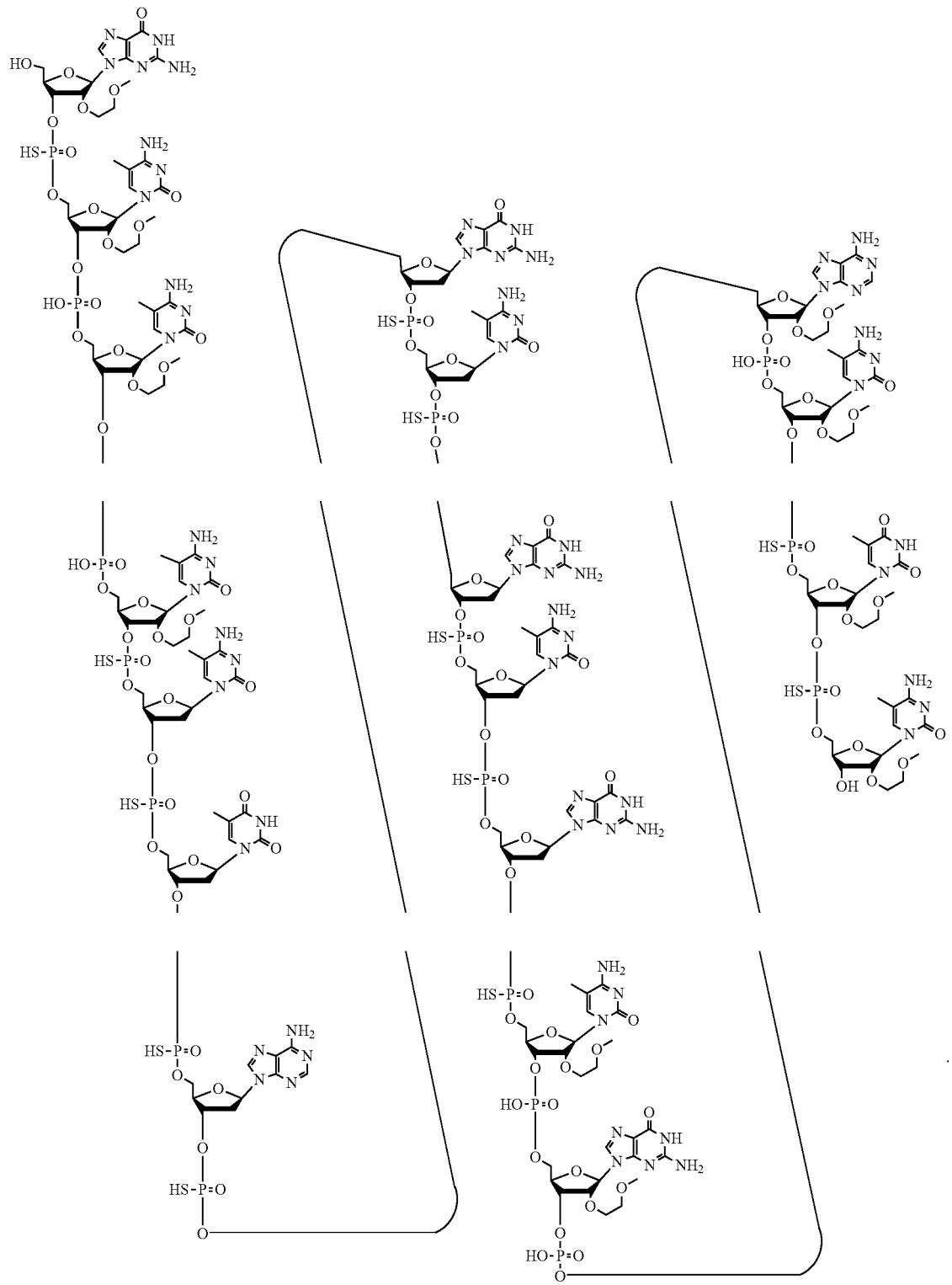

Embodiment 36
A composition consisting of the sodium salt of a modified oligonucleotide according to the following formula:
(SEQ ID NO: 33)
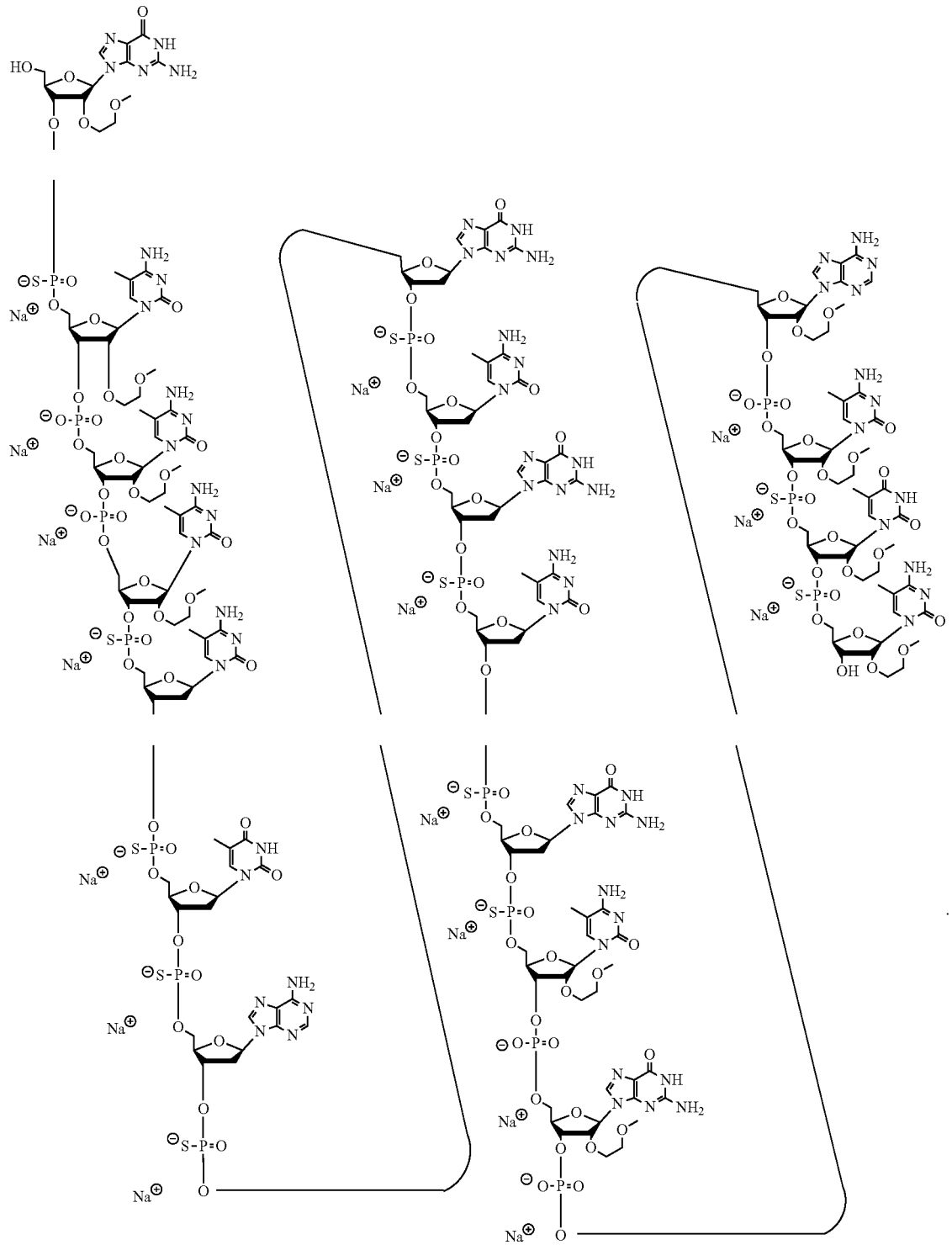

Embodiment 37
A compound consisting of a modified oligonucleotide according to the following formula, or a salt thereof:
(SEQ ID NO: 49)
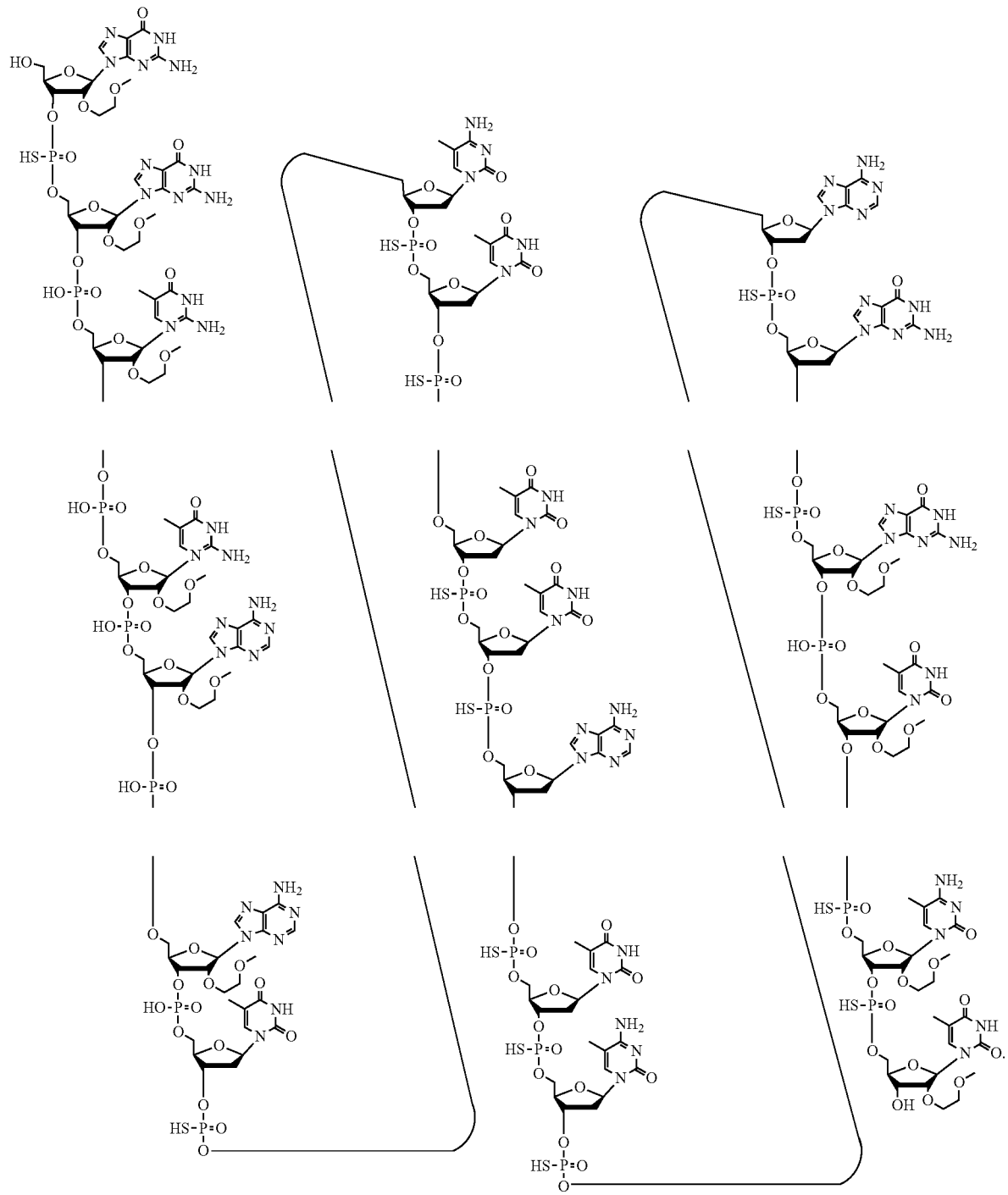

Embodiment 38
A composition consisting of the sodium salt of a modified oligonucleotide according to the following formula:
(SEQ ID NO: 49)
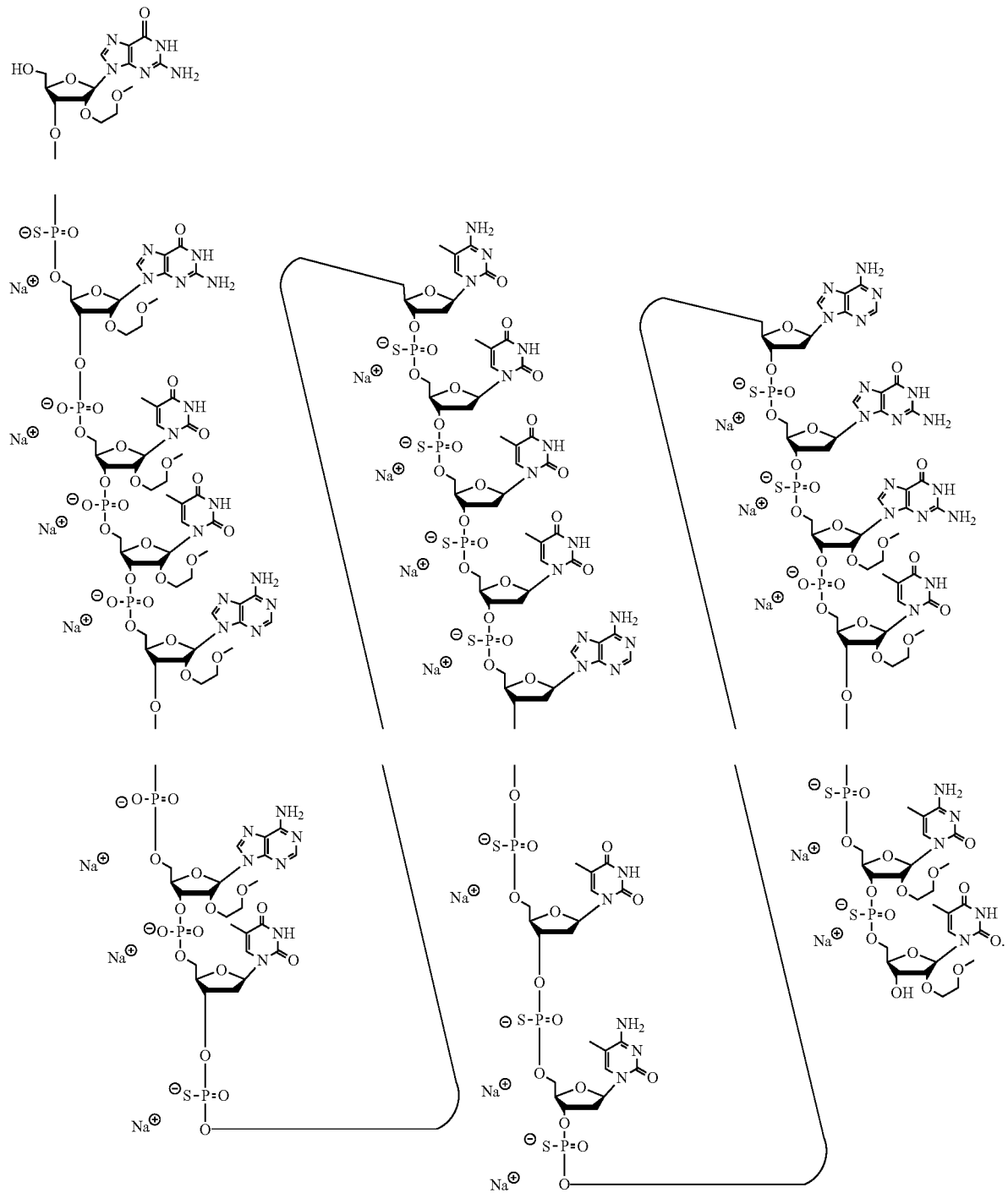

Embodiment 39
A compound consisting of a modified oligonucleotide according to the following formula, or a salt thereof:
(SEQ ID NO: 47)
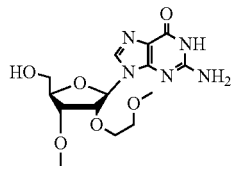
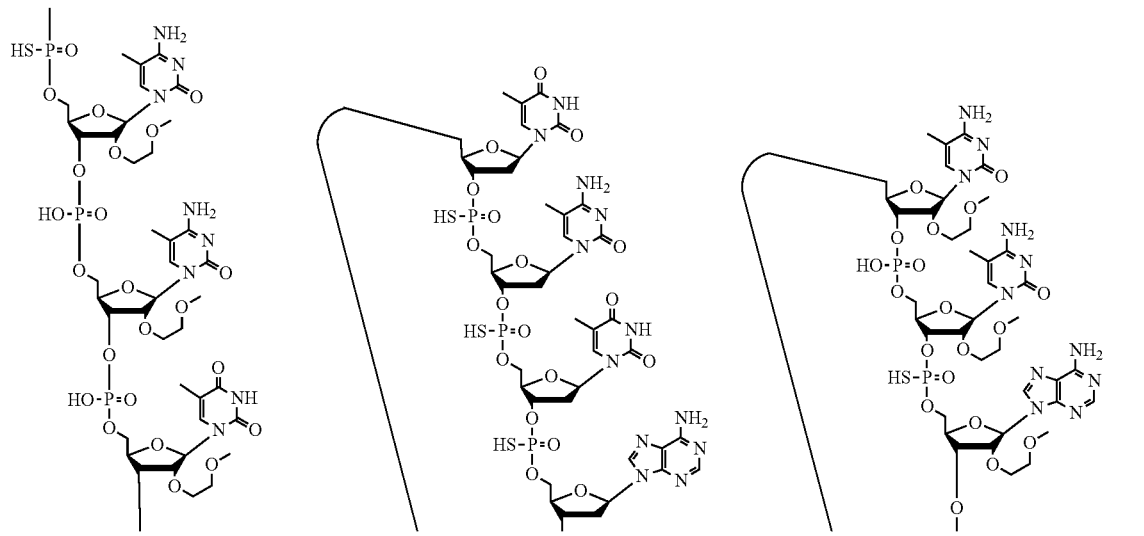
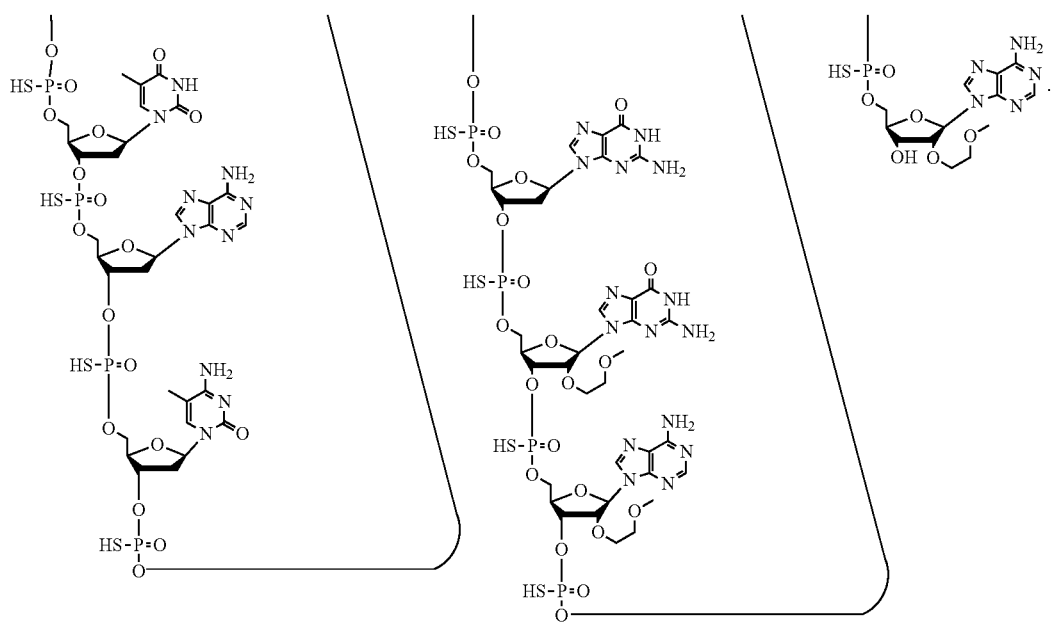

Embodiment 40
A composition consisting of the sodium salt of a modified oligonucleotide according to the following formula:
(SEQ ID NO: 47)
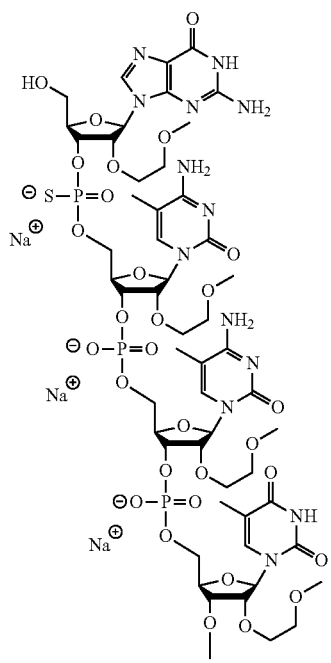
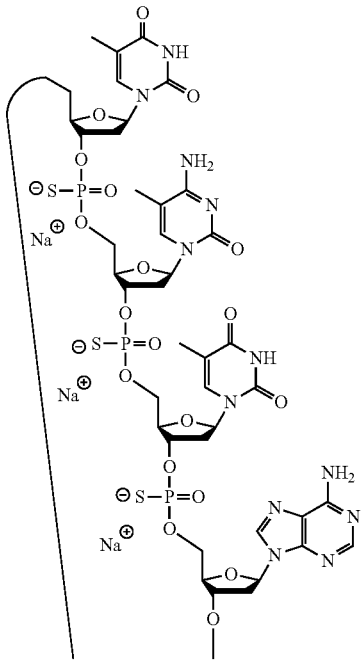
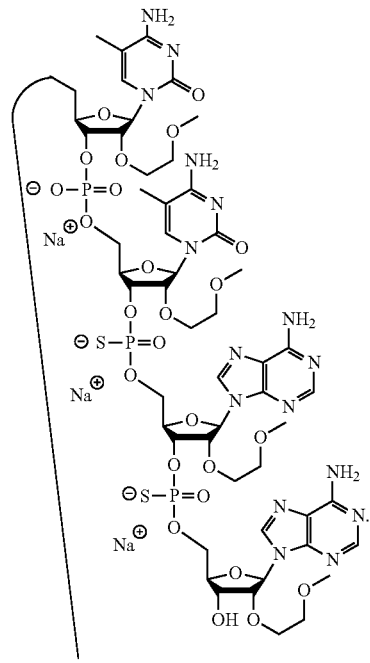
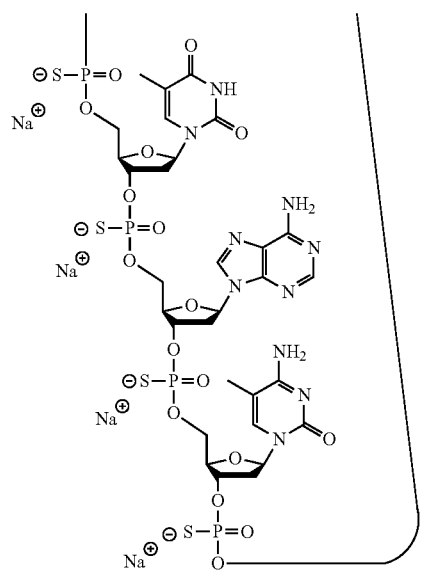
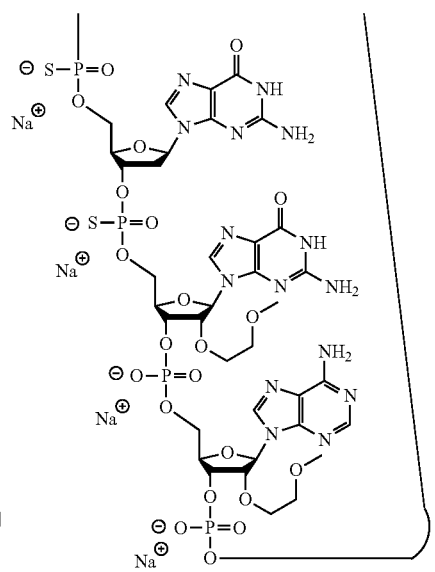

Embodiment 41
A compound consisting of a modified oligonucleotide according to the following formula, or a salt thereof:
(SEQ ID NO: 21)
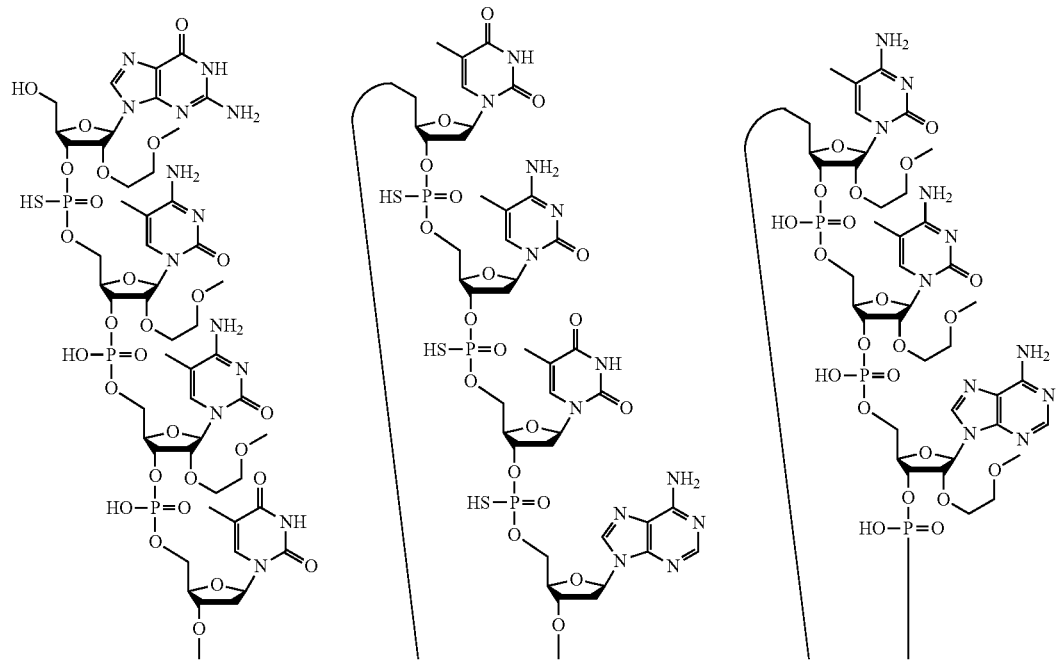
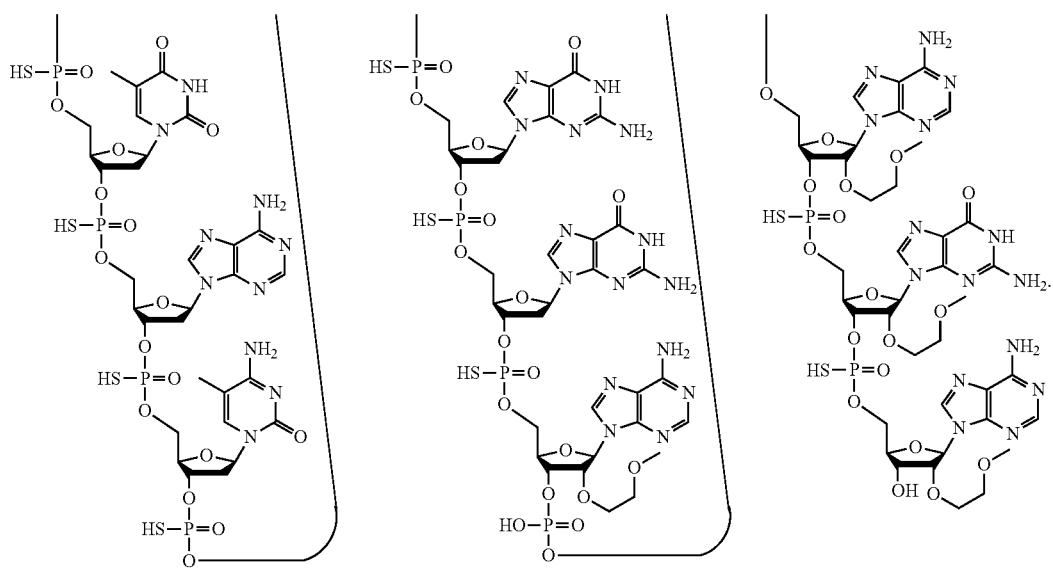

Embodiment 42

A composition consisting of the sodium salt of a modified oligonucleotide according to the following formula:

(SEQ ID NO: 21)

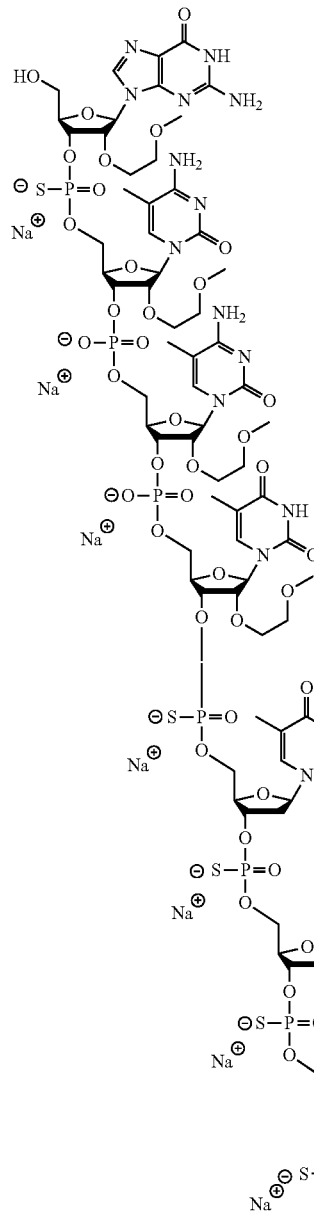

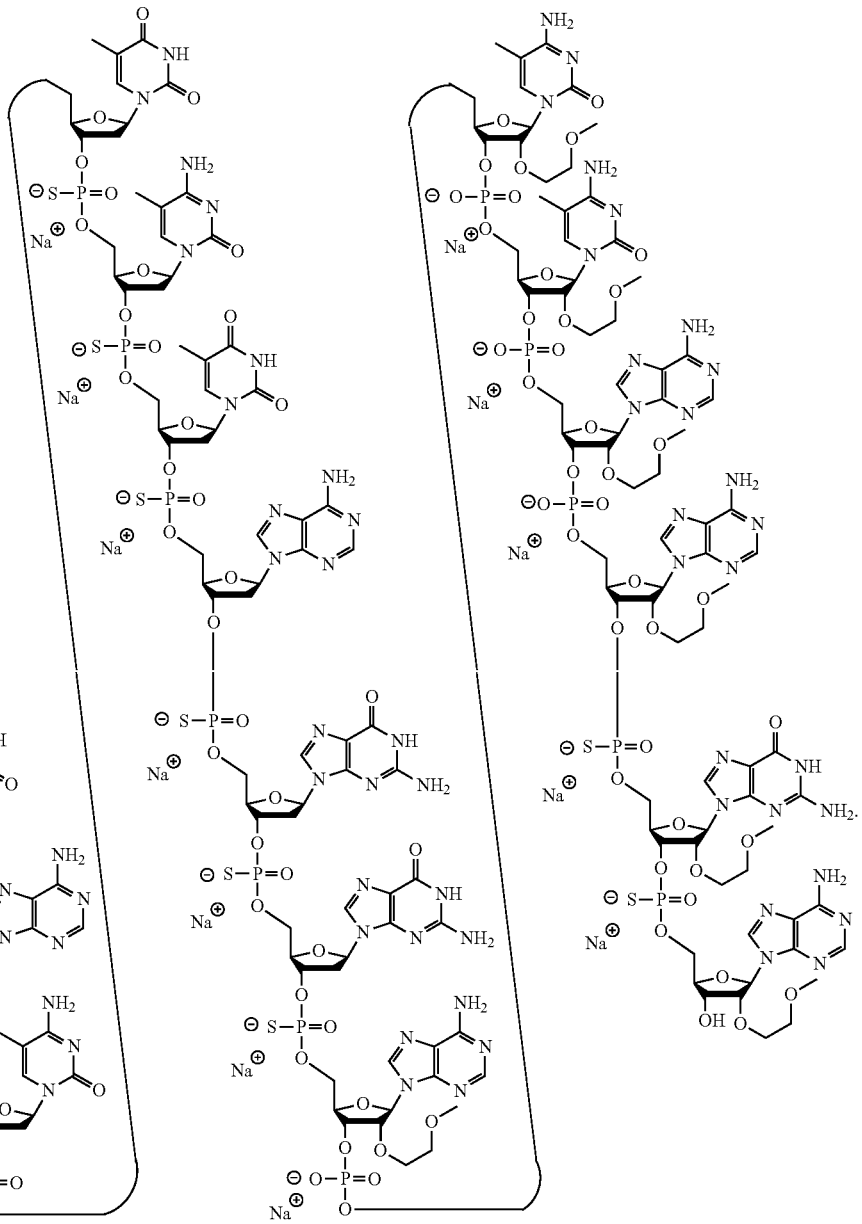

Embodiment 43

The compound or composition of any of embodiments 1-25 or 35-42, wherein the compound or composition is capable of reducing human C9ORF72 mRNA or protein expression in a mammal.

Embodiment 44

The compound or composition of any of embodiments 1-25 or 35-42, wherein the compound or composition is capable of ameliorating at least one symptom of amyotrophic lateral sclerosis (ALS), frontotemporal dementia (FTD), corticobasal degeneration syndrome (CBD), atypical Parkinsonian syndrome, or olivopontocerebellar degeneration (OPCD).

Embodiment 45

The compound or composition of embodiment 44, wherein the symptom of ALS is any of motor deficit, anxiety, and denervation.

Embodiment 46

The compound or composition of any of embodiments 1-25 or 35-42, wherein the compound or composition is capable of delaying progression of disease.

Embodiment 47

The compound or composition of any of embodiments 1-25 or 35-42, wherein the compound or composition is capable of extending survival.

Embodiment 48

The compound or composition of any of embodiments 1-25 or 35-42, wherein the compound or composition is capable of reducing C9ORF72 associated RAN translation products.

Embodiment 49

The compound or composition of any of embodiments 1-25 or 35-42, wherein the compound or composition is capable of selectively reducing C9ORF72 pathogenic associated mRNA variants.

Embodiment 50

The compound or composition of any of embodiments 1-25 or 35-42, wherein the compound or composition is capable of reducing nuclear foci.

Embodiment 51

A compound consisting of a modified oligonucleotide according to the following formula, or a salt thereof:

(SEQ ID NO: 33)

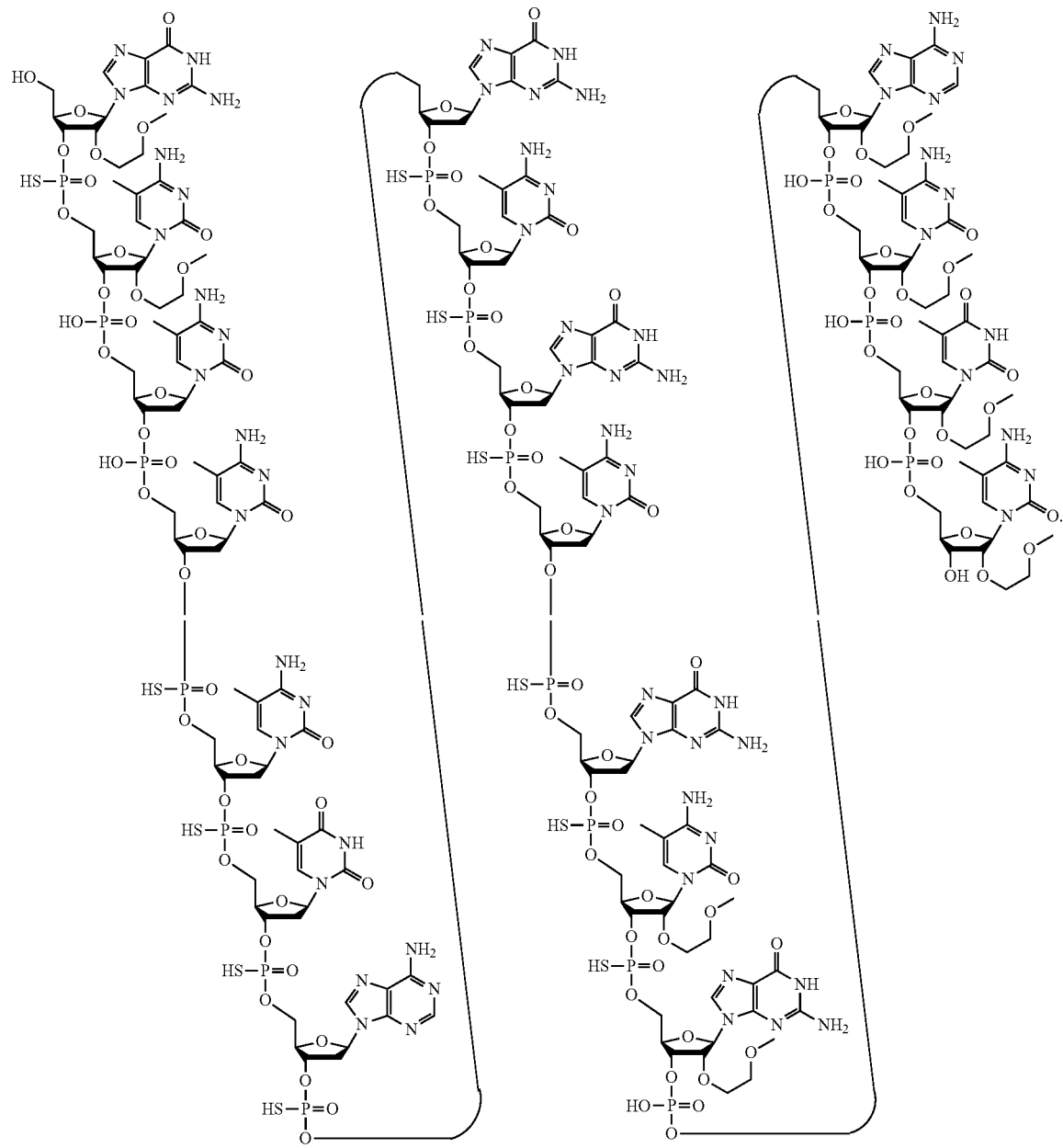

Embodiment 52

A method comprising administering to an animal the compound of embodiment 51.

Embodiment 53

The method of embodiment 52, wherein the animal is a human.

Embodiment 54

The method of embodiment 53, wherein the administering inhibits C9ORF72.

Embodiment 55

The method of embodiment 53, wherein the administering prevents, treats, ameliorates, or slows progression of a C9ORF72 associated disease.

Embodiment 56

The method of embodiment 55, wherein the C9ORF72 associated disease is caused by a hexanucleotide repeat expansion.

Embodiment 57

The method of embodiment 55, wherein the C9ORF72 associated disease is any of amyotrophic lateral sclerosis (ALS), frontotemporal dementia (FTD), corticobasal degeneration syndrome (CBD), atypical Parkinsonian syndrome, or olivopontocerebellar degeneration (OPCD).

Embodiment 58

The method of embodiment 53, wherein the administering reduces nuclear foci.

Embodiment 59

The method of embodiment 53, wherein the administering reduces expression of C9ORF72 associated RAN translation products.

Embodiment 60

The method of embodiment 59, wherein the C9ORF72 associated RAN translation products are any of poly-(glycine-proline), poly-(glycine-alanine), and poly-(glycine-arginine).

Embodiment 61

A composition consisting of the sodium salt of a modified oligonucleotide according to the following formula:

(SEQ ID NO: 33)

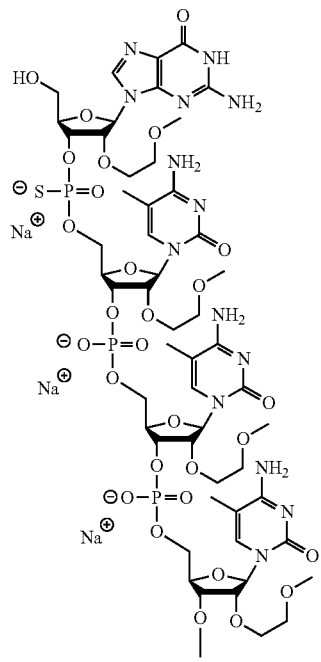
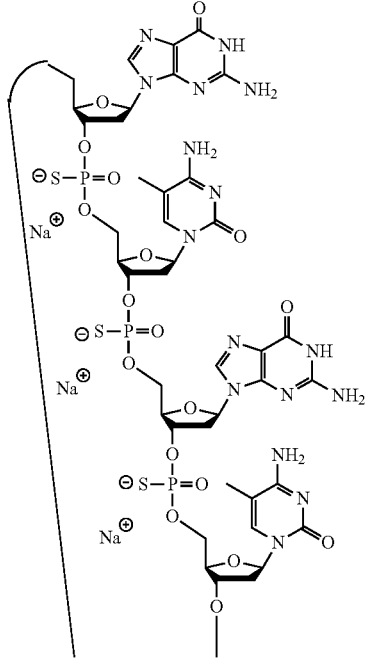
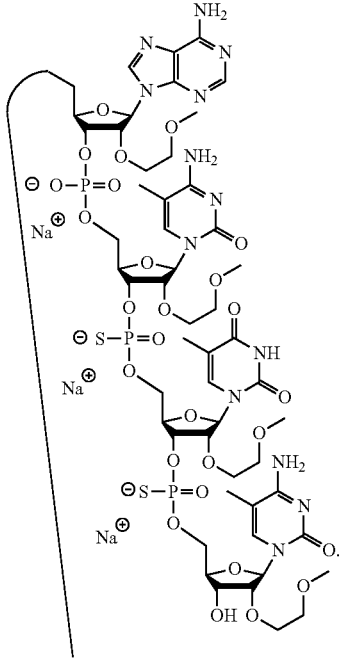

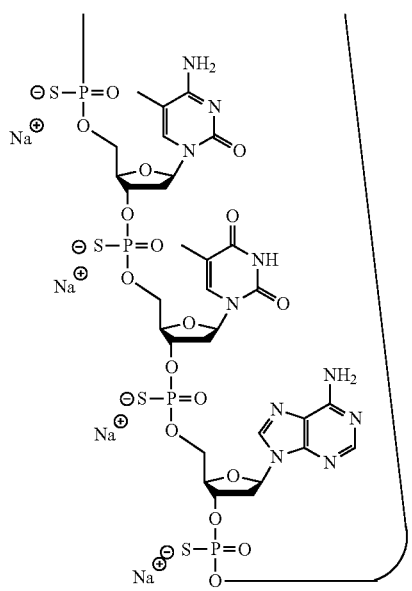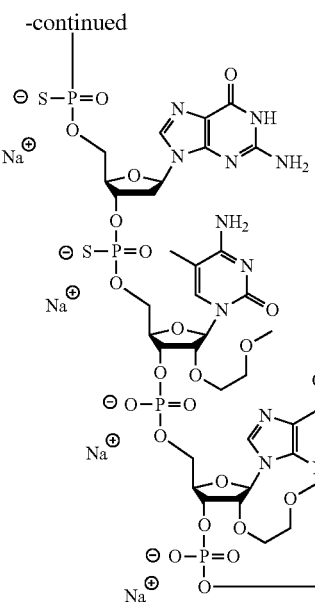

Embodiment 64

The method of embodiment 63, wherein the administering inhibits C9ORF72.

Embodiment 65

The method of embodiment 62, wherein the administering prevents, treats, ameliorates, or slows progression of a C9ORF72 associated disease.

Embodiment 66

The method of embodiment 65, wherein the C9ORF72 associated disease is caused by a hexanucleotide repeat expansion.

Embodiment 67

The method of embodiment 65, wherein the C9ORF72 associated disease is any of amyotrophic lateral sclerosis (ALS), frontotemporal dementia (FTD), corticobasal degeneration syndrome (CBD), atypical Parkinsonian syndrome, or olivopontocerebellar degeneration (OPCD).

Embodiment 68

The method of embodiment 63, wherein the administering reduces nuclear foci.

Embodiment 69

The method of embodiment 63, wherein the administering reduces expression of C9ORF72 associated RAN translation products.

Embodiment 70

The method of embodiment 69, wherein the C9ORF72 associated RAN translation products are any of poly-(glycine-proline), poly-(glycine-alanine), and poly-(glycine-arginine).

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2 and 4'-CH$_2$—O—CH$_2$-2'). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X—Y or Y—Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a C9ORF72 nucleic acid possess a 5-10-5 gapmer motif.

In certain embodiments, antisense compounds targeted to a C9ORF72 nucleic acid possess a 5-8-5 gapmer motif.

In certain embodiments, antisense compounds targeted to a C9ORF72 nucleic acid possess sugar modifications in any of the following patterns: eeekkddddddddkkeee, eekkddddddddkkeee, ekddddddddekekeee, kekedddddddde-keke, and ekekdddddddddkekee; wherein,
    e=a 2'-O-methoxyethyl modified nucleoside
    d=a 2'-deoxynucleoside, and
    k=a cEt nucleoside.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-(CH$_2$)$_n$—O-2' bridge, wherein n is 1 or 2; and 4'-CH$_2$—O—CH$_2$-2'. In certain embodiments, the bicyclic sugar is comprises a 4'-CH(CH$_3$)—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), the complement of GENBANK Accession No. NT_008413.18 truncated from nucleobase 27535000 to 27565000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10), and GENBANK Accession No. NW_001101662.1 truncated from nucleosides 8522000 to U.S. Pat. No. 8,552,000 (incorporated herein as SEQ ID NO: 11).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage. In certain embodiments, the antisense compounds targeted to a C9ORF72 nucleic acid comprise at least one phosphodiester linkage and at least one phosphorothioate linkage.

In certain embodiments, antisense compounds targeted to a C9ORF72 nucleic acid possess internucleoside linkages in any of the following patterns: soooosssssssssssooss, sooossssssssssooss, soossssssssssooss, and sosssssssssooooss; wherein,
s=a phosphorothioate linkage, and
o=a phosphodiester linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_{20}CH_3$ substituent groups. The substituent at the 2' position can also be selected from allyl, amino, azido, thio, O-allyl, O—$C_1$-$C_{10}$ alkyl, $OCF_3$, $OCH_2F$, O($CH_2$)$_2SCH_3$, O($CH_2$)$_2$—O—N($R_m$)($R_n$), O—$CH_2$—C(=O)—N($R_m$)($R_n$), and O—$CH_2$—C(=O)—N($R_1$)—($CH_2$)$_2$—N($R_m$)($R_n$), where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-($CH_2$)—O-2' (LNA); 4'-($CH_2$)—S-2'; 4'-($CH_2$)$_2$—O-2' (ENA); 4'-CH($CH_3$)—O-2' and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see PCT/US2008/068922 published as WO/2009/006478, published Jan. 8, 2009); 4'-$CH_2$—N($OCH_3$)-2' (and analogs thereof see PCT/US2008/064591 published as WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2'

(see Chattopadhyaya et al., J. Org. Chem., 2009, 74, 118-134); and 4'-CH$_2$—C(=CH$_2$)-2' (and analogs thereof see PCT/US2008/066154 published as WO 2008/154401, published on Dec. 8, 2008).

Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A, 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiment, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiment, bicyclic nucleosides have the formula:

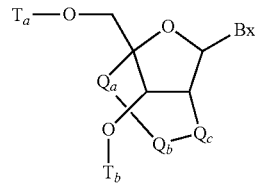

wherein:

Bx is a heterocyclic base moiety;

-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;

R$_c$ is C$_1$-C$_{12}$ alkyl or an amino protecting group; and

T$_a$ and T$_b$ are each, independently, H, a hydroxyl protecting group, a conjugate group, a reactive phosphorus group, a phosphorus moiety or a covalent attachment to a support medium.

In certain embodiments, bicyclic nucleosides have the formula:

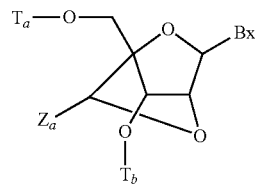

wherein:

Bx is a heterocyclic base moiety;

T$_a$ and T$_b$ are each, independently, H, a hydroxyl protecting group, a conjugate group, a reactive phosphorus group, a phosphorus moiety or a covalent attachment to a support medium;

Z$_a$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, OJ$_c$, NJ$_c$J$_d$, SJ$_c$, N$_3$, OC(=X)J$_c$, and NJ$_e$C(=X)NJ$_c$J$_d$, wherein each J$_c$, J$_d$ and J$_e$ is, independently, H, C$_1$-C$_6$ alkyl, or substituted C$_1$-C$_6$ alkyl and X is O or NJ$_c$.

In certain embodiments, bicyclic nucleosides have the formula:

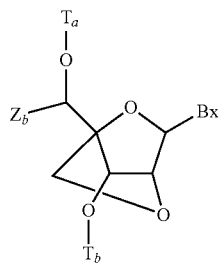

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

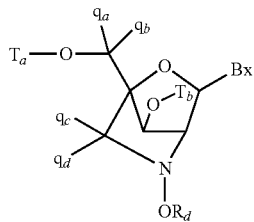

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

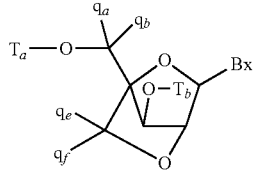

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-CH$_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-CH$_2$—O-2' and 4'-CH$_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

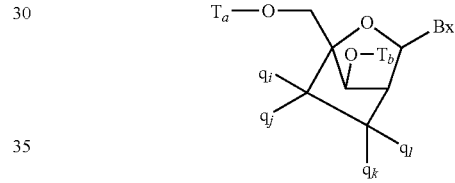

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, (F) methyl(methyleneoxy) (4'-CH(CH$_3$)—O-2') BNA (also referred to as constrained ethyl or cEt), (G)

methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

(A)
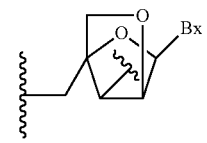

(B)
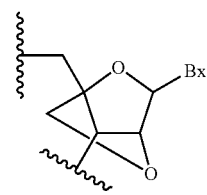

(C)
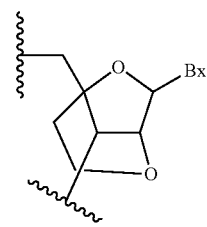

(D)
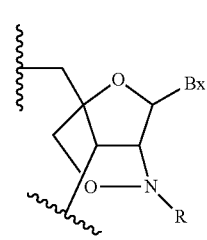

(E)
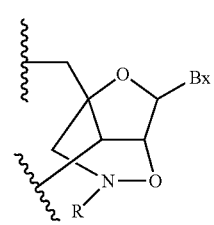

(F)
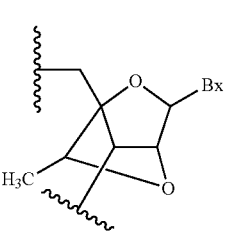

(G)
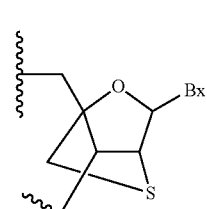

-continued (H)
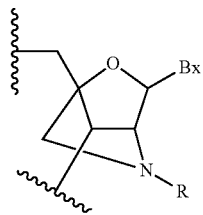

(I)
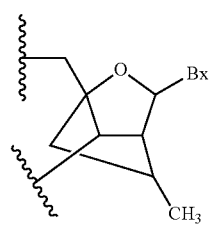

(J)
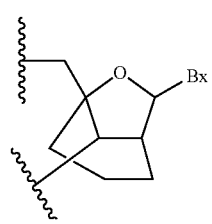

(K)
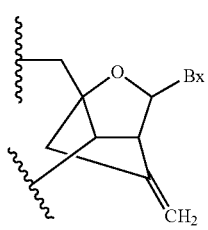

wherein Bx is the base moiety and R is, independently, H, a protecting group, C$_1$-C$_6$ alkyl or C$_1$-C$_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

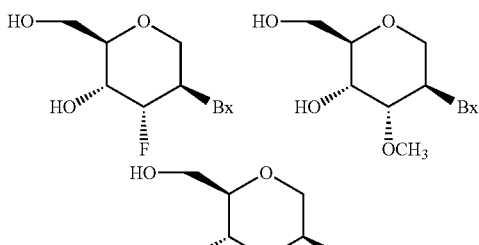

In certain embodiment, sugar surrogates are selected having the formula:

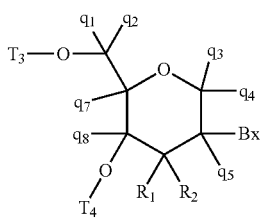

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

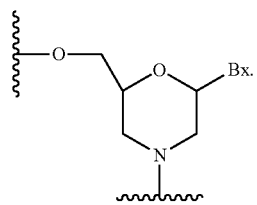

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

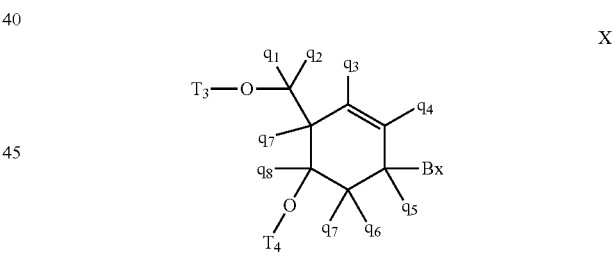

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O($CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$", "2'-O-methyl" or "2'-methoxy" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commerical vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline (PBS) or artificial cerebrospinal fluid (aCSF). Administration includes parenteral routes of administration, such as intraperitoneal, intravenous, and subcutaneous, as well as central routes of administration such as intracerebroventricular or intrathecal. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid in any stage of RNA processing. For example, described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72. In certain embodiments, the antisense oligonucleotides described herein selectively hybridize to certain variants of C9ORF72. In certain embodiments, the antisense oligonucleotides described herein selectively hybridize to variants of C9ORF72 containing a hexanucleotide repeat expansion. In certain embodiments, the antisense oligonucleotides described herein selectively hybridize to pre-mRNA variants containing the hexanucleotide repeat. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG.

In certain embodiments, the antisense oligonucleotides described herein inhibit expression of all variants of C9ORF72. In certain embodiments, the antisense oligonucleotides described herein inhibit expression of all variants of C9ORF72 equally. In certain embodiments, the antisense oligonucleotides described herein preferentially inhibit expression of one or more variants of C9ORF72. In certain embodiments, the antisense oligonucleotides described herein preferentially inhibit expression of variants of C9ORF72 containing a hexanucleotide repeat expansion. In certain embodiments, the antisense oligonucleotides described herein selectively inhibit expression of pre-mRNA variants containing the hexanucleotide repeat. In certain embodiments, the antisense oligonucleotides described herein selectively inhibit expression of C9ORF72 pathogenic associated mRNA variants. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG. In certain embodiments, the hexanucleotide repeat expansion forms nuclear foci. In certain embodiments, antisense oligonucleotides described herein are useful for reducing nuclear foci. Nuclear foci may be reduced in terms of percent of cells with foci as well as number of foci per cell.

Selective Inhibition of Certain Pathogenic Associated Variants

In certain examples herein, primer probe set RTS3905 detects an mRNA variant (e.g. NM_001256054.1) processed from a pre-mRNA variant containing the hexanucleotide repeat. The mRNA variant processed from a pre-mRNA variant containing the hexanucleotide repeat (i.e., the "C9ORF72 pathogenic associated mRNA variant"). A pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). Oligonucleotides were designed in this region to selectively target the pre-mRNA variant containing the hexanucleotide repeat. RTS3905 measures an mRNA product (i.e. the C9ORF72 pathogenic associated mRNA variant) of the pre-mRNA variant containing the hexanucleotide repeat and, therefore, measures the reduction of the pre-mRNA variant containing the hexanucleotide repeat.

C9ORF72 Features

Antisense oligonucleotides described herein may hybridize to any C9ORF72 variant at any state of processing within any element of the C9ORF72 gene. For example, antisense oligonucleotides described herein may hybridize to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 for the various C9ORF72 variants described below. Antisense oligonucleotides described herein may also target variants not characterized below and such variants are characterized in GENBANK. Moreover, antisense oligonucleotides described herein may also target elements other than exons and such elements are characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
|---|---|---|---|---|
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
|---|---|---|---|---|
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
|---|---|---|---|---|
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
|---|---|---|---|---|
| exon 1E | 1 | 35 | 1135 | 1169 |
| exon 2 | 36 | 524 | 7839 | 8326 |
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
|---|---|---|---|---|
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to C9ORF72 are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 specific inhibitor described herein include, but are not limited to, an additional C9ORF72 inhibitor.

In certain embodiments, pharmaceutical agents that may be co-administered with a C9ORF72 specific inhibitor described herein include, but are not limited to, a C9ORF72 antisense transcript specific inhibitor. In certain embodiments, the C9ORF72 antisense transcript specific inhibitor is an antisense compound. In certain embodiments, the antisense compound is a modified oligonucleotide. In certain embodiments, the modified oligonucleotide is single-stranded.

In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

Certain Comparator Compositions

In certain embodiments, compounds described herein are more tolerable than ISIS 576816, ISIS 576974, ISIS 577061, ISIS 577065, and/or ISIS 577083. ISIS 576816, ISIS 576974, ISIS 577061, ISIS 577065, and ISIS 577083 were selected as comparator compounds because they exhibited high levels of dose-dependent reduction of C9ORF72 mRNA in various studies described in WO2014/062691. Thus, ISIS 576816, ISIS 576974, ISIS 577061, ISIS 577065, and ISIS 577083 were deemed highly efficacious and potent compounds. Additionally, ISIS 577065, ISIS 577056, and ISIS 576816 described in WO2014/062691 are structurally similar as compounds described herein. For example, ISIS 577065 has a 16 nucleobase overlap with ISIS 801287; ISIS 577056 has a 16 nucleobase overlap with ISIS 806679; ISIS 576816 has an 18 nucleobase overlap with ISIS 802473 (18-mer); and ISIS 576816 has an 18 nucleobase overlap with ISIS 802459.

In certain embodiments, ISIS 576816, a 5-10-5 MOE gapmer, having a sequence of (from 5' to 3') GCCTTACTCTAGGACCAAGA (incorporated herein as SEQ ID NO: 21), wherein each internucleoside linkage is a phosphorothioate linkage, each cytosine is a 5-methylcytosine, and each of nucleosides 1-5 and 16-20 comprise a 2'-O-methoxyethyl group, which was previously described in WO2014/062691, incorporated herein by reference, is a comparator compound. ISIS 576816 achieved an average FOB score of 7.00 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 576816.

In certain embodiments, ISIS 576974, a 5-10-5 MOE gapmer, having a sequence of (from 5' to 3') GGGACACTACAAGGTAGTAT (incorporated herein as SEQ ID NO: 56), wherein each internucleoside linkage is a phosphorothioate linkage, each cytosine is a 5-methylcytosine, and each of nucleosides 1-5 and 16-20 comprise a 2'-O-methoxyethyl group, which was previously described in WO2014/062691, incorporated herein by reference, is a comparator compound. ISIS 576974 achieved an average FOB score of 5.67 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 576974.

In certain embodiments, ISIS 577061, a 5-10-5 MOE gapmer, having a sequence of (from 5' to 3') TACAGGCTGCGGTTGTTTCC (incorporated herein as SEQ ID NO: 57), wherein each internucleoside linkage is a phosphorothioate linkage, each cytosine is a 5-methylcytosine, and each of nucleosides 1-5 and 16-20 comprise a 2'-O-methoxyethyl group, which was previously described in WO2014/062691, incorporated herein by reference, is a comparator compound. ISIS 577061 achieved an average FOB score of 7.00 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 577061.

In certain embodiments, ISIS 577065, a 5-10-5 MOE gapmer, having a sequence of (from 5' to 3') CCCGGCCCCTAGCGCGCGAC (incorporated herein as SEQ ID NO: 58), wherein each internucleoside linkage is a phosphorothioate linkage, each cytosine is a 5-methylcytosine, and each of nucleosides 1-5 and 16-20 comprise a 2'-O-methoxyethyl group, which was previously described in WO2014/062691, incorporated herein by reference, is a comparator compound. ISIS 577065 achieved an average FOB score of 6.00 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 577065.

In certain embodiments, ISIS 577083, a 5-10-5 MOE gapmer, having a sequence of (from 5' to 3') GGTAACTTCAAACTCTTGGG (incorporated herein as SEQ ID NO: 59), wherein each internucleoside linkage is a phosphorothioate linkage, each cytosine is a 5-methylcytosine, and each of nucleosides 1-5 and 16-20 comprise a 2'-O-methoxyethyl group, which was previously described in WO2014/062691, incorporated herein by reference, is a comparator compound. ISIS 577083 achieved an average FOB score of 7.00 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 577083.

In certain embodiments, ISIS 577056, a 5-10-5 MOE gapmer, having a sequence of (from 5' to 3') AATCTTTATCAGGTCTTTTC (incorporated herein as SEQ ID NO: 60), wherein each internucleoside linkage is a phosphorothioate linkage, each cytosine is a 5-methylcytosine, and each of nucleosides 1-5 and 16-20 comprise a 2'-O-methoxyethyl group, which was previously described in WO2014/062691, incorporated herein by reference, is a comparator compound. ISIS 577056 achieved an average FOB score of 6.5 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 577056.

Certain Human Therapeutics

The human C9ORF72 antisense oligonucleotides described herein are human therapeutics. Various parameters of potency, efficacy, and/or tolerability are being examined. Such parameters include in vitro inhibition of total C9ORF72 RNA expression, in vitro inhibition of C9ORF72 pathogenic associated RNA variant expression, in vitro dose response (IC50), in vivo inhibition of total or pathogenic RNA and/or protein in a transgenic animal containing a human C9ORF72 transgene in relevant tissues (e.g., brain and/or spinal cord), tolerability in mouse, tolerability in rat, and/or tolerability in a primate. Tolerability markers that may be measured include blood and serum chemistry parameters, CSF chemistry parameters, body and organ weights, general observations and/or behavioral tests, and/or biochemical markers such as GFAP and/or AIF1. Acute or long term tolerability may be measured.

Certain Compositions

1. ISIS 801287

In certain embodiments, ISIS 801287 is characterized as a 4-8-6 MOE gapmer, having a sequence of (from 5' to 3') GCCCTAGCGCGCGACTC (incorporated herein as SEQ ID NO: 33), wherein each of nucleosides 1-4 and 13-18 are 2'-O-methoxyethylribose modified nucleosides, and each of nucleosides 5-12 are 2'-deoxynucleosides, wherein the internucleoside linkages between nucleosides 2 to 3, 3 to 4, 13 to 14, 14 to 15, and 15 to 16 are phosphodiester linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 16 to 17, and 17 to 18 are phosphorothioate linkages, and wherein each cytosine is a 5'-methylcytosine.

In certain embodiments, ISIS 801287 is described by the following chemical notation: Ges mCeo mCeo mCes mCds Tds Ads Gds mCds Gds mCds Gds mCeo Geo Aeo mCes Tes mCe; wherein, A=an adenine, mC=a 5'-methylcytosine G=a guanine,
T=a thymine,
e=a 2'-O-methoxyethylribose modified sugar
d=a 2'-deoxyribose sugar,
s=a phosphorothioate internucleoside linkage, and
o=a phosphodiester internucleoside linkage.
In certain embodiments, ISIS 801287 is described by the following chemical structure, or a salt thereof:
(SEQ ID NO: 33)
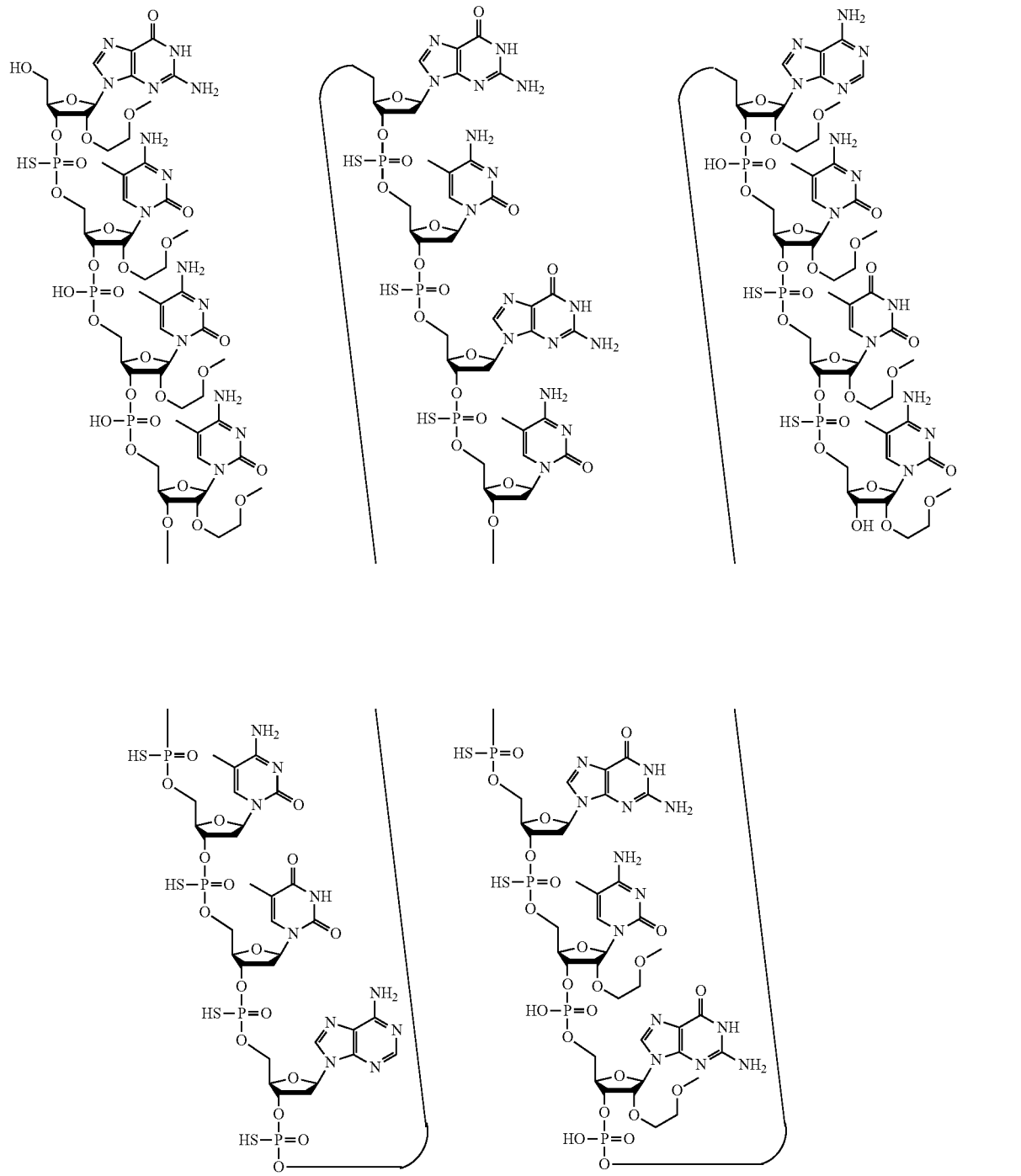

Structure 1. ISIS 801287

In certain embodiments, the sodium salt of ISIS 801287 is described by the following chemical structure:

7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate linkages, and wherein each cytosine is a 5'-methylcytosine.

(SEQ ID NO: 33)

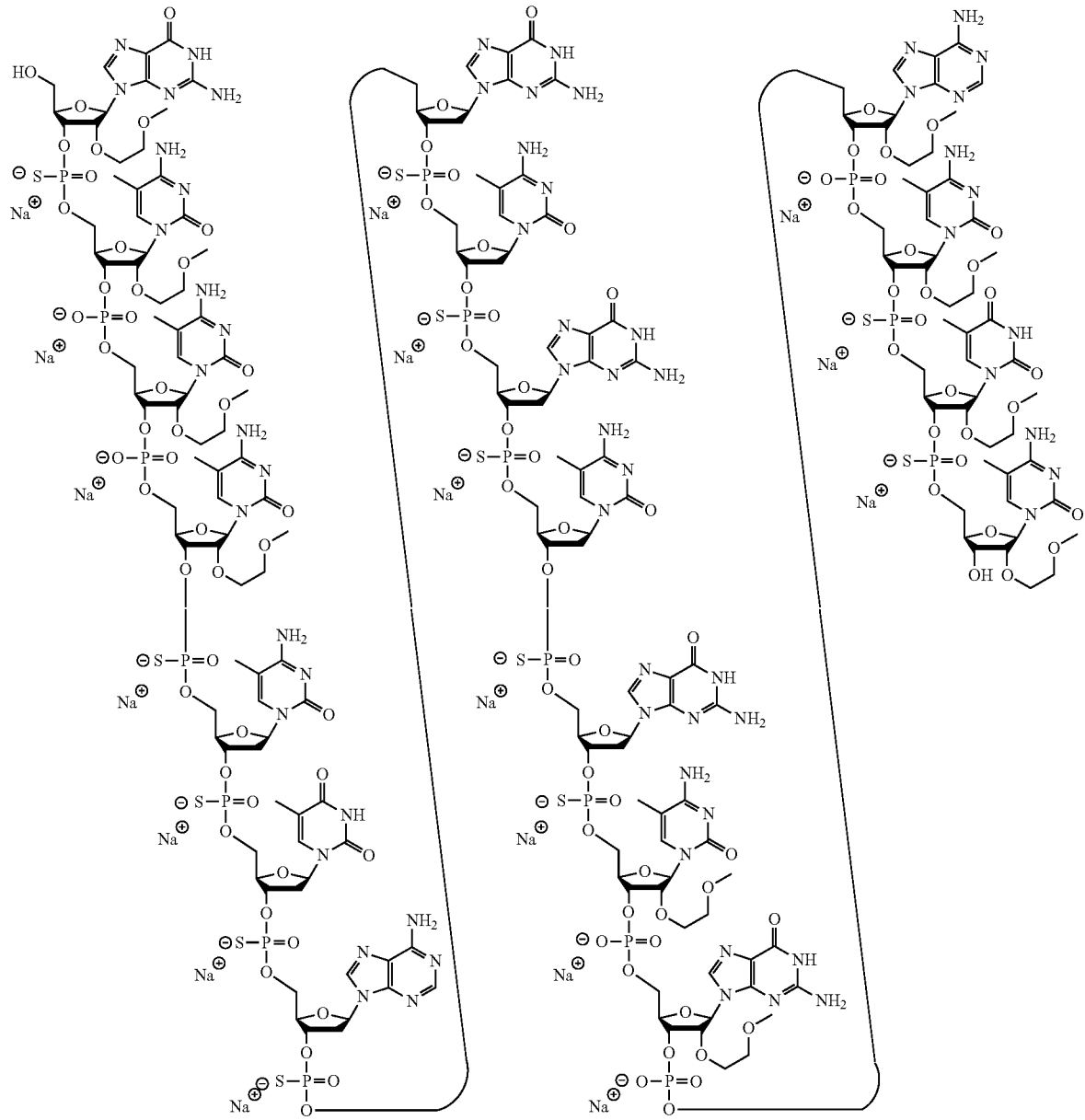

Structure 2. The Sodium Salt of ISIS 801287

2. ISIS 806679

In certain embodiments, ISIS 806679 is characterized as a 6-10-4 MOE gapmer, having a sequence of (from 5' to 3') GGTTAATCTTTATCAGGTCT (incorporated herein as SEQ ID NO: 49), wherein each of nucleosides 1-6 and 17-20 are 2'-O-methoxyethylribose modified nucleosides, and each of nucleosides 7-16 are 2'-deoxynucleosides, wherein the internucleoside linkages between nucleosides 2 to 3, 3 to 4, 4 to 5, 5 to 6, 6 to 7, and 17 to 18 are phosphodiester linkages and the internucleoside linkages between nucleosides 1 to 2, In certain embodiments, ISIS 806679 is described by the following chemical notation: Ges Geo Teo Teo Aeo Aeo Tds mCds Tds Tds Tds Ads Tds mCds Ads Gds Geo Tes mCes Te; wherein, A=an adenine,
mC=a 5'-methylcytosine
G=a guanine,
T=a thymine,
e=a 2'-O-methoxyethylribose modified sugar
d=a 2'-deoxyribose sugar,
s=a phosphorothioate internucleoside linkage, and
o=a phosphodiester internucleoside linkage.

In certain embodiments, ISIS 806679 is described by the following chemical structure, or a salt thereof:
(SEQ ID NO: 49)
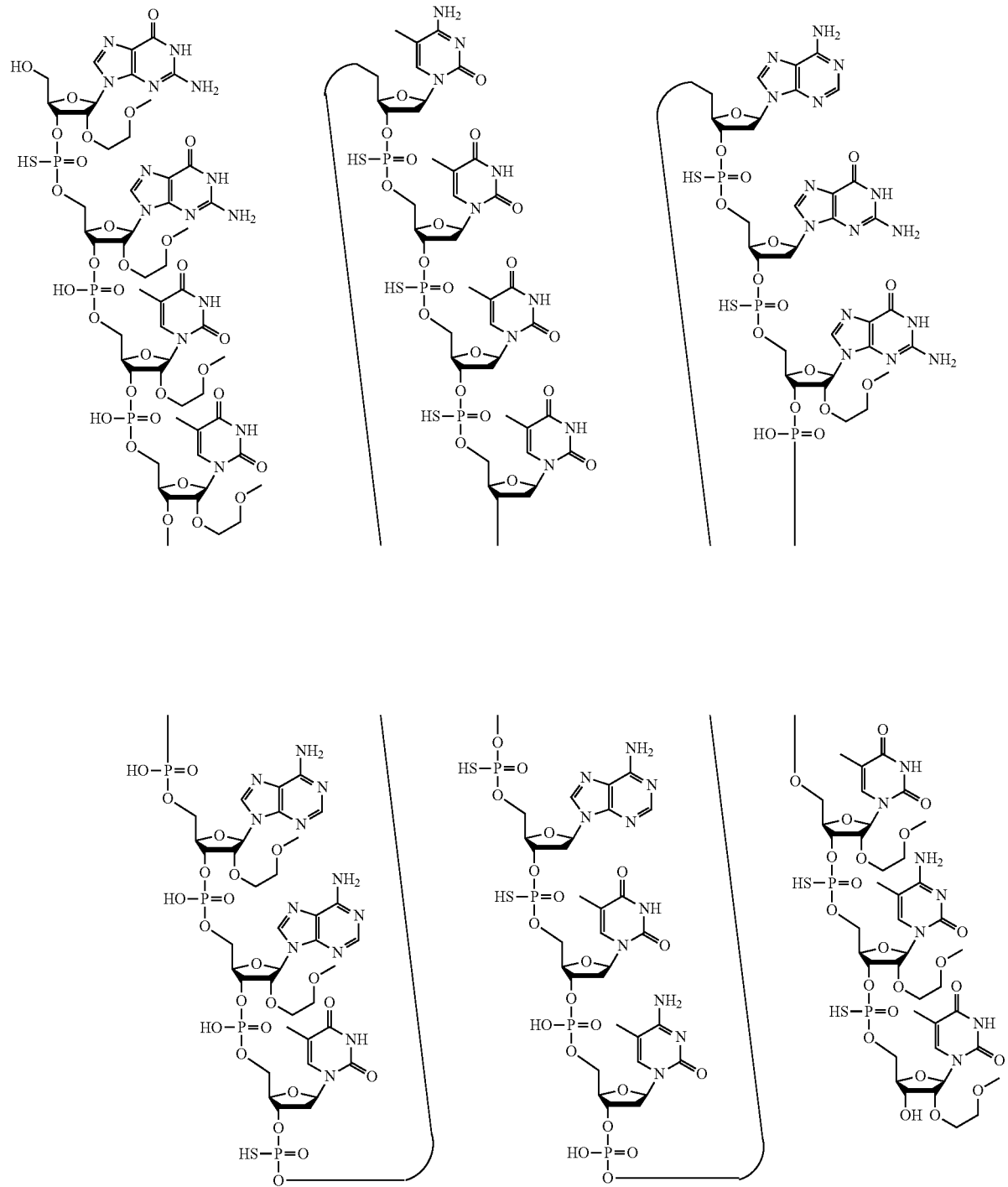

Structure 3. ISIS 806679

In certain embodiments, the sodium salt of ISIS 806679 is described by the following chemical structure:

(SEQ ID NO: 49)

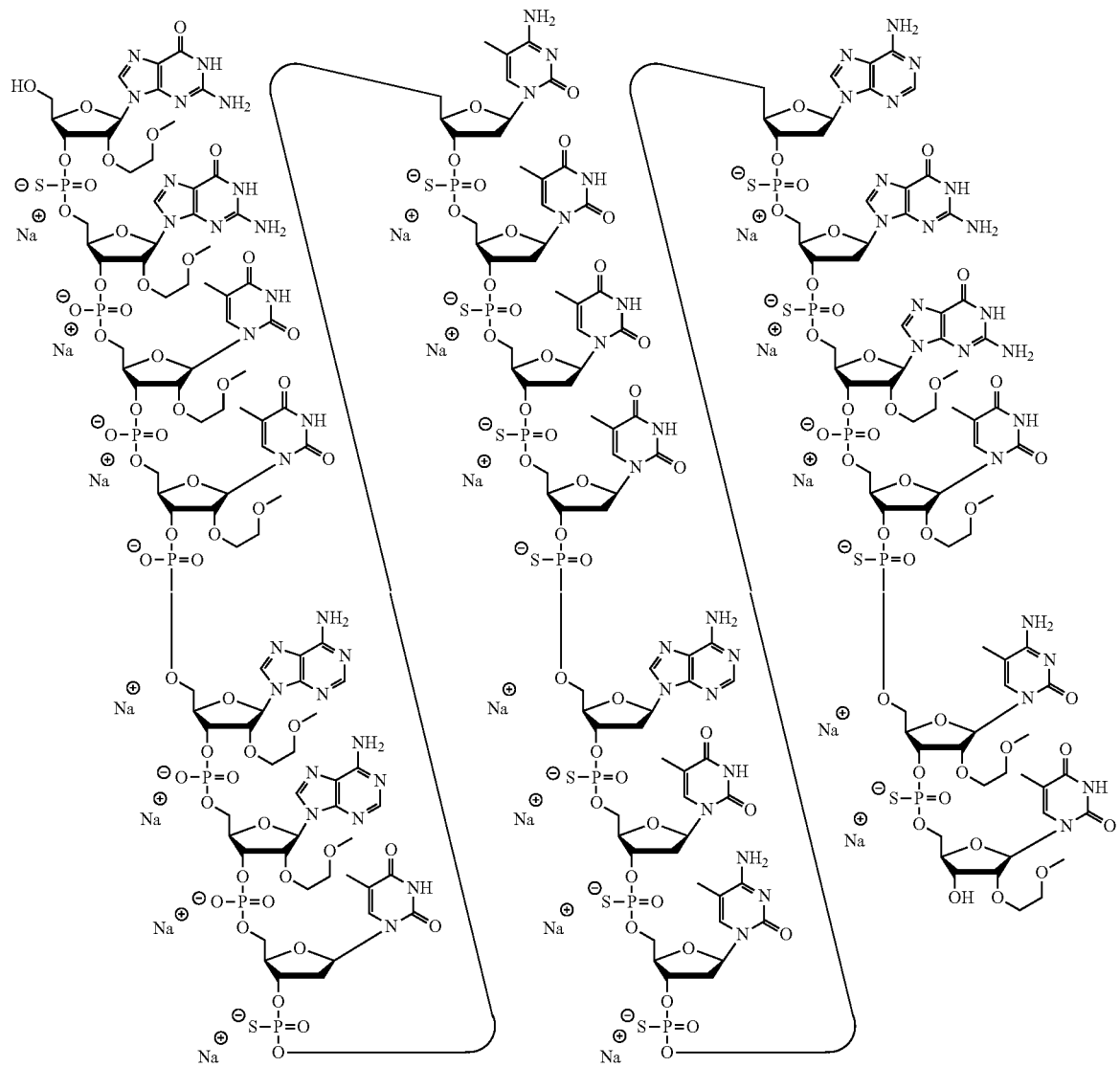

Structure 4. The Sodium Salt of ISIS 806679

3. ISIS 802473

In certain embodiments, ISIS 802473 is characterized as a 4-8-6 MOE gapmer, having a sequence of (from 5' to 3') GCCTTACTCTAGGACCAA (incorporated herein as SEQ ID NO: 47), wherein each of nucleosides 1-4 and 13-18 are 2'-O-methoxyethylribose modified nucleosides, and each of nucleosides 5-12 are 2'-deoxynucleosides, wherein the internucleoside linkages between nucleosides 2 to 3, 3 to 4, 13 to 14, 14 to 15, and 15 to 16 are phosphodiester linkages and the internucleoside linkages between nucleosides are 1 to 2, 4 to 5, 5 to 6, 6 to 7, 7 to 8, 8 to 9, 9 to 10, 10 to 11, 11 to 12, 12 to 13, 16 to 17, and 17 to 18 are phosphorothioate linkages, and wherein each cytosine is a 5'-methylcytosine.

In certain embodiments, ISIS 802473 is described by the following chemical notation: Ges mCeo mCeo Tes Tds Ads mCds Tds mCds Tds Ads Gds Geo Aeo mCeo mCes Aes Ae; wherein, A=an adenine,
mC=a 5'-methylcytosine
G=a guanine,
T=a thymine,
e=a 2'-O-methoxyethylribose modified sugar
d=a 2'-deoxyribose sugar,
s=a phosphorothioate internucleoside linkage, and
o=a phosphodiester internucleoside linkage.

In certain embodiments, ISIS 802473 is described by the following chemical structure, or a salt thereof:
(SEQ ID NO: 47)
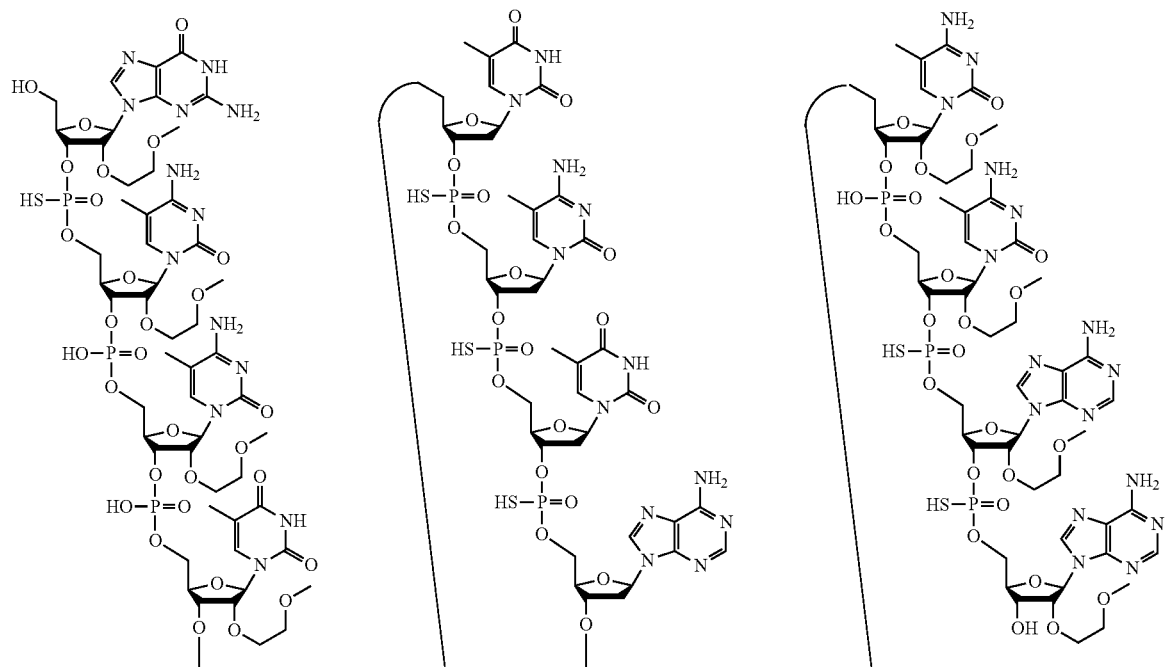
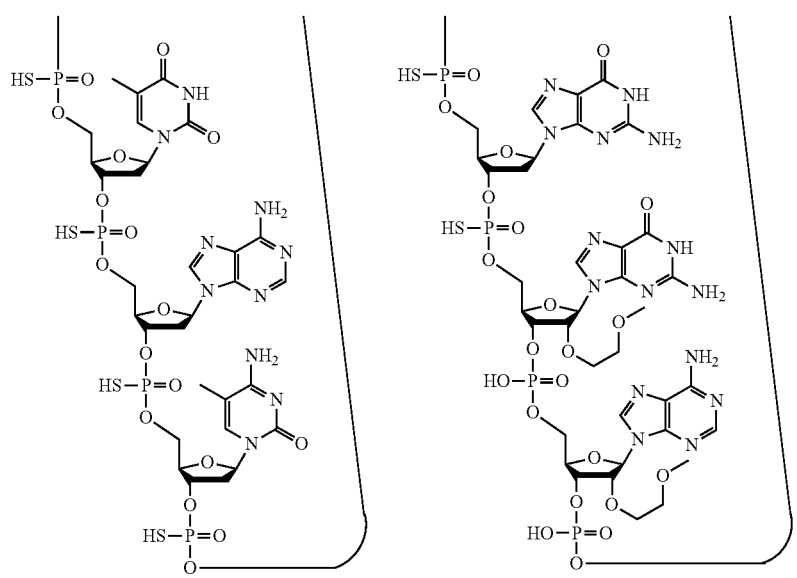

Structure 5. ISIS 802473

In certain embodiments, the sodium salt of ISIS 802473 is described by the following chemical structure:

(SEQ ID NO: 47)

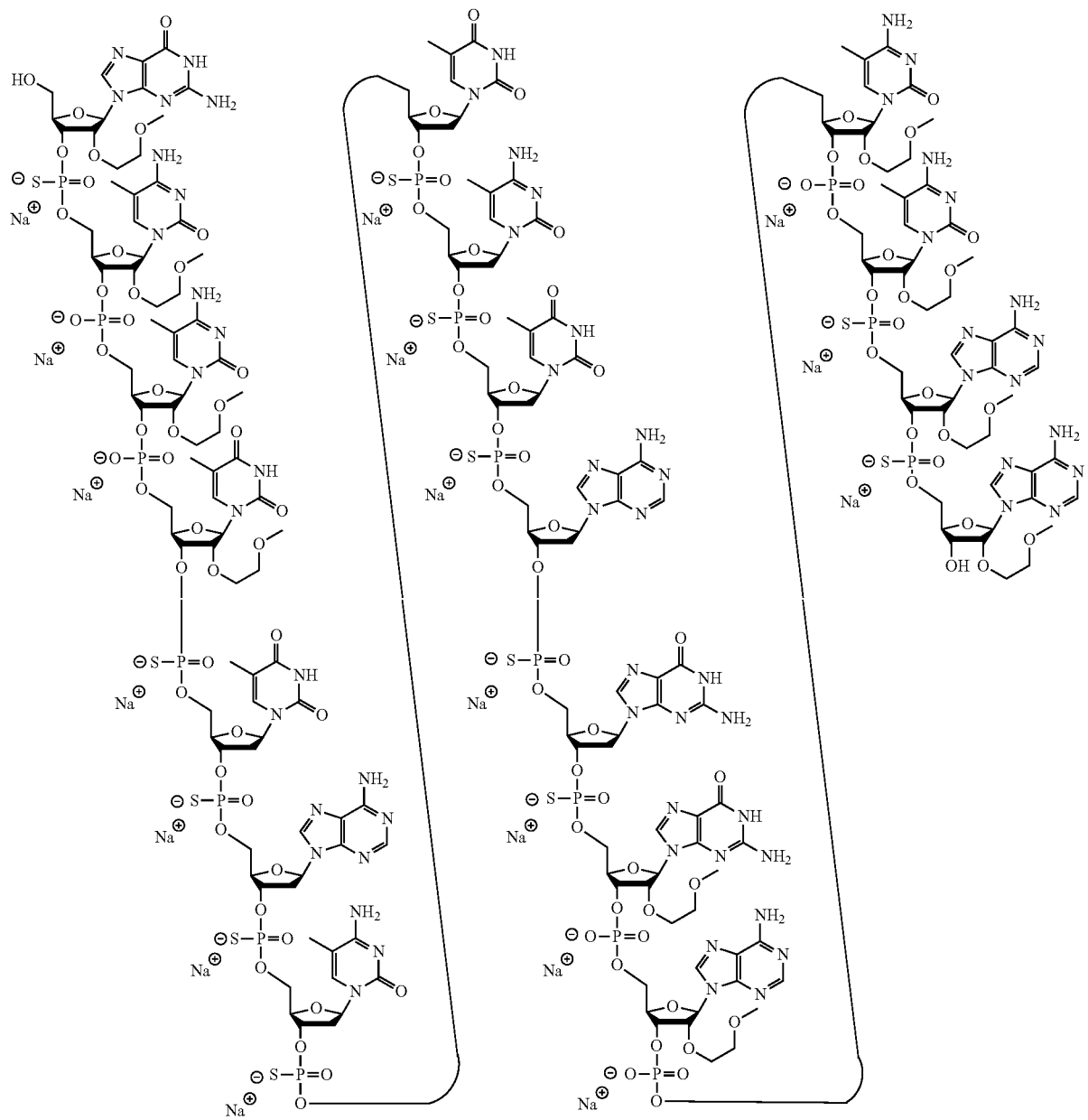

Structure 6. The Sodium Salt of ISIS 802473

4. ISIS 802459

In certain embodiments, ISIS 802459 is characterized as a 3-10-7 MOE gapmer, having a sequence of (from 5' to 3') GCCTTACTCTAGGACCAAGA (incorporated herein as SEQ ID NO: 21), wherein each of nucleosides 1-3 and 14-20 are 2'-O-methoxyethylribose modified nucleosides, and each of nucleosides 4-13 are 2'-deoxynucleosides, wherein the internucleoside linkages between nucleosides 2 to 3, 3 to 4, 14 to 15, 15 to 16, 16 to 17, and 17 to 18 are phosphodiester linkages and the internucleoside linkages between nucleosides are 1 to 2, 4 to 5, 5 to 6, 6 to 7, 7 to 8, 8 to 9, 9 to 10, 10 to 11, 11 to 12, 12 to 13, 13 to 14, 18 to 19, and 19 to 20 are phosphorothioate linkages, and wherein each cytosine is a 5'-methylcytosine.

In certain embodiments, ISIS 802459 is described by the following chemical notation: Ges mCeo mCeo Tds Tds Ads mCds Tds mCds Tds Ads Gds Gds Aeo mCeo mCeo Aeo Aes Ges Ae; wherein, A=an adenine, mC=a 5'-methylcytosine G=a guanine,
T=a thymine,
e=a 2'-O-methoxyethylribose modified sugar
d=a 2'-deoxyribose sugar,
s=a phosphorothioate internucleoside linkage, and
o=a phosphodiester internucleoside linkage.
In certain embodiments, ISIS 802459 is described by the following chemical structure, or a salt thereof:
(SEQ ID NO: 21)
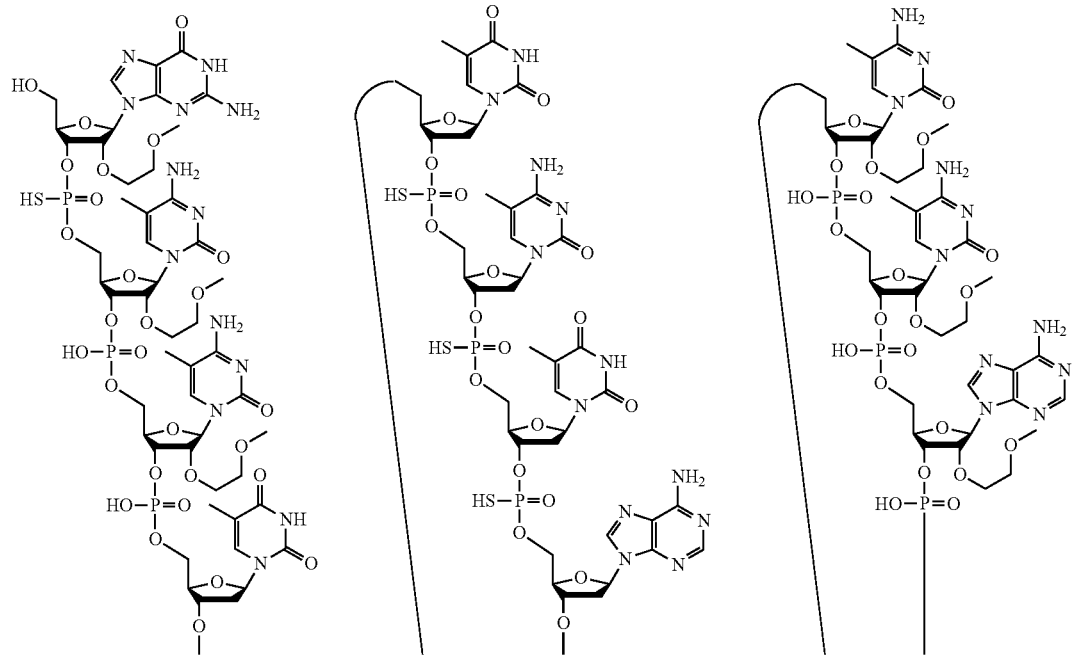
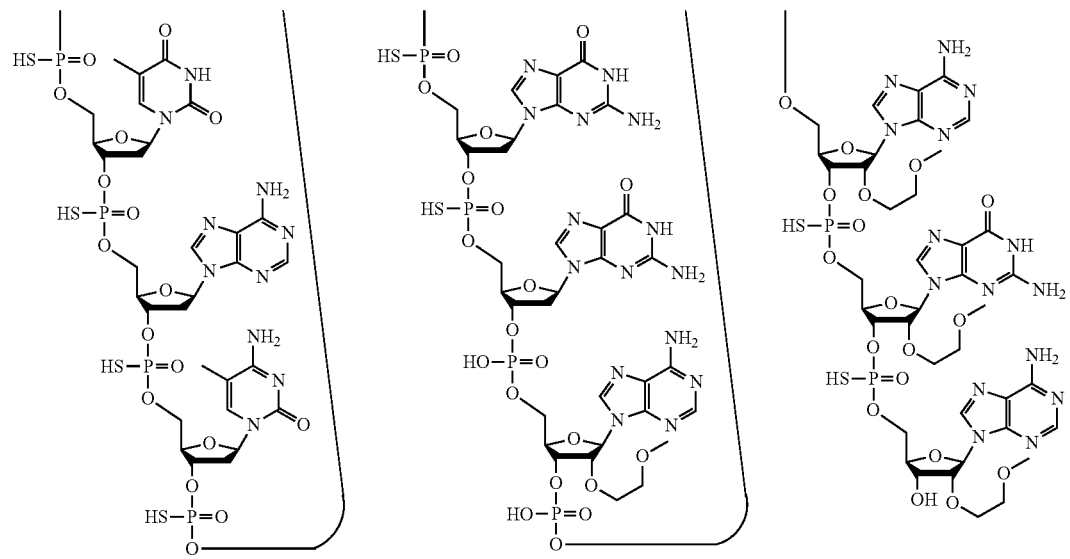

Structure 7 ISIS 802459

In certain embodiments, the sodium salt of ISIS 802459 is described by the following chemical structure:

(SEQ ID NO: 21)

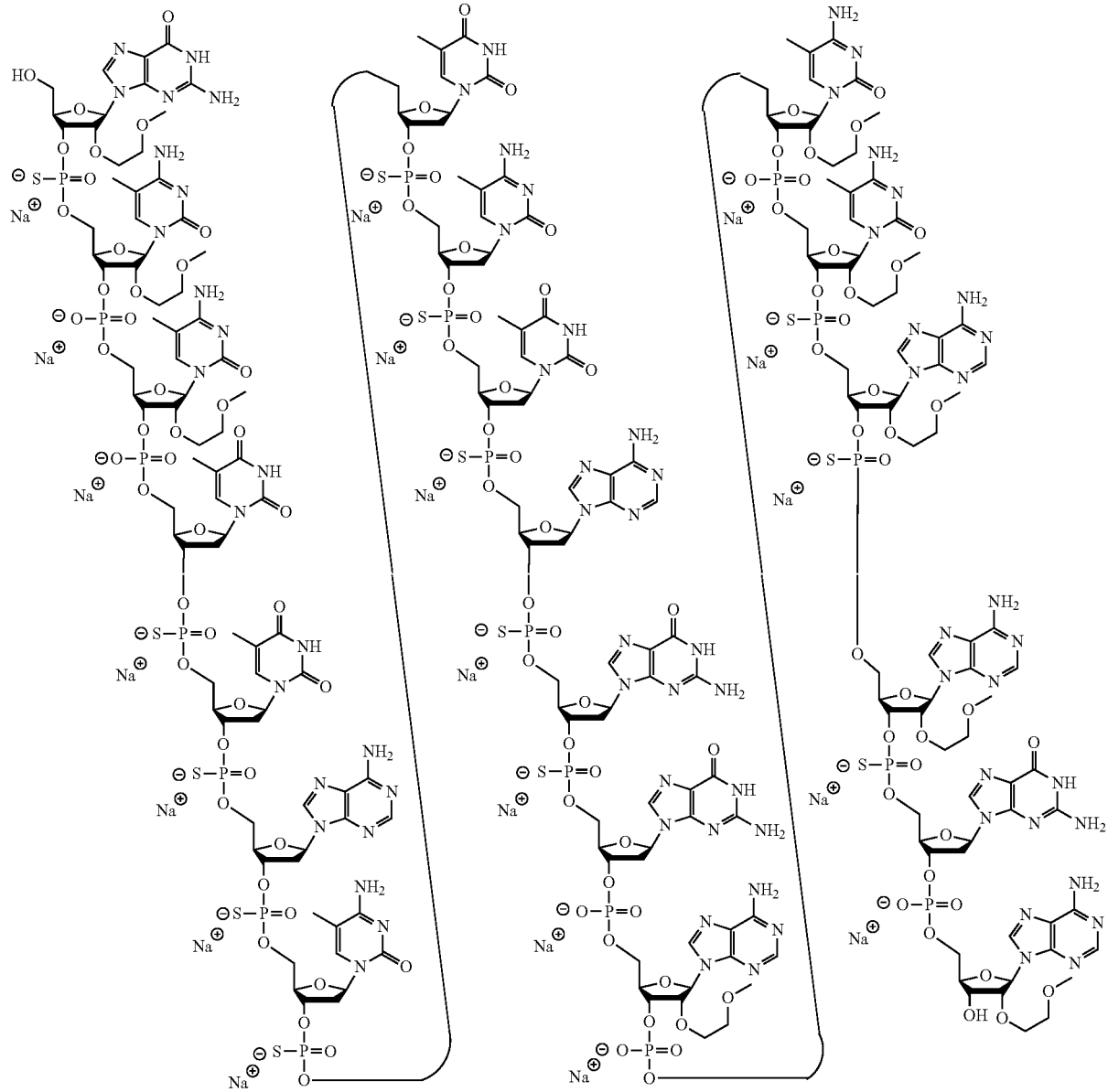

Structure 8. The Sodium Salt of ISIS 802459

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Oligonucleotides Targeting Human C9ORF72

The antisense oligonucleotides in the table below were designed as MOE gapmers. The central gap segment of each gapmer contains 2'-deoxynucleosides and is flanked by wing segments on both the 5' end and on the 3' end containing nucleosides that each comprise a 2'-MOE group. The specific motif of each gapmer is listed in table below, represented by three numbers separated by hyphens. The numbers represent the number of nucleosides in the 5'-wing, the gap, and the 3'-wing, respectively. All cytosine residues throughout each oligonucleotide are 5-methylcytosines. The internucleoside linkages for the gapmers are mixed phosphorothioate and phosphodiester linkages. The internucleoside linkages for each gapmer are presented in the Linkage column, where 'o' indicates a phosphodiester linkage and 's' indicates a phosphorothioate linkage.

Each antisense oligonucleotide listed in the table below is targeted to the human C9ORF72 genomic sequence, designated herein as SEQ ID NO: 2 (the complement of GENBANK Accession No. NT_008413.18 truncated from nucleosides 27535000 to 27565000). "Start site" indicates the 5'-most nucleoside to which the gapmer is targeted in the human genomic sequence. "Stop site" indicates the 3'-most nucleoside to which the gapmer is targeted human genomic sequence.

TABLE 6

Antisense oligonucleotides targeting human C9ORF72

| Isis No. | Start Site | Stop Site | Sequence | Linkage | Motif | SEQ ID NO |
|---|---|---|---|---|---|---|
| 791656 | 1445 | 1464 | CCGGCCCCTAGCGCGCGACT | soosssssssssssooooss | 3-10-7 | 22 |
| 791657 | 1445 | 1464 | CCGGCCCCTAGCGCGCGACT | soooosssssssssssooooss | 4-10-6 | 22 |
| 791658 | 1445 | 1464 | CCGGCCCCTAGCGCGCGACT | sooooossssssssssssoss | 6-10-4 | 22 |
| 791659 | 1445 | 1464 | CCGGCCCCTAGCGCGCGACT | sooooooosssssssssssss | 7-10-3 | 22 |
| 791660 | 1445 | 1463 | CGGCCCCTAGCGCGCGACT | sooooosssssssssssooss | 5-9-5 | 23 |
| 791661 | 1446 | 1464 | CCGGCCCCTAGCGCGCGAC | sooooosssssssssssooss | 5-9-5 | 24 |
| 791662 | 1445 | 1463 | CGGCCCCTAGCGCGCGACT | sooosssssssssssooss | 4-9-6 | 23 |
| 791663 | 1446 | 1464 | CCGGCCCCTAGCGCGCGAC | sooosssssssssssooss | 4-9-6 | 24 |
| 791664 | 1445 | 1463 | CGGCCCCTAGCGCGCGACT | sooooossssssssssssoss | 6-9-4 | 23 |
| 791665 | 1446 | 1464 | CCGGCCCCTAGCGCGCGAC | sooooossssssssssssoss | 6-9-4 | 24 |
| 801274 | 1440 | 1459 | CCCTAGCGCGCGACTCCTGA | sooossssssssssssooooss | 4-10-6 | 25 |
| 801275 | 1441 | 1460 | CCCCTAGCGCGCGACTCCTG | sooossssssssssssooooss | 4-10-6 | 26 |
| 801276 | 1442 | 1461 | GCCCCTAGCGCGCGACTCCT | sooossssssssssssooooss | 4-10-6 | 27 |
| 801277 | 1443 | 1462 | GGCCCCTAGCGCGCGACTCC | sooossssssssssssooooss | 4-10-6 | 28 |
| 801278 | 1444 | 1463 | CGGCCCCTAGCGCGCGACTC | sooossssssssssssooooss | 4-10-6 | 29 |
| 801279 | 1440 | 1459 | CCCTAGCGCGCGACTCCTGA | sooooossssssssssssoss | 6-10-4 | 25 |
| 801280 | 1441 | 1460 | CCCCTAGCGCGCGACTCCTG | sooooossssssssssssoss | 6-10-4 | 26 |
| 801281 | 1442 | 1461 | GCCCCTAGCGCGCGACTCCT | sooooossssssssssssoss | 6-10-4 | 27 |
| 801282 | 1443 | 1462 | GGCCCCTAGCGCGCGACTCC | sooooossssssssssssoss | 6-10-4 | 28 |
| 801283 | 1444 | 1463 | CGGCCCCTAGCGCGCGACTC | sooooossssssssssssoss | 6-10-4 | 29 |
| 801284 | 1441 | 1458 | CCTAGCGCGCGACTCCTG | soosssssssssooooss | 4-8-6 | 30 |
| 801285 | 1442 | 1459 | CCCTAGCGCGCGACTCCT | soosssssssssooooss | 4-8-6 | 31 |
| 801286 | 1443 | 1460 | CCCCTAGCGCGCGACTCC | soosssssssssooooss | 4-8-6 | 32 |
| 801287 | 1444 | 1461 | GCCCCTAGCGCGCGACTC | soosssssssssooooss | 4-8-6 | 33 |
| 801288 | 1445 | 1462 | GGCCCCTAGCGCGCGACT | soosssssssssooooss | 4-8-6 | 34 |
| 801289 | 1446 | 1463 | CGGCCCCTAGCGCGCGAC | soosssssssssooooss | 4-8-6 | 35 |
| 801290 | 1441 | 1458 | CCTAGCGCGCGACTCCTG | sooooossssssssssoss | 6-8-4 | 30 |
| 801291 | 1442 | 1459 | CCCTAGCGCGCGACTCCT | sooooossssssssssoss | 6-8-4 | 31 |
| 801292 | 1443 | 1460 | CCCCTAGCGCGCGACTCC | sooooossssssssssoss | 6-8-4 | 32 |
| 801293 | 1444 | 1461 | GCCCCTAGCGCGCGACTC | sooooossssssssssoss | 6-8-4 | 33 |
| 801294 | 1445 | 1462 | GGCCCCTAGCGCGCGACT | sooooossssssssssoss | 6-8-4 | 34 |
| 801295 | 1446 | 1463 | CGGCCCCTAGCGCGCGAC | sooooossssssssssoss | 6-8-4 | 35 |

TABLE 6-continued

Antisense oligonucleotides targeting human C9ORF72

| Isis No. | Start Site | Stop Site | Sequence | Linkage | Motif | SEQ ID NO |
|---|---|---|---|---|---|---|
| 801296 | 1403 | 1422 | AGGCTGCGGTTGTTTCCCTC | sooosssssssssssooosss | 4-10-6 | 36 |
| 801297 | 1404 | 1423 | CAGGCTGCGGTTGTTTCCCT | sooosssssssssssooosss | 4-10-6 | 37 |
| 801298 | 1403 | 1421 | GGCTGCGGTTGTTTCCCTC | sooooossssssssssooss | 5-9-5 | 38 |
| 801299 | 1404 | 1422 | AGGCTGCGGTTGTTTCCCT | sooooossssssssssooss | 5-9-5 | 39 |
| 801300 | 1405 | 1423 | CAGGCTGCGGTTGTTTCCC | sooooossssssssssooss | 5-9-5 | 40 |
| 801301 | 1403 | 1421 | GGCTGCGGTTGTTTCCCTC | sooosssssssssssoooss | 4-9-6 | 38 |
| 801302 | 1404 | 1422 | AGGCTGCGGTTGTTTCCCT | sooosssssssssssoooss | 4-9-6 | 39 |
| 801303 | 1405 | 1423 | CAGGCTGCGGTTGTTTCCC | sooosssssssssssoooss | 4-9-6 | 40 |
| 801304 | 1403 | 1421 | GGCTGCGGTTGTTTCCCTC | sooooossssssssssosss | 6-9-4 | 38 |
| 801305 | 1404 | 1422 | AGGCTGCGGTTGTTTCCCT | sooooossssssssssosss | 6-9-4 | 39 |
| 801306 | 1405 | 1423 | CAGGCTGCGGTTGTTTCCC | sooooossssssssssosss | 6-9-4 | 40 |
| 801307 | 1403 | 1420 | GCTGCGGTTGTTTCCCTC | sooossssssssssooosss | 4-8-6 | 41 |
| 801308 | 1404 | 1421 | GGCTGCGGTTGTTTCCCT | sooossssssssssooosss | 4-8-6 | 42 |
| 801309 | 1405 | 1422 | AGGCTGCGGTTGTTTCCC | sooossssssssssooosss | 4-8-6 | 43 |
| 801310 | 1406 | 1423 | CAGGCTGCGGTTGTTTCC | sooossssssssssooosss | 4-8-6 | 44 |
| 801311 | 1403 | 1420 | GCTGCGGTTGTTTCCCTC | sooooossssssssssoss | 6-8-4 | 41 |
| 801312 | 1404 | 1421 | GGCTGCGGTTGTTTCCCT | sooooossssssssssoss | 6-8-4 | 42 |
| 801313 | 1405 | 1422 | AGGCTGCGGTTGTTTCCC | sooooossssssssssoss | 6-8-4 | 43 |
| 801314 | 1406 | 1423 | CAGGCTGCGGTTGTTTCC | sooooossssssssssoss | 6-8-4 | 44 |
| 801315 | 1403 | 1422 | AGGCTGCGGTTGTTTCCCTC | sooooosssssssssssoss | 6-10-4 | 36 |
| 801316 | 1404 | 1423 | CAGGCTGCGGTTGTTTCCCT | sooooosssssssssssoss | 6-10-4 | 37 |
| 802459 | 7990 | 8009 | GCCTTACTCTAGGACCAAGA | soosssssssssssooooss | 3-10-7 | 21 |
| 802460 | 8012 | 8031 | TCTGTCTTTGGAGCCCAAAT | soosssssssssssooooss | 3-10-7 | 45 |
| 802461 | 8186 | 8205 | CTGCGATCCCCATTCCAGTT | soosssssssssssooooss | 3-10-7 | 46 |
| 802462 | 7990 | 8009 | GCCTTACTCTAGGACCAAGA | sooosssssssssssooosss | 4-10-6 | 21 |
| 802463 | 8012 | 8031 | TCTGTCTTTGGAGCCCAAAT | sooosssssssssssooosss | 4-10-6 | 45 |
| 802464 | 8186 | 8205 | CTGCGATCCCCATTCCAGTT | sooosssssssssssooosss | 4-10-6 | 46 |
| 802465 | 7990 | 8009 | GCCTTACTCTAGGACCAAGA | sooooosssssssssssoss | 6-10-4 | 21 |
| 802466 | 8012 | 8031 | TCTGTCTTTGGAGCCCAAAT | sooooosssssssssssoss | 6-10-4 | 45 |
| 802467 | 8186 | 8205 | CTGCGATCCCCATTCCAGTT | sooooosssssssssssoss | 6-10-4 | 46 |
| 802468 | 7990 | 8009 | GCCTTACTCTAGGACCAAGA | soooooosssssssssssss | 7-10-3 | 21 |
| 802469 | 8012 | 8031 | TCTGTCTTTGGAGCCCAAAT | soooooosssssssssssss | 7-10-3 | 45 |
| 802470 | 8186 | 8205 | CTGCGATCCCCATTCCAGTT | soooooosssssssssssss | 7-10-3 | 46 |
| 802471 | 7992 | 8009 | GCCTTACTCTAGGACCAA | sosssssssssooooss | 3-8-7 | 47 |
| 802472 | 8014 | 8031 | TCTGTCTTTGGAGCCCAA | sosssssssssooooss | 3-8-7 | 48 |
| 802473 | 7992 | 8009 | GCCTTACTCTAGGACCAA | sooossssssssooooss | 4-8-6 | 47 |
| 802474 | 8014 | 8031 | TCTGTCTTTGGAGCCCAA | sooossssssssooooss | 4-8-6 | 48 |
| 802475 | 7992 | 8009 | GCCTTACTCTAGGACCAA | soooossssssssssoss | 6-8-4 | 47 |

TABLE 6-continued

Antisense oligonucleotides targeting human C9ORF72

| Isis No. | Start Site | Stop Site | Sequence | Linkage | Motif | SEQ ID NO |
|---|---|---|---|---|---|---|
| 802476 | 8014 | 8031 | TCTGTCTTTGGAGCCCAA | soooosssssssssoss | 6-8-4 | 48 |
| 802477 | 7992 | 8009 | GCCTTACTCTAGGACCAA | sooooosssssssssss | 7-8-3 | 47 |
| 802478 | 8014 | 8031 | TCTGTCTTTGGAGCCCAA | sooooosssssssssss | 7-8-3 | 48 |
| 806673 | 1370 | 1389 | GGTTAATCTTTATCAGGTCT | soossssssssssooooss | 3-10-7 | 49 |
| 806674 | 1371 | 1390 | TGGTTAATCTTTATCAGGTC | soossssssssssooooss | 3-10-7 | 50 |
| 806675 | 1372 | 1391 | CTGGTTAATCTTTATCAGGT | soossssssssssooooss | 3-10-7 | 51 |
| 806676 | 1370 | 1389 | GGTTAATCTTTATCAGGTCT | sooosssssssssssoooss | 4-10-6 | 49 |
| 806677 | 1371 | 1390 | TGGTTAATCTTTATCAGGTC | sooossssssssssoooss | 4-10-6 | 50 |
| 806678 | 1372 | 1391 | CTGGTTAATCTTTATCAGGT | sooossssssssssoooss | 4-10-6 | 51 |
| 806679 | 1370 | 1389 | GGTTAATCTTTATCAGGTCT | soooooosssssssssoss | 6-10-4 | 49 |
| 806680 | 1371 | 1390 | TGGTTAATCTTTATCAGGTC | soooooosssssssssoss | 6-10-4 | 50 |
| 806681 | 1372 | 1391 | CTGGTTAATCTTTATCAGGT | soooooosssssssssoss | 6-10-4 | 51 |
| 806682 | 1370 | 1389 | GGTTAATCTTTATCAGGTCT | sooooooosssssssssss | 7-10-3 | 49 |
| 806683 | 1371 | 1390 | TGGTTAATCTTTATCAGGTC | sooooooosssssssssss | 7-10-3 | 50 |
| 806684 | 1372 | 1391 | CTGGTTAATCTTTATCAGGT | sooooooosssssssssss | 7-10-3 | 51 |
| 806685 | 1371 | 1388 | GTTAATCTTTATCAGGTC | soossssssssoooss | 4-8-6 | 52 |
| 806686 | 1372 | 1389 | GGTTAATCTTTATCAGGT | soossssssssoooss | 4-8-6 | 53 |
| 806687 | 1373 | 1390 | TGGTTAATCTTTATCAGG | soossssssssoooss | 4-8-6 | 54 |
| 806688 | 1440 | 1457 | CTAGCGCGCGACTCCTGA | soossssssssoooss | 4-8-6 | 55 |
| 806689 | 1371 | 1388 | GTTAATCTTTATCAGGTC | sooooosssssssssoss | 6-8-4 | 52 |
| 806690 | 1372 | 1389 | GGTTAATCTTTATCAGGT | sooooosssssssssoss | 6-8-4 | 53 |
| 806691 | 1373 | 1390 | TGGTTAATCTTTATCAGG | sooooosssssssssoss | 6-8-4 | 54 |
| 806692 | 1440 | 1457 | CTAGCGCGCGACTCCTGA | sooooosssssssssoss | 6-8-4 | 55 |

Example 2: Tolerability of Antisense Oligonucleotides Targeting Human C9ORF72 in Mice Antisense oligonucleotides described above were tested in mice to assess tolerability of the oligonucleotides. Wild type C57/Bl6 mice each received a single ICV dose of 700 µg of an antisense oligonucleotide listed in the table below. Each treatment group consisted of 4 mice. At 3 hours post injection, each mouse was evaluated according to 7 different criteria. The 7 criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the 700 µg ICV dose, and met all other criteria, it would get a summed score of 0. If another mouse was not bright, alert, and responsive 3 hours after the 700 µg ICV dose but met all other criteria, it would receive a score of 1. The results are presented as the average score for each treatment group.

TABLE 7

Acute tolerability scores

| Isis No. | Score |
|---|---|
| 791656 | 3.25 |
| 791657 | 4.25 |
| 791658 | 3.50 |
| 791659 | 2.00 |
| 791660 | 4.00 |
| 791661 | 4.50 |
| 791662 | 5.25 |
| 791663 | 6.00 |
| 791664 | 3.00 |
| 791665 | 5.75 |
| 801274 | 1.75 |
| 801275 | 3.75 |
| 801276 | 1.25 |

TABLE 7-continued

Acute tolerability scores

| Isis No. | Score |
|---|---|
| 801277 | 1.50 |
| 801278 | 1.75 |
| 801279 | 1.25 |
| 801280 | 6.00 |
| 801281 | 0.00 |
| 801282 | 1.25 |
| 801283 | 1.25 |
| 801284 | 3.00 |
| 801285 | 1.00 |
| 801286 | 1.00 |
| 801287 | 1.50 |
| 801288 | 2.50 |
| 801289 | 7.00 |
| 801290 | 6.00 |
| 801291 | 3.00 |
| 801292 | 2.00 |
| 801293 | 1.00 |
| 801294 | 3.25 |
| 801295 | 4.50 |
| 801296 | 6.25 |
| 801297 | 4.75 |
| 801298 | 5.50 |
| 801299 | 6.25 |
| 801300 | 5.00 |
| 801301 | 6.00 |
| 801302 | 6.50 |
| 801303 | 4.00 |
| 801304 | 5.25 |
| 801305 | 6.00 |
| 801306 | 6.00 |
| 801307 | 5.00 |
| 801308 | 6.00 |
| 801309 | 7.00 |
| 801310 | 3.50 |
| 801311 | 5.50 |
| 801312 | 2.50 |
| 801313 | 5.25 |
| 801314 | 4.50 |
| 801315 | 4.00 |
| 801316 | 2.00 |
| 802459 | 2.00 |
| 802460 | 6.75 |
| 802461 | 1.75 |
| 802462 | 5.75 |
| 802463 | 6.75 |
| 802464 | 1.75 |
| 802465 | 2.25 |
| 802466 | 4.25 |
| 802467 | 0.25 |
| 802468 | 3.25 |
| 802469 | 2.00 |
| 802470 | 0.25 |
| 802471 | 1.25 |
| 802472 | 4.00 |
| 802473 | 0.25 |
| 802474 | 5.25 |
| 802475 | 1.00 |
| 802476 | 5.50 |
| 802477 | 2.50 |
| 802478 | 6.25 |
| 806673 | 0.00 |
| 806674 | 0.25 |
| 806675 | 0.00 |
| 806676 | 0.00 |
| 806677 | 1.00 |
| 806678 | 0.00 |
| 806679 | 1.50 |
| 806680 | 1.00 |
| 806681 | 0.00 |
| 806682 | 5.75 |
| 806683 | 3.75 |
| 806684 | 2.25 |
| 806685 | 1.00 |
| 806686 | 1.00 |
| 806687 | 3.25 |
| 806688 | 3.25 |
| 806689 | 3.00 |
| 806690 | 1.25 |
| 806691 | 6.25 |

Example 3: Tolerability of Oligonucleotides from WO 2014/062691

Oligonucleotides described in WO 2014/062691 were tested in an acute tolerability study in mice. Groups of 3 wild type C57/Bl6 mice were treated and analyzed as described in Example 2. The tested oligonucleotides include those listed in the table below, which are 5-10-5 MOE gapmers with a full phosphorothioate backbone and each cytosine is a 5-methylcytosine. The start and stop sites on SEQ ID NO: 2 that each oligonucleotide is targeted to are shown. The results are presented as the average score for each treatment group in the table below. These results demonstrate that ISIS 576816, ISIS 576974, ISIS 577061, ISIS 577065, ISIS 577083, and ISIS 577056 were poorly tolerated.

TABLE 8

Acute tolerability scores 3h after treatment with antisense oligonucleotides from WO 2014/062691

| Isis No. | Start site | Stop site | Sequence | Score | SEQ ID NO |
|---|---|---|---|---|---|
| 576816 | 7990 | 8009 | GCCTTACTCTAGGACCAAGA | 7.00 | 21 |
| 576974 | 28251 | 28270 | GGGACACTACAAGGTAGTAT | 5.67 | 56 |
| 577061 | 1406 | 1425 | TACAGGCTGCGGTTGTTTCC | 7.00 | 57 |
| 577065 | 1446 | 1465 | CCCGGCCCCTAGCGCGCGAC | 6.00 | 58 |
| 577083 | 3452 | 3471 | GGTAACTTCAAACTCTTGGG | 7.00 | 59 |

TABLE 9

Acute tolerability scores 3h after treatment with antisense oligonucleotides from WO 2014/062691

| Isis No. | Start site | Stop site | Sequence | Score | SEQ ID NO |
|---|---|---|---|---|---|
| 577056 | 1366 | 1385 | AATCTTTATCAGGTCTTTTC | 6.5 | 60 |

Example 4: Antisense Inhibition of a Human C9ORF72 mRNA Variant in HepG2 Cells

Antisense oligonucleotides described above are tested for their effects on C9ORF72 mRNA in vitro. Cultured HepG2 cells at a density of 20,000 cells per well are electroporated with an antisense oligonucleotide. After a treatment period of approximately 24 hours, RNA is isolated from the cells and C9ORF72 mRNA levels are measured by quantitative real-time PCR. Human primer probe set RTS3905 (forward primer sequence GGGTCTAGCAAGAGCAGGTG, designated herein as SEQ ID NO: 12; reverse primer sequence GTCTTGGCAACAGCTGGAGAT, designated herein as SEQ ID NO: 13; probe sequence TGATGTCGACTCTTT-GCCCACCGC, designated herein as SEQ ID NO: 14—a TAQ-man primer probe set) are used. RTS3905 detects an mRNA variant (e.g. NM_001256054.1) processed from a pre-mRNA variant containing the hexanucleotide repeat. The mRNA variant processed from a pre-mRNA variant containing the hexanucleotide repeat is herein the "C9ORF72 pathogenic associated mRNA variant." A pre-mRNA contains the hexanucleotide repeat when transcription of the pre-mRNA begins in the region from the start site of exon 1A to the start site of exon 1B (generally nucleotides 1107 to 1520 of the genomic sequence: SEQ ID NO: 2, the complement of GENBANK Accession No. NT_008413.18 truncated from nucleosides 27535000 to 2756500. Therefore, oligonucleotides designed in this region selectively target the pre-mRNA variant containing the hexanucleotide repeat. RTS3905 measures an mRNA product (i.e. the C9ORF72 pathogenic associated mRNA variant) of the pre-mRNA variant containing the hexanucleotide repeat and, therefore, measures the reduction of the pre-mRNA variant containing the hexanucleotide repeat. The levels of the C9ORF72 pathogenic associated mRNA variant are normalized to the total RNA content of the cell, as measured by RIBOGREEN®, then the normalized mRNA variant levels are compared to those of cells that were not treated with antisense oligonucleotide.

Example 5: Dose-Dependent Antisense Inhibition of a Human C9ORF72 mRNA Variant

Antisense oligonucleotides described above are tested at various doses in HepG2 cells. Cells are plated at a density of 20,000 cells per well and electroporated with antisense oligonucleotide. After a treatment period of approximately 16 hours or 24 hours, RNA is isolated from the cells and C9ORF72 mRNA levels are measured by quantitative real-time PCR. Human C9ORF72 primer probe set RTS3905 is used to measure the C9ORF72 pathogenic associated mRNA variant. The levels of the C9ORF72 pathogenic associated mRNA variant are adjusted according to total RNA content, as measured by RIBOGREEN. The half maximal inhibitory concentration ($IC_{50}$) of each oligonucleotide is calculated based on the inhibition of mRNA variant levels observed at each individual dose of antisense oligonucleotide.

Example 6: Antisense Inhibition of C9ORF72 by Human-Rhesus Cross-Reactive Antisense Oligonucleotides in LLC-MK2 Cells Antisense oligonucleotides described above that are fully cross-reactive with a rhesus C9ORF72 nucleic acid are tested for their effects on rhesus C9ORF72 mRNA in vitro. Cultured rhesus LLC-MK2 cells at a density of 20,000 cells per well are electroporated with antisense oligonucleotide. After a treatment period of approximately 24 hours, RNA is isolated from the cells and C9ORF72 mRNA levels are measured by quantitative real-time PCR. Primer probe set RTS3750 (forward sequence TGTGACAGTTGGAAT-GCAGTGA, designated herein as SEQ ID NO: 15; reverse sequence GCCACTTAAAGCAATCTCTGTCTTG, designated herein as SEQ ID NO: 16; probe sequence TCGACTCTTTGCCCACCGCCA, designated herein as SEQ ID NO: 17—a TAQ-man primer probe set) is used to measure total C9ORF72 mRNA levels. RTS3750 targets exon 2 of the mRNA transcripts and, therefore, measures total mRNA transcripts. C9ORF72 mRNA levels are adjusted according to total RNA content, as measured by RIBOGREEN®, then the normalized mRNA variant levels are compared to those of cells that were not treated with antisense oligonucleotide.

Example 7: Dose-Dependent Antisense Inhibition of Human C9ORF72 mRNA in LLC-MK2

Antisense oligonucleotides described above are tested at various doses in LLC-MK2 cells. Cells are plated at a density of 20,000 cells per well and electroporated with antisense oligonucleotide. After a treatment period of approximately 16 hours or 24 hours, RNA is isolated from the cells and C9ORF72 mRNA levels are measured by quantitative real-time PCR. Primer probe set RTS3750 is used to measure total C9ORF72 mRNA levels. C9ORF72 mRNA levels are adjusted according to total RNA content, as measured by RIBOGREEN®, then the normalized mRNA variant levels are compared to those of cells that were not treated with antisense oligonucleotide.

Example 8: Antisense Inhibition of Human C9ORF72 mRNA in a Transgenic Mouse Model Antisense oligonucleotides described above are tested in two BAC transgenic mouse lines, designated herein as C9B41 and C9B183, that each express a truncated human C9ORF72 gene comprising exons 1-5. The truncated human C9ORF72 genes of the C9B41 and C9B183 mouse lines comprise 110 and 450 hexanucleotide repeats, respectively. Each mouse in each treatment group receives 350 µg of an antisense oligonucleotide, then expression levels of human C9ORF72 RNA are analyzed by RT-PCR. Dose responses are also performed.

Example 9: Antisense Inhibition of C9ORF72 mRNA in Patient Fibroblasts

Antisense oligonucleotides described above were tested for their effects on C9ORF72 mRNA in vitro. The antisense oligonucleotides listed in the table below were added to a plate before patient fibroblasts F09-152 were added at a density of 20,000 cells per well. The final concentrations of the antisense oligonucleotides after the addition of the cells are listed in the table below. After 30 seconds of shaking, the cells were electroporated then transferred to a Primaria coated culture plate. After 16 hours, RNA was isolated from the cells, and levels of total C9ORF72 mRNA (i.e., mRNA starting from exon 1A and mRNA starting from exon 1B) and levels of the pathogenic associated mRNA (see Example 4) were measured by RT-qPCR. Human primer probe sets RTS 3750 (see Example 6) and RTS3905 (see Example 4) were used to detect the total C9ORF72 mRNA and C9ORF72 pathogenic associated mRNA, respectively. The levels of the C9ORF72 total mRNA and C9ORF72 pathogenic associated mRNA were normalized to the total RNA content of the cell, as measured by RIBOGREEN®, then the normalized mRNA levels were compared to those of cells that were not treated with antisense oligonucleotide. The results are shown in the table below. An entry of "nd" means not determined. $IC_{50}$ values listed as "nd" were not determined, because the target was not inhibited sufficiently to determine an $IC_{50}$. The results show that all of the oligonucleotides listed below inhibited the pathogenic associated C9ORF72 mRNA variant. Oligonucleotides that do not specifically target the repeat variant pre-mRNA inhibited both the pathogenic associated C9ORF72 mRNA and total C9ORF72 mRNA. Oligonucleotides that specifically target the repeat variant pre-mRNA selectively inhibited the pathogenic associated C9ORF72 mRNA.

TABLE 10

C9ORF72 mRNA levels following antisense inhibition in patient fibroblasts

| Isis No. | Concentration (μM) | Total C9ORF72 mRNA | | Pathogenic associated C9ORF72 mRNA | |
|---|---|---|---|---|---|
| | | Level (% UTC) | IC$_{50}$ (μM) | Level (% UTC) | IC$_{50}$ (μM) |
| 791658 | 0.12 | 87 | nd | 26 | <0.1 |
| | 0.60 | 80 | | 9 | |
| | 3.00 | 87 | | nd | |
| | 15.00 | 105 | | 4 | |
| 791664 | 0.12 | 85 | nd | 13 | <0.1 |
| | 0.60 | 101 | | 7 | |
| | 3.00 | 125 | | 4 | |
| | 15.00 | 114 | | 3 | |
| 801278 | 0.12 | 91 | nd | 19 | <0.1 |
| | 0.60 | 71 | | 7 | |
| | 3.00 | 85 | | nd | |
| | 15.00 | 90 | | nd | |
| 801279 | 0.12 | 98 | nd | 57 | 0.12 |
| | 0.60 | 77 | | 27 | |
| | 3.00 | 77 | | 3 | |
| | 15.00 | 86 | | 5 | |
| 801282 | 0.12 | 100 | nd | 51 | 0.08 |
| | 0.60 | 84 | | 12 | |
| | 3.00 | 97 | | 6 | |
| | 15.00 | 190 | | nd | |
| 801283 | 0.12 | 87 | nd | 40 | <0.1 |
| | 0.60 | 75 | | 8 | |
| | 3.00 | 94 | | 4 | |
| | 15.00 | 111 | | 4 | |
| 801285 | 0.12 | 103 | nd | 35 | <0.1 |
| | 0.60 | 78 | | 23 | |
| | 3.00 | 75 | | 7 | |
| | 15.00 | 79 | | 6 | |
| 801286 | 0.12 | 94 | nd | 33 | <0.1 |
| | 0.60 | 85 | | 14 | |
| | 3.00 | 97 | | 5 | |
| | 15.00 | 88 | | 3 | |
| 801287 | 0.12 | 85 | nd | 31 | <0.1 |
| | 0.60 | 76 | | 11 | |
| | 3.00 | 77 | | 9 | |
| | 15.00 | 87 | | 2 | |
| 801288 | 0.12 | 77 | nd | 13 | <0.1 |
| | 0.60 | 86 | | 11 | |
| | 3.00 | 123 | | 5 | |
| | 15.00 | 177 | | 3 | |
| 801292 | 0.12 | 69 | nd | 29 | <0.1 |
| | 0.60 | 71 | | 12 | |
| | 3.00 | 82 | | 3 | |
| | 15.00 | 71 | | nd | |
| 801293 | 0.12 | 77 | nd | 51 | 0.09 |
| | 0.60 | 70 | | 10 | |
| | 3.00 | 74 | | 3 | |
| | 15.00 | 81 | | 1 | |
| 801294 | 0.12 | 75 | nd | 27 | <0.1 |
| | 0.60 | 67 | | 9 | |
| | 3.00 | 107 | | 7 | |
| | 15.00 | 146 | | 2 | |
| 801316 | 0.12 | 73 | nd | 35 | <0.1 |
| | 0.60 | 68 | | 7 | |
| | 3.00 | 65 | | 1 | |
| | 15.00 | 78 | | 1 | |
| 802459 | 0.12 | 58 | 0.10 | 75 | 0.18 |
| | 0.60 | 15 | | 6 | |
| | 3.00 | 2 | | 11 | |
| | 15.00 | 1 | | 6 | |
| 802464 | 0.12 | 81 | 0.39 | 69 | 0.21 |
| | 0.60 | 31 | | 23 | |
| | 3.00 | 6 | | 7 | |
| | 15.00 | 2 | | 3 | |
| 802465 | 0.12 | 40 | <0.1 | 35 | <0.1 |
| | 0.60 | 7 | | 7 | |
| | 3.00 | 2 | | nd | |
| | 15.00 | 1 | | nd | |
| 802468 | 0.12 | 52 | 0.10 | 40 | <0.1 |
| | 0.60 | 15 | | 13 | |
| | 3.00 | 3 | | 7 | |
| | 15.00 | 2 | | nd | |
| 802469 | 0.12 | 69 | 0.17 | 57 | ~0.5 |
| | 0.60 | 16 | | 9 | |
| | 3.00 | 4 | | nd | |
| | 15.00 | 1 | | nd | |
| 802471 | 0.12 | 71 | 0.27 | 54 | 0.12 |
| | 0.60 | 29 | | 20 | |
| | 3.00 | 6 | | 6 | |
| | 15.00 | 7 | | nd | |
| 802473 | 0.12 | 63 | 0.18 | 48 | <0.1 |
| | 0.60 | 27 | | 14 | |
| | 3.00 | 8 | | 11 | |
| | 15.00 | 4 | | nd | |
| 802477 | 0.12 | 54 | 0.12 | 32 | <0.1 |
| | 0.60 | 16 | | 12 | |
| | 3.00 | 4 | | 11 | |
| | 15.00 | 3 | | 3 | |
| 806676 | 0.12 | 66 | nd | 20 | <0.1 |
| | 0.60 | 66 | | 4 | |
| | 3.00 | 76 | | 2 | |
| | 15.00 | 64 | | nd | |
| 806679 | 0.12 | 71 | nd | 23 | <0.1 |
| | 0.60 | 68 | | 2 | |
| | 3.00 | 78 | | 1 | |
| | 15.00 | 84 | | 1 | |
| 806680 | 0.12 | 89 | nd | 41 | <0.1 |
| | 0.60 | 76 | | 13 | |
| | 3.00 | 65 | | 7 | |
| | 15.00 | 84 | | nd | |
| 806690 | 0.12 | 99 | nd | 44 | <0.1 |
| | 0.60 | 88 | | 17 | |
| | 3.00 | 85 | | 2 | |
| | 15.00 | 77 | | 1 | |

Example 10: Antisense Inhibition of Human C9ORF72 mRNA in a Transgenic Mouse Model Antisense oligonucleotides described above were tested in a BAC transgenic mouse line, C9B41 (see Example 8), that expresses a human C9ORF72 gene comprising the promoter region through exon 5 and 110 hexanucleotide repeats. Each treatment group consisted of 2-3 mice. Each mouse received a single ICVB of 350 μg of an antisense oligonucleotide listed in the tables below or PBS. Two weeks later, the mice were euthanized, and expression levels of the human pathogenic associated C9ORF72 mRNA variant and/or total human C9ORF72 mRNA were analyzed by RT-qPCR as described in Example 9. Analysis of the pathogenic associated C9ORF72 variant mRNA levels was not completed for the oligonucleotides that do not specifically target the C9ORF72 repeat variant pre-mRNA. The results in the tables below show the average percent normalized human C9ORF72 mRNA levels relative to the normalized average for the PBS treated group.

TABLE 11

Human C9ORF72 mRNA levels following antisense inhibition in transgenic mice

| Isis No. | Spinal Cord (% PBS treated) Pathogenic variant | Total | Cortex (% PBS treated) Pathogenic variant | Total |
|---|---|---|---|---|
| 791658 | 6 | 69 | 12 | 47 |
| 791659 | 18 | 72 | 27 | 57 |
| 791664 | 13 | 55 | 15 | 39 |
| 801274 | 49 | 65 | 27 | 37 |
| 801276 | 10 | 47 | 12 | 29 |
| 801277 | 9 | 44 | 10 | 28 |
| 801278 | 8 | 39 | 10 | 27 |
| 801279 | 33 | 55 | 40 | 47 |
| 801281 | 16 | 48 | 17 | 32 |
| 801282 | 18 | 49 | 31 | 42 |
| 801283 | 15 | 46 | 17 | 31 |
| 801285 | 29 | 51 | 24 | 36 |
| 801286 | 37 | 61 | 37 | 47 |
| 801287 | 13 | 47 | 30 | 40 |
| 801288 | 18 | 52 | 39 | 48 |
| 801292 | 25 | 49 | 33 | 40 |
| 801293 | 20 | 50 | 29 | 38 |
| 801310 | 70 | 80 | 68 | 70 |
| 801312 | 43 | 61 | 46 | 55 |
| 801315 | 39 | 59 | 41 | 51 |
| 801316 | 27 | 56 | 50 | 58 |
| 806673 | 38 | 66 | 66 | 66 |
| 806674 | 78 | 88 | 98 | 96 |
| 806675 | 67 | 86 | 81 | 85 |
| 806676 | 29 | 64 | 52 | 58 |
| 806677 | 61 | 77 | 69 | 68 |
| 806678 | 83 | 96 | 95 | 102 |
| 806679 | 24 | 63 | 26 | 44 |
| 806680 | 29 | 62 | 41 | 56 |
| 806681 | 39 | 68 | 36 | 54 |
| 806684 | 44 | 69 | 62 | 64 |
| 806685 | 69 | 87 | 56 | 58 |
| 806686 | 59 | 75 | 57 | 68 |
| 806687 | 74 | 88 | 77 | 80 |
| 806688 | 34 | 62 | 42 | 51 |
| 806689 | 67 | 92 | 87 | 88 |
| 806690 | 28 | 61 | 57 | 68 |
| 806692 | 45 | 64 | 44 | 50 |

TABLE 12

Human C9ORF72 mRNA levels following antisense inhibition in transgenic mice

| Isis No. | Total human C9ORF72 mRNA (% PBS) Spinal Cord | Cortex |
|---|---|---|
| 802459 | 28 | 30 |
| 802461 | 22 | 19 |
| 802464 | 30 | 28 |
| 802465 | 25 | 25 |
| 802467 | 13 | 14 |
| 802468 | 24 | 26 |
| 802469 | 24 | 20 |
| 802470 | 18 | 20 |
| 802471 | 36 | 44 |
| 802473 | 28 | 38 |
| 802475 | 15 | 15 |
| 802477 | 14 | 15 |

Example 11: Dose Dependent Antisense Inhibition of Human C9ORF72 mRNA in a Transgenic Mouse Model Antisense oligonucleotides described above were tested in two BAC transgenic mouse lines, C9B41 and C9B183, that each express a truncated human C9ORF72 gene comprising exons 1-5. The truncated human C9ORF72 genes of the C9B41 and C9B183 mouse lines comprise 110 and 450 hexanucleotide repeats, respectively (see Example 8). Each treatment group consisted of 2-4 mice. Each mouse received a single ICVB of 30 µg, 100 µg, 300 µg, or 700 µg of an antisense oligonucleotide as listed in the tables below or PBS. Two weeks later, the mice were euthanized, and expression levels of the human pathogenic associated C9ORF72 mRNA variant and/or total human C9ORF72 mRNA were analyzed by RT-qPCR as described in Example 9. The results in the tables below show the average percent normalized human C9ORF72 mRNA levels relative to the normalized average for the PBS treated group. A value of 100 or greater means the antisense oligonucleotide did not reduce mRNA or increased the amount of mRNA.

TABLE 13

Human C9ORF72 mRNA levels following dose dependnent antisense inhibition in C9B41 transgenic mice

| Isis No. | Concentration (µg) | Spinal Cord (% PBS treated) Total C9 | Cortex (% PBS treated) Total C9 |
|---|---|---|---|
| 802459 | 30 | 84 | 85 |
|  | 100 | 63 | 61 |
|  | 300 | 33 | 26 |
|  | 700 | 29 | 17 |
| 802473 | 30 | 74 | 90 |
|  | 100 | 60 | 77 |
|  | 300 | 37 | 39 |
|  | 700 | 28 | 26 |

TABLE 14

Human C9ORF72 mRNA levels following dose dependnent antisense inhibition in C9B183 transgenic mice

| Isis No. | Concentration (µg) | Spinal Cord (% PBS treated) Pathogenic variant | Cortex (% PBS treated) Pathogenic variant |
|---|---|---|---|
| 801287 | 30 | 76 | 10 |
|  | 100 | 37 | 75 |
|  | 300 | 21 | 32 |
|  | 700 | 11 | 15 |
| 806679 | 30 | 72 | 13 |
|  | 100 | 59 | 100 |
|  | 300 | 21 | 61 |
|  | 700 | 10 | 16 |
| 806680 | 30 | 94 | 118 |
|  | 100 | 72 | 97 |
|  | 300 | 34 | 89 |
|  | 700 | 30 | 56 |
| 806690 | 30 | 52 | 125 |
|  | 100 | 60 | 131 |
|  | 300 | 43 | 119 |
|  | 700 | 19 | 49 |

Example 12: Tolerability of Antisense Oligonucleotides Targeting Human C9Orf72 in Mice Wild type C57/Bl6 mice each received a single ICV dose of 700 µg of an antisense oligonucleotide listed in the table below, as described in Example 2. Each treatment group consisted of 4 mice. At 8 weeks post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not. After all 7 criteria were evaluated, the scores were summed for each mouse and averaged within each treatment group. The results are presented in the table below.

Animals were sacrificed at 8 weeks. The cortex and spinal cord were collected from each animal, and RT-PCR was performed. Expression levels of allograft inflammatory factor (AIF1) were determined as a measure of inflammation. Expression levels of glial fibrillary acidic protein (GFAP) were also determined as a measure of glial cell activation. Results were normalized to Gpadh and are presented relative to PBS control (1.0) in the table below. "N.D." indicates there was no data because the experiment was not performed. An asterisk indicates that the corresponding result is the average of 1-3 mice.

TABLE 15

Tolerabilty of antisense oligonucleotides targeting C9Orf72 in mice

| ISIS No. | Score 8 weeks after injection | AIF1 (spinal cord) | AIF1 (cerebellum) | GFAP (spinal cord) | GFAP (cortex) | SEQ ID NO. |
|---|---|---|---|---|---|---|
| 791656 | 3.5 | 1.1* | 1.3* | 1.0* | 1.3* | 22 |
| 791657 | 3.5 | 2.3* | 1.0* | 1.4* | 0.8* | 22 |
| 791658 | 0.0 | 1.9 | 1.2 | 1.4 | 1.3 | 22 |
| 791659 | 0.0 | 1.8 | 1.3 | 1.5 | 2.5 | 22 |
| 791660 | 1.8 | 2.5* | 1.4* | 1.9* | 0.8* | 23 |
| 791661 | 1.8 | 1.7* | 1.3* | 1.5* | 1.1* | 24 |
| 791662 | 5.3 | 1.1* | 1.2* | 1.1* | 0.8* | 23 |
| 791663 | 7.0 | N.D. | N.D. | N.D. | N.D. | 24 |
| 791664 | 0.0 | 1.6 | 1.6 | 1.2 | 0.9 | 23 |
| 791665 | 3.5 | 1.9* | 1.5* | 1.9* | 0.9* | 24 |
| 801274 | 0.0 | 1.2 | 1.3 | 1.3 | 1.1 | 25 |
| 801275 | 3.5 | 1.4* | 1.7* | 1.6* | 2.1* | 26 |
| 801276 | 0.0 | 13.1 | 2.6 | 3.7 | 1.2 | 27 |
| 801277 | 0.0 | 2.9 | 1.4 | 2.3 | 1.5 | 28 |
| 801278 | 0.0 | 2.0 | 1.3 | 1.8 | 1.1 | 29 |
| 801279 | 0.0 | 1.2 | 1.4 | 1.3 | 1.0 | 25 |
| 801280 | 5.3 | 1.5* | 1.5* | 1.4* | 1.2* | 26 |
| 801281 | 0.0 | 3.6 | 2.2 | 2.4 | 1.6 | 27 |
| 801282 | 0.0 | 1.2 | 1.2 | 1.2 | 1.0 | 28 |
| 801283 | 0.0 | 1.4 | 1.4 | 1.0 | 0.9 | 29 |
| 801284 | 1.8 | 1.2* | 1.5* | 0.9* | 1.0* | 30 |
| 801285 | 0.0 | 1.2 | 1.2 | 1.1 | 0.8 | 31 |
| 801286 | 0.0 | 1.1 | 1.2 | 1.0 | 1.1 | 32 |
| 801287 | 0.0 | 1.3 | 1.2 | 1.1 | 1.4 | 33 |
| 801288 | 0.0 | 1.3 | 1.3 | 1.1 | 0.9 | 34 |
| 801289 | 7.0 | N.D. | N.D. | N.D. | N.D. | 35 |
| 801290 | 3.5 | 1.2* | 1.3* | 1.0* | 1.1* | 30 |
| 801291 | 0.0 | 2.2 | 2.2 | 1.5 | 1.1 | 31 |
| 801292 | 0.0 | 1.3 | 1.3 | 1.2 | 0.9 | 32 |
| 801293 | 0.0 | 1.6 | 1.6 | 1.3 | 1.5 | 33 |
| 801294 | 0.0 | 1.2 | 1.2 | 1.0 | 1.1 | 34 |
| 801295 | 1.8 | 1.4* | 1.4* | 1.0* | 0.9* | 35 |
| 801296 | 7.0 | N.D. | N.D. | N.D. | N.D. | 36 |
| 801297 | 3.5 | 1.0* | 1.0* | 0.9* | 0.8* | 37 |
| 801307 | 5.3 | 1.2* | 0.9* | 1.1* | 0.8* | 41 |
| 801308 | 5.3 | 1.2* | 1.2* | 0.9* | 1.1* | 42 |
| 801309 | 7.0 | N.D. | N.D. | N.D. | N.D. | 43 |
| 801310 | 1.8 | 1.2* | 1.2* | 1.0* | 1.0* | 44 |
| 801311 | 7.0 | N.D. | N.D. | N.D. | N.D. | 41 |
| 801312 | 0.0 | 2.0 | 1.3 | 1.0 | 1.4 | 42 |
| 801313 | 3.5 | 1.7* | 1.1* | 0.9* | 0.9* | 43 |
| 801314 | 0.0 | 1.9 | 1.2 | 1.0 | 2.9 | 44 |
| 801315 | 1.8 | 1.4* | 1.3* | 1.0* | 1.1* | 36 |
| 801316 | 0.0 | 1.5 | 1.4 | 1.0 | 1.2 | 37 |
| 801298 | 3.5 | 1.4* | 1.0* | 1.1* | 1.3* | 38 |
| 801299 | 5.3 | 1.2* | 1.2* | 1.0* | 1.0* | 39 |
| 801300 | 3.5 | 1.2* | 1.1* | 0.9* | 1.0* | 40 |
| 801301 | 7.0 | N.D. | N.D. | N.D. | N.D. | 38 |
| 801302 | 5.3 | 1.0* | 1.1* | 0.8* | 0.8* | 39 |
| 801303 | 1.8 | 1.1* | 1.0* | 1.0* | 1.1* | 40 |
| 801304 | 4.8 | 14.3* | 5.4* | 2.2* | 3.5* | 38 |
| 801305 | 5.3 | 3.6* | 1.7* | 1.6* | 1.6* | 39 |
| 801306 | 0.0 | 4.7 | 1.8 | 1.8 | 1.8 | 40 |
| 806673 | 0.0 | 1.1 | 1.0 | 1.0 | 9.1 | 49 |
| 806674 | 0.0 | 1.0 | 1.0 | 0.8 | 8.2 | 50 |
| 806675 | 0.0 | 1.0 | 1.0 | 0.8 | 10.3 | 51 |
| 806676 | 0.0 | 1.0 | 1.0 | 0.8 | 1.5 | 49 |
| 806677 | 0.0 | 0.9 | 1.0 | 0.9 | 1.5 | 50 |
| 806678 | 0.0 | 1.0 | 0.9 | 1.1 | 1.2 | 51 |
| 806679 | 0.0 | 1.2 | 1.1 | 1.1 | 1.3 | 49 |
| 806680 | 0.0 | 1.0 | 1.1 | 0.8 | 1.0 | 50 |
| 806681 | 0.0 | 1.0 | 1.0 | 0.9 | 1.4 | 51 |
| 806682 | 1.8 | 1.4* | 1.2* | 1.0* | 1.2* | 49 |
| 806683 | 0.0 | 1.2 | 1.2 | 0.9 | 1.2 | 50 |
| 806684 | 0.0 | 1.2 | 1.1 | 0.9 | 2.0 | 51 |
| 806685 | 0.0 | 1.0 | 0.9 | 0.8 | 1.5 | 52 |
| 806686 | 0.0 | 0.9 | 0.9 | 0.8 | 1.1 | 53 |
| 806687 | 0.0 | 1.0 | 1.0 | 0.8 | 1.0 | 54 |
| 806688 | 1.8 | 1.1* | 1.0* | 0.8* | 1.8* | 55 |
| 806689 | 0.0 | 1.1 | 1.0 | 0.8 | 1.3 | 52 |
| 806690 | 0.0 | 1.0 | 1.1 | 0.9 | 1.1 | 53 |
| 806691 | 5.3 | N.D. | N.D. | N.D. | N.D. | 54 |
| 802459 | 0.0 | 0.9 | 0.9 | 0.9 | 1.2 | 21 |
| 802460 | 5.3 | 1.1* | 1.1* | 1.0* | 1.4* | 45 |
| 802461 | 3.5 | 1.4* | 1.4* | 0.9* | 0.9* | 46 |
| 802462 | 3.5 | 0.8* | 0.9* | 0.9* | 1.1* | 21 |
| 802463 | 7.0 | N.D. | N.D. | N.D. | N.D. | 45 |
| 802464 | 1.8 | 1.4* | 1.2* | 1.5* | 1.4* | 46 |
| 802465 | 0.0 | 0.9 | 1.1 | 1.1 | 1.6 | 21 |
| 802466 | 1.8 | 1.0* | 1.0* | 1.0* | 1.4* | 45 |
| 802467 | 1.3 | 4.9 | 2.4 | 2.7 | 2.8 | 46 |
| 802468 | 0.0 | 1.4 | 1.3 | 1.2 | 2.2 | 21 |
| 802469 | 0.0 | 1.0 | 1.0 | 1.0 | 1.2 | 45 |
| 802470 | 1.5 | 3.2 | 3.4 | 2.6 | 3.4 | 46 |
| 802471 | 0.0 | 0.9 | 0.9 | 0.9 | 1.2 | 47 |
| 802472 | 3.5 | 1.6* | 1.4* | 0.9* | 1.5* | 48 |
| 802473 | 0.0 | 1.0 | 0.9 | 0.9 | 1.3 | 47 |
| 802474 | 1.8 | 1.3* | 1.2* | 1.0* | 1.8* | 48 |
| 802475 | 7.0 | N.D. | N.D. | N.D. | N.D. | 47 |
| 802476 | 1.8 | 1* | 1.2* | 0.8* | 1.8* | 48 |
| 802477 | 0.0 | 1.9 | 1.7 | 1.3 | 2.1 | 47 |
| 802478 | 3.5 | 1.4* | 1.1* | 1.1* | 1.3* | 48 |

Example 13: Tolerability of Antisense Oligonucleotides Targeting Human C9Orf72 in Rats Sprague Dawley rats were separated into groups of 4 or 6 rats. Each rat in each group of rats was administered a single 3 mg intrathecal (IT) dose of the oligonucleotide indicated in the table below. At 3 hours and at 8 weeks following the IT dose, the movement of 7 different parts of the body was evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a sub-score of 0 if the body part was moving or 1 if the body part was paralyzed. After each of the 7 body parts were evaluated, the sub-scores were summed for each rat and then averaged for each group. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Saline treated rats generally receive a score of 0. A score of at the top end of the range would be suggestive of acute toxicity. Results are presented in the table below as the average score for each treatment group.

Animals were sacrificed at 8 weeks. The cortex and spinal cord were collected from each animal, and RT-PCR was performed. Expression levels of AIF1 were determined as a measure of inflammation. Expression levels of (GFAP) were also determined as a measure of glial cell activation. An asterisk indicates that the corresponding result is the average of 2-3 mice. Results were normalized to Gapdh and are presented relative to PBS control (1.0) in the table below.

TABLE 16

Tolerability of antisense oligonucleotides targeting C9Orf72 in rats

| ISIS No. | Score 3 hours after injection | Score 8 weeks after injection | AIF1 (spinal cord) | AIF1 (cortex) | GFAP (spinal cord) | GFAP (cortex) | SEQ ID NO. |
|---|---|---|---|---|---|---|---|
| 801287 | 2.5 | 0.0 | 1.9 | 1.2 | 1.3 | 1.3 | 33 |
| 801288 | 4.0 | 3.5 | 1.3* | 1.3* | 1.2* | 1.3* | 34 |
| 806676 | 2.0 | 1.8 | 1.6* | 1.5* | 1.3* | 2.5* | 49 |
| 806679 | 1.2 | 0.0 | 1.4 | 1.3 | 1.3 | 1.8 | 49 |
| 806680 | 2.0 | 0.3 | 1.4 | 1.4 | 1.3 | 1.3 | 50 |
| 806690 | 1.3 | 0.0 | 1.5 | 1.4 | 1.3 | 2.0 | 53 |
| 802459 | 2.0 | 0.0 | 1.4 | 1.2 | 1.5 | 1.5 | 21 |
| 802473 | 2.0 | 2.3 | 1.8* | 1.6* | 1.7* | 1.6* | 47 |

Example 14: Tolerability of Antisense Oligonucleotides Targeting Human C9ORF72 in Non-Human Primates Female cynomolgus monkeys (2-6 kg) were given 3 doses of 35 mg of antisense oligonucleotide on days 1, 14, and 28 via intrathecal bolus injection (1 mL slow bolus followed by 0.25 mL flush). Each treatment group contained four monkeys. Two weeks after the final dose, animals were sacrificed and RT-PCR was performed on various CNS tissues. Expression levels of AIF1 were determined as a measure of inflammation and expression levels of GFAP were determined as a measure of glial cell activation. Results were normalized to GADPH and are presented relative to PBS control (1.0) in the table below for ISIS No. 801287, 802459, and 806679.

TABLE 17

Tolerability of antisense oligonucleotides targeting C9ORF72 in cynomolgus monkeys

| | AIF1 | | | GFAP | | |
|---|---|---|---|---|---|---|
| Brain Region | 801287 | 802459 | 806679 | 801287 | 802459 | 806679 |
| Cervical spinal cord | 1.0 | 0.9 | 0.9 | 1.1 | 1.0 | 1.1 |

TABLE 17-continued

Tolerability of antisense oligonucleotides targeting C9ORF72 in cynomolgus monkeys

| | AIF1 | | | GFAP | | |
|---|---|---|---|---|---|---|
| Brain Region | 801287 | 802459 | 806679 | 801287 | 802459 | 806679 |
| Thoracic spinal cord | 1.1 | 0.9 | 0.9 | 1.2 | 1.2 | 1.2 |
| Temporal cortex | 1.0 | 1.0 | 1.5 | 1.2 | 1.1 | 1.7 |
| Motor cortex | 1.0 | 1.0 | 1.2 | 1.2 | 0.7 | 1.3 |
| Lumbar spinal cord | 1.2 | 0.9 | 0.9 | 1.3 | 0.9 | 1.1 |
| Hippocampus | 1.0 | 1.0 | 1.3 | 1.9 | 1.9 | 1.7 |
| Frontal cortex | 1.3 | 0.9 | 1.3 | 1.0 | 0.7 | 1.3 |

What is claimed is:
1. A modified oligonucleotide according to the following formula:
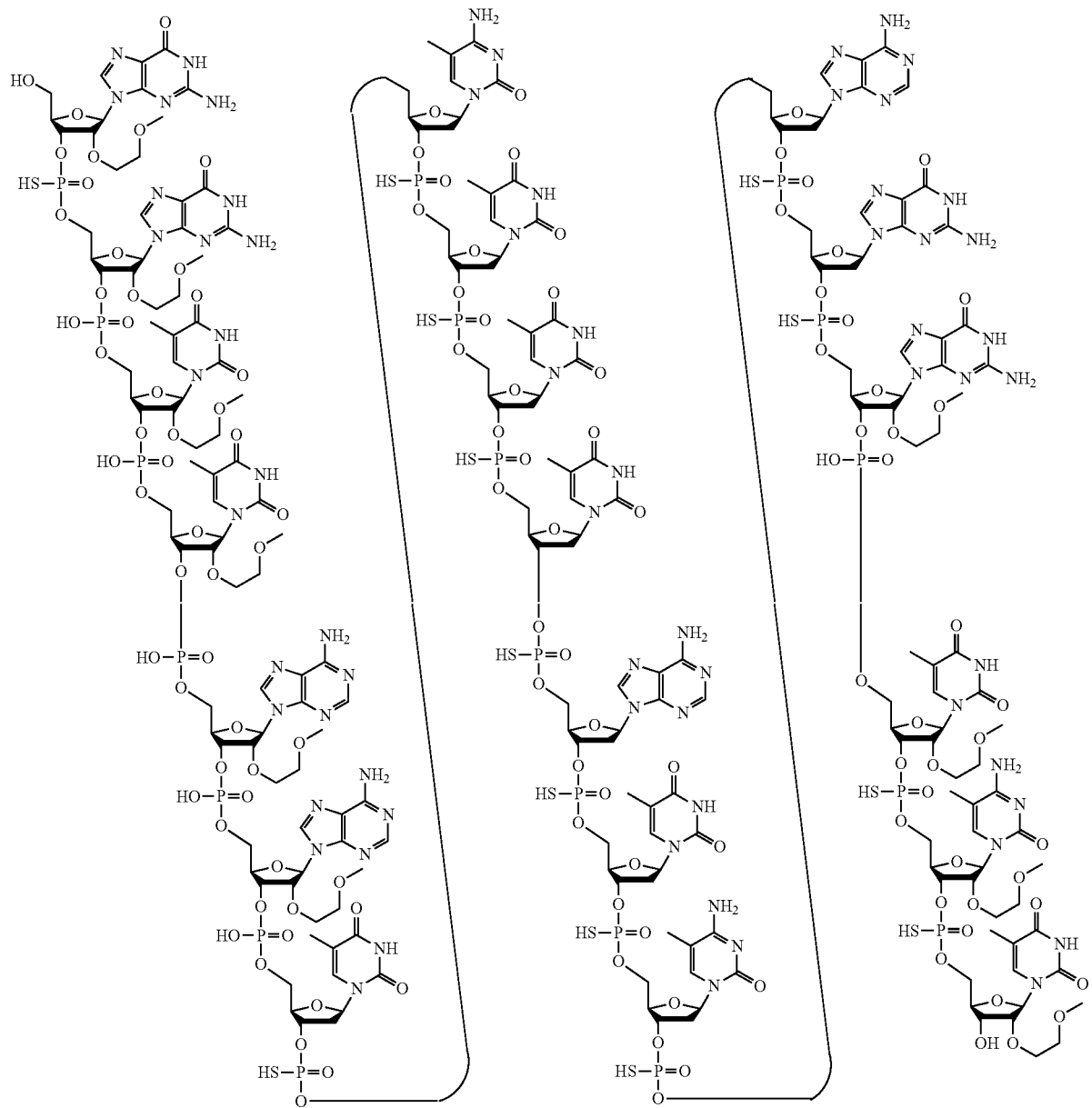
(SEQ ID NO: 49)
or a salt thereof.

2. The modified oligonucleotide of claim 1, which is a sodium salt of the formula.

3. A pharmaceutical composition comprising the modified oligonucleotide of claim 1 and a pharmaceutically acceptable diluent or carrier.

4. The pharmaceutical composition of claim 3, wherein the pharmaceutically acceptable diluent is phosphate-buffered saline (PBS).

5. The pharmaceutical composition of claim 3, wherein the pharmaceutical composition consists essentially of the modified oligonucleotide and phosphate-buffered saline (PBS).

6. A pharmaceutical composition comprising the modified oligonucleotide of claim 2 and a pharmaceutically acceptable diluent or carrier.

7. The pharmaceutical composition of claim 6, wherein the pharmaceutically acceptable diluent is phosphate-buffered saline (PBS).

8. The pharmaceutical composition of claim 6, wherein the pharmaceutical composition consists essentially of the modified oligonucleotide and phosphate-buffered saline (PBS).

9. A modified oligonucleotide according to the following formula:

(SEQ ID NO: 49)

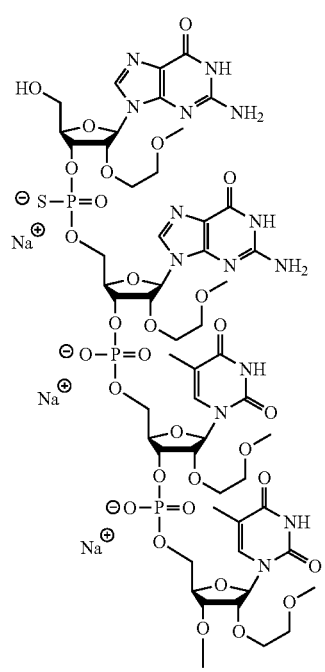
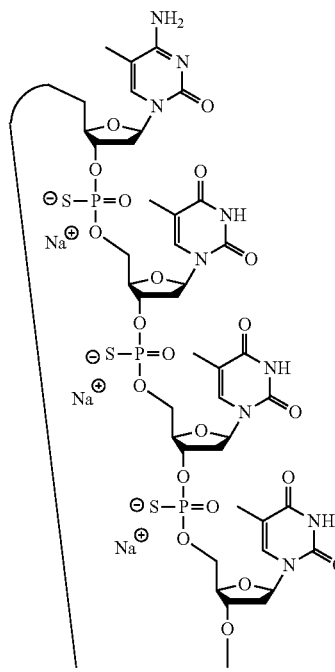
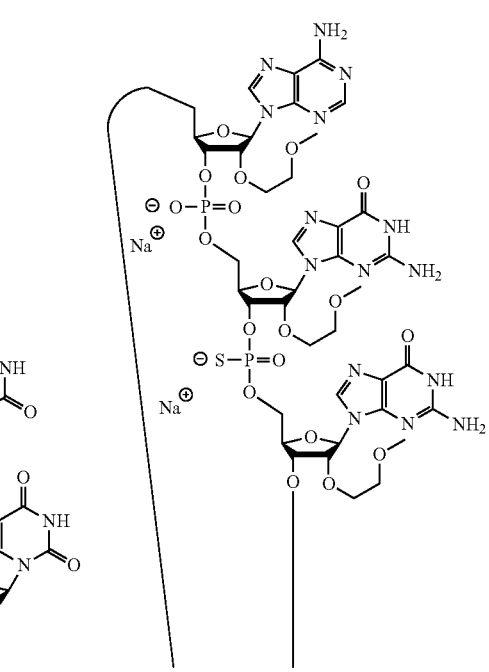
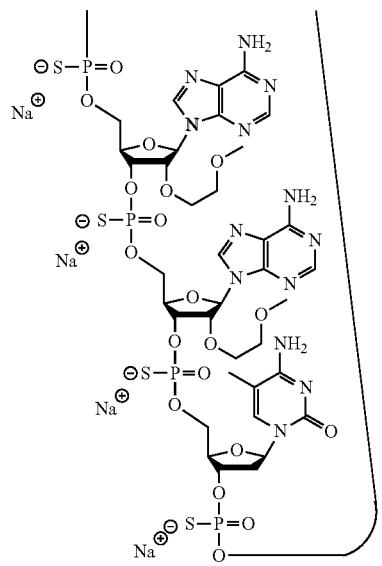
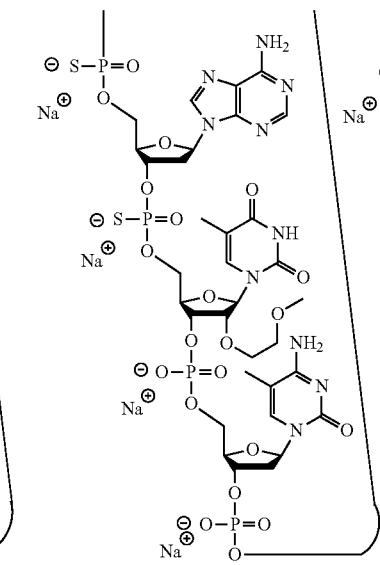

10. A pharmaceutical composition comprising the modified oligonucleotide of claim 9 and a pharmaceutically acceptable diluent or carrier.

11. The pharmaceutical composition of claim 10, wherein the pharmaceutically acceptable diluent is phosphate-buffered saline (PBS).

12. The pharmaceutical composition of claim 10, wherein the pharmaceutical composition consists essentially of the modified oligonucleotide and phosphate-buffered saline (PBS).

13. A compound comprising a modified oligonucleotide, wherein the modified oligonucleotide is a gapmer consisting of a 5' wing segment, a central gap segment, and a 3' wing segment, wherein:
 the 5' wing segment consists of six 2'-O-methoxyethyl nucleosides,
 the central gap segment consists of ten β-D-deoxyribonucleosides, and
 the 3' wing segment consists of four 2'-O-methoxyethyl nucleosides;
wherein the modified oligonucleotide has the nucleobase sequence 5'-GGTTAATCTTTATCAGGTCT-3' (SEQ ID NO: 49), wherein each cytosine is a 5-methylcytosine; and wherein the internucleoside linkages of the modified oligonucleotide are, from 5' to 3', sooooosssssssssoss, wherein each s is a phosphorothioate linkage and each o is a phosphodiester linkage.

14. The compound of claim 13, comprising the modified oligonucleotide covalently linked to a conjugate group.

15. A pharmaceutical composition comprising the compound of claim 13 and a pharmaceutically acceptable diluent or carrier.

16. The pharmaceutical composition of claim 15, wherein the pharmaceutically acceptable diluent is phosphate-buffered saline (PBS).

17. The pharmaceutical composition of claim 15, wherein the pharmaceutical composition consists essentially of the compound and phosphate-buffered saline (PBS).

18. A pharmaceutical composition comprising the compound of claim 14 and a pharmaceutically acceptable diluent or carrier.

19. The pharmaceutical composition of claim 18, wherein the pharmaceutically acceptable diluent is phosphate-buffered saline (PBS).

20. The pharmaceutical composition of claim 18, wherein the pharmaceutical composition consists essentially of the compound and phosphate-buffered saline (PBS).

* * * * *

SEQUENCE LISTING

<160> NUMBER OF SEQ ID NOS: 60

<210> SEQ ID NO 1
<211> LENGTH: 3339
<212> TYPE: DNA
<213> ORGANISM: homo sapiens

<400> SEQUENCE: 1

```
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120
ggggcggggt ctagcaagag caggtgtggg tttaggagat atctccggag catttggata    180
atgtgacagt tggaatgcag tgatgtcgac tctttgccca ccgccatctc cagctgttgc    240
caagacagag attgctttaa gtggcaaatc acctttatta gcagctactt ttgcttactg    300
ggacaatatt cttggtccta gagtaaggca catttgggct ccaaagacag aacaggtact   360
tctcagtgat ggagaaataa cttttcttgc caaccacact ctaaatggag aaatccttcg    420
aaatgcagag agtggtgcta tagatgtaaa gttttttgtc ttgtctgaaa agggagtgat    480
tattgtttca ttaatctttg atggaaactg gaatgggat cgcagcacat atggactatc    540
```

-continued

```
aattatactt ccacagacag aacttagttt ctacctccca cttcatagag tgtgtgttga    600
tagattaaca catataatcc ggaaaggaag aatatggatg cataaggaaa gacaagaaaa    660
tgtccagaag attatcttag aaggcacaga gagaatggaa gatcagggtc agagtattat    720
tccaatgctt actggagaag tgattcctgt aatggaactg ctttcatcta tgaaatcaca    780
cagtgttcct gaagaaatag atatagctga tacagtactc aatgatgatg atattggtga    840
cagctgtcat gaaggctttc ttctcaatgc catcagctca cacttgcaaa cctgtggctg    900
ttccgttgta gtaggtagca gtgcagagaa agtaaataag atagtcagaa cattatgcct    960
ttttctgact ccagcagaga gaaaatgctc caggttatgt gaagcagaat catcatttaa   1020
atatgagtca gggctctttg tacaaggcct gctaaaggat tcaactggaa gctttgtgct   1080
gcctttccgg caagtcatgt atgctccata tcccaccaca cacatagatg tggatgtcaa   1140
tactgtgaag cagatgccac cctgtcatga acatatttat aatcagcgta gatacatgag   1200
atccgagctg acagccttct ggagagccac ttcagaagaa gacatggctc aggatacgat   1260
catctacact gacgaaagct ttactcctga tttgaatatt tttcaagatg tcttacacag   1320
agacactcta gtgaaagcct tcctggatca ggtctttcag ctgaaacctg gcttatctct   1380
cagaagtact ttccttgcac agtttctact tgtccttcac agaaaagcct tgacactaat   1440
aaaatatata gaagacgata cgcagaaggg aaaaaagccc tttaaatctc ttcggaacct   1500
gaagatagac cttgatttaa cagcagaggg cgatcttaac ataataatgg ctctggctga   1560
gaaaattaaa ccaggcctac actctttta ctttggaaga cctttctaca ctagtgtgca   1620
agaacgagat gttctaatga ctttttaaat gtgtaactta ataagcctat tccatcacaa   1680
tcatgatcgc tggtaaagta gctcagtggt gtggggaaac gttcccctgg atcatactcc   1740
agaattctgc tctcagcaat tgcagttaag taagttacac tacagttctc acaagagcct   1800
gtgaggggat gtcaggtgca tcattacatt gggtgtctct tttcctagat ttatgctttt   1860
gggatacaga cctatgttta caatataata aatattattg ctatcttta aagatataat   1920 aataggatgt aaacttgacc acaactactg ttttttgaa atacatgatt catggtttac   1980
atgtgtcaag gtgaaatctg agttggcttt tacagatagt tgactttcta tcttttggca   2040
ttctttggtg tgtagaatta ctgtaatact tctgcaatca actgaaaact agagccttta   2100
aatgatttca attccacaga aagaaagtga gcttgaacat aggatgagct ttagaaagaa   2160
aattgatcaa gcagatgttt aattggaatt gattattaga tcctactttg tggatttagt   2220
ccctgggatt cagtctgtag aaatgtctaa tagttctcta tagtccttgt tcctggtgaa   2280
ccacagttag ggtgttttgt ttattttatt gttcttgcta ttgttgatat tctatgtagt   2340
tgagctctgt aaaaggaaat tgtattttat gttttagtaa ttgttgccaa cttttttaaat  2400 taattttcat tattttgag ccaaattgaa atgtgcacct cctgtgcctt ttttctcctt   2460
agaaaatcta attacttgga acaagttcag atttcactgg tcagtcattt tcatcttgtt   2520
ttcttcttgc taagtcttac catgtacctg ctttggcaat cattgcaact ctgagattat   2580
aaaatgcctt agagaatata ctaactaata agatcttttt ttcagaaaca gaaaatagtt   2640
ccttgagtac ttccttcttg catttctgcc tatgttttg aagttgttgc tgtttgcctg    2700
caataggcta taaggaatag caggagaaat tttactgaag tgctgttttc ctaggtgcta   2760
ctttggcaga gctaagttat cttttgtttt cttaatgcgt ttggaccatt tgctggcta    2820 taaaataact gattaatata attctaacac aatgttgaca ttgtagttac acaaacacaa   2880
ataaatattt tatttaaaat tctggaagta atataaaagg gaaaatatat ttataagaaa   2940
```

| | |
|---|---|
| gggataaagg taatagagcc cttctgcccc ccacccacca aatttacaca acaaaatgac | 3000 |
| atgttcgaat gtgaaaggtc ataatagctt tcccatcatg aatcagaaag atgtggacag | 3060 |
| cttgatgttt tagacaacca ctgaactaga tgactgttgt actgtagctc agtcatttaa | 3120 |
| aaaatatata aatactacct tgtagtgtcc catactgtgt tttttacatg gtagattctt | 3180 |
| atttaagtgc taactggtta ttttctttgg ctggtttatt gtactgttat acagaatgta | 3240 |
| agttgtacag tgaaataagt tattaaagca tgtgtaaaca ttgttatata tcttttctcc | 3300 |
| taaatggaga attttgaata aaatatattt gaaattttg | 3339 |

<210> SEQ ID NO 2
<211> LENGTH: 30001
<212> TYPE: DNA
<213> ORGANISM: homo sapiens

<400> SEQUENCE: 2

| | |
|---|---|
| caaagaaaag ggggaggttt tgttaaaaaa gagaaatgtt acatagtgct ctttgagaaa | 60 |
| attcattggc actattaagg atctgaggag ctggtgagtc tcaactggtg agtgatggtg | 120 |
| gtagataaaa ttagagctgc agcaggtcat tttagcaact attagataaa actggtctca | 180 |
| ggtcacaacg ggcagttgca gcagctggac ttggagagaa ttacactgtg ggagcagtgt | 240 |
| catttgtcct aagtgctttt ctacccccta cccccactat tttagttggg tataaaaaga | 300 |
| atgacccaat ttgtatgatc aactttcaca aagcatagaa cagtaggaaa agggtctgtt | 360 |
| tctgcagaag gtgtagacgt tgagagccat tttgtgtatt tattcctccc tttcttcctc | 420 |
| ggtgaatgat taaaacgttc tgtgtgattt ttagtgatga aaaagattaa atgctactca | 480 |
| ctgtagtaag tgccatctca cacttgcaga tcaaaaggca cacagtttaa aaaacctttg | 540 |
| ttttttttaca catctgagtg gtgtaaatgc tactcatctg tagtaagtgg aatctataca | 600 |
| cctgcagacc aaaagacgca aggtttcaaa aatctttgtg ttttttacac atcaaacaga | 660 |
| atggtacgtt tttcaaaagt taaaaaaaaa caactcatcc acatattgca actagcaaaa | 720 |
| atgacattcc ccagtgtgaa aatcatgctt gagagaattc ttacatgtaa aggcaaaatt | 780 |
| gcgatgactt tgcaggggac cgtgggattc ccgcccgcag tgccggagct gtcccctacc | 840 |
| agggtttgca gtggagtttt gaatgcactt aacagtgtct tacggtaaaa acaaaatttc | 900 |
| atccaccaat tatgtgttga gcgcccactg cctaccaagc acaaacaaaa ccattcaaaa | 960 |
| ccacgaaatc gtcttcactt tctccagatc cagcagcctc ccctattaag gttcgcacac | 1020 |
| gctattgcgc caacgctcct ccagagcggg tcttaagata aagaacagg acaagttgcc | 1080 |
| ccgcccccatt tcgctagcct cgtgagaaaa cgtcatcgca catagaaaac agacagacgt | 1140 |
| aacctacggt gtcccgctag aaagagagg tgcgtcaaac agcgacaagt tccgcccacg | 1200 |
| taaaagatga cgcttggtgt gtcagccgtc cctgctgccc ggttgcttct cttttggggg | 1260 |
| cggggtctag caagagcagg tgtgggttta ggaggtgtgt gttttttgttt ttcccaccct | 1320 |
| ctctccccac tacttgctct cacagtactc gctgagggtg aacaagaaaa gacctgataa | 1380 |
| agattaacca gaagaaaaca aggagggaaa caaccgcagc ctgtagcaag ctctggaact | 1440 |
| caggagtcgc gcgctagggg ccggggccgg ggccggggcg tggtcgggc gggcccgggg | 1500 |
| gcgggcccgg ggcggggctg cggttgcggt gcctgcgccc gcggcggcgg aggcgcaggc | 1560 |
| ggtggcgagt gggtgagtga ggaggcggca tcctggcggg tggctgtttg gggttcggct | 1620 |
| gccgggaaga ggcgcgggta gaagcggggg ctctcctcag agctcgacgc attttttactt | 1680 |
| tccctctcat ttctctgacc gaagctgggt gtcgggcttt cgcctctagc gactggtgga | 1740 |

```
attgcctgca tccgggcccc gggcttcccg gcggcggcgg cggcggcggc ggcgcaggga    1800
caagggatgg ggatctggcc tcttccttgc tttcccgccc tcagtacccg agctgtctcc    1860
ttcccggga cccgctggga gcgctgccgc tgcgggctcg agaaaaggga gcctcgggta    1920
ctgagaggcc tcgcctgggg gaaggccgga gggtgggcgg cgcgcggctt ctgcggacca    1980
agtcggggtt cgctaggaac ccgagacggt ccctgccggc gaggagatca tgcgggatga    2040
gatggggtg tggagacgcc tgcacaattt cagcccaagc ttctagagag tggtgatgac    2100
ttgcatatga gggcagcaat gcaagtcggt gtgctcccca ttctgtggga catgacctgg    2160
ttgcttcaca gctccgagat gacacagact tgcttaaagg aagtgactat tgtgacttgg    2220
gcatcacttg actgatggta atcagttgtc taaagaagtg cacagattac atgtccgtgt    2280
gctcattggg tctatctggc cgcgttgaac accaccaggc tttgtattca gaaacaggag    2340
ggaggtcctg cactttccca ggaggggtgg ccctttcaga tgcaatcgag attgttaggc    2400
tctgggagag tagttgcctg gttgtggcag ttggtaaatt tctattcaaa cagttgccat    2460
gcaccagttg ttcacaacaa gggtacgtaa tctgtctggc attacttcta cttttgtaca    2520
aaggatcaaa aaaaaaaag atactgttaa gatatgattt ttctcagact ttgggaaact    2580
tttaacataa tctgtgaata tcacagaaac aagactatca tataggggat attaataacc    2640
tggagtcaga atacttgaaa tacggtgtca tttgacacgg gcattgttgt caccacctct    2700
gccaaggcct gccactttag gaaaaccctg aatcagttgg aaactgctac atgctgatag    2760
tacatctgaa acaagaacga gagtaattac cacattccag attgttcact aagccagcat    2820
ttacctgctc caggaaaaaa ttacaagcac cttatgaagt tgataaaata ttttgtttgg    2880
ctatgttggc actccacaat ttgctttcag agaaacaaag taaaccaagg aggacttctg    2940
tttttcaagt ctgccctcgg gttctattct acgttaatta gatagttccc aggaggacta    3000
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctctttgggc tgggagaaaa taaacagcat ggttacaagt    3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttgggaggct gaggcaggag ggtcatttga gcccaagagt tgaagttac cgagagctat    3480
gatcctgcca gtgcattcca gcctggatga caaaacgaga ccctgtctct aaaaaacaag    3540
aagtgagggc tttatgattg tagaattttc actacaatag cagtggacca accacctttc    3600
taaataccaa tcagggaaga gatggttgat ttttaacag acgtttaaag aaaaagcaaa    3660
acctcaaact tagcactcta ctaacagttt tagcagatgt taattaatgt aatcatgtct    3720
gcatgtatgg gattatttcc agaaagtgta ttgggaaacc tctcatgaac cctgtgagca    3780
agccaccgtc tcactcaatt tgaatcttgg cttccctcaa aagactggct aatgtttggt    3840
aactctctga agtagacagc actacatgta cgtaagatag gtacataaac aactattggt    3900
tttgagctga ttttttttcag ctgcatttgc atgtatggat ttttctcacc aaagacgatg    3960
acttcaagta ttagtaaaat aattgtacag ctctcctgat tatacttctc tgtgacattt    4020
catttcccag gctatttctt ttggtaggat ttaaaactaa gcaattcagt atgatctttg    4080
```

```
tccttcattt tctttcttat tcttttgtt tgtttgtttg tttgtttttt tcttgaggca    4140
gagtctctct ctgtcgccca ggctggagtg cagtggcgcc atctcagctc attgcaacct    4200
ctgccacctc cgggttcaag agattctcct gcctcagcct cccgagtagc tgggattaca    4260
ggtgtccacc accacacccg ctaattttt tgtattttta gtagaggtgg ggtttcacca    4320
tgttggccag gctggtcttg agctcctgac ctcaggtgat ccacctgcct cggcctacca    4380
aagagctggg ataacaggtg tgacccacca tgcccggccc attttttttt tcttattctg    4440
ttaggagtga gagtgtaact agcagtataa tagttcaatt ttcacaacgt ggtaaaagtt    4500
tccctataat tcaatcagat tttgctccag ggttcagttc tgttttagga aatacttta    4560
ttttcagttt aatgatgaaa tattagagtt gtaatattgc ctttatgatt atccaccttt    4620
ttaacctaaa agaatgaaag aaaaatatgt ttgcaatata atttatggt tgtatgttaa    4680
cttaattcat tatgttggcc tccagtttgc tgttgttagt tatgacagca gtagtgtcat    4740
taccatttca attcagatta cattcctata tttgatcatt gtaaactgac tgcttacatt    4800
gtattaaaaa cagtggatat tttaaagaag ctgtacggct tatatctagt gctgtctctt    4860
aagactatta aattgataca acatatttaa aagtaaatat taccctaaatg aatttttgaa    4920
attacaaata cacgtgttaa aactgtcgtt gtgttcaacc atttctgtac atacttagag    4980
ttaactgttt tgccaggctc tgtatgccta ctcataatat gataaaagca ctcatctaat    5040
gctctgtaaa tagaagtcag tgcttttccat cagactgaac tctcttgaca agatgtggat    5100
gaaattcttt aagtaaaatt gtttactttg tcatacattt acagatcaaa tgttagctcc    5160
caaagcaatc atatggcaaa gataggtata tcatagtttg cctattagct gctttgtatt    5220
gctattatta taaatagact tcacagtttt agacttgctt aggtgaaatt gcaattcttt    5280
ttactttcag tcttagataa caagtcttca attatagtac aatcacacat tgcttaggaa    5340
tgcatcatta ggcgattttg tcattatgca aacatcatag agtgtactta cacaaaccta    5400
gatagtatag cctttatgta cctaggccgt atggtatagt ctgttgctcc taggccacaa    5460
acctgtacaa ctgttactgt actgaatact atagacagtt gtaacacagt ggtaaatatt    5520
tatctaaata tatgcaaaca gagaaaaggt acagtaaaag tatggtataa aagataatgg    5580
tatacctgtg taggccactt accacgaatg gagcttgcag gactagaagt tgctctgggt    5640
gagtcagtga gtgagtggtg aattaatgtg aaggcctaga acactgtaca ccactgtaga    5700
ctataaacac agtacgctga agctacacca aatttatctt aacagttttt cttcaataaa    5760
aaattataac ttttaacctt tgtaaacttt ttaattttt aacttttaaa atacttagct    5820
tgaaacacaa atacattgta tagctataca aaaatatttt ttctttgtat ccttattcta    5880
gaagcttttt tctattttct attttaaatt tttttttta cttgttagtc gttttttgtta    5940
aaaactaaaa cacacacact ttcacctagg catagacagg attaggatca tcagtatcac    6000
tcccttccac ctcactgcct tccacctcca catcttgtcc cactggaagg tttttagggg    6060
caataacaca catgtagctg tcacctatga taacagtgct ttctgttgaa tacctcctga    6120
aggacttgcc tgaggctgtt ttacatttaa cttaaaaaaa aaaaagtag aaggagtgca    6180
ctctaaaata acaataaaag gcatagtata gtgaatacat aaaccagcaa tgtagtagtt    6240
tattatcaag tgttgtacac tgtaataatt gtatgtgcta actttaaat aacttgcaaa    6300
atagtactaa gaccttatga tggttacagt gtcactaagg caatagcata ttttcaggtc    6360
cattgtaatc taatgggact accatcatat atgcagtcta ccattgactg aaacgttaca    6420
tggcacataa ctgtatttgc aagaatgatt tgttttacat taatatcaca taggatgtac    6480
```

```
cttttttagag tggtatgttt atgtggatta agatgtacaa gttgagcaag gggaccaaga    6540
gccctgggtt ctgtcttgga tgtgagcgtt tatgttcttc tcctcatgtc tgttttctca    6600
ttaaattcaa aggcttgaac gggccctatt tagcccttct gttttctacg tgttctaaat    6660
aactaaagct tttaaattct agccatttag tgtagaactc tctttgcagt gatgaaatgc    6720
tgtattggtt tcttggctag catattaaat attttttatct tgtcttgat acttcaatgt    6780 cgttttaaac atcaggatcg ggcttcagta ttctcataac cagagagttc actgaggata    6840
caggactgtt tgcccatttt ttgttatggc tccagacttg tggtatttcc atgtcttttt    6900
tttttttttt tttttgacc ttttagcggc tttaaagtat ttctgttgtt aggtgttgta    6960 ttactttct aagattactt aacaaagcac cacaaactga gtggctttaa acaacagcaa    7020
tttattctct cacaattcta gaagctagaa gtccgaaatc aaagtgttga caggggcatg    7080
atcttcaaga gagaagactc tttccttgcc tcttcctggc ttctggtggt taccagcaat    7140
cctgagtgtt cctttcttgc cttgtagttt caacaatcca gtatctgcct tttgtcttca    7200
catggctgtc taccatttgt ctctgtgtct ccaaatctct ctccttataa acacagcagt    7260
tattggatta ggccccactc taatccagta tgaccccatt ttaacatgat tacacttatt    7320
tctagataag gtcacattca cgtacaccaa gggttaggaa ttgaacatat ctttttgggg    7380
gacacaattc aacccacaag tgtcagtctc tagctgagcc tttcccttcc tgtttttctc    7440 cttttagtt gctatgggtt aggggccaaa tctccagtca tactagaatt gcacatggac    7500
tggatatttg gaatactgc gggtctattc tatgagcttt agtatgtaac atttaatatc    7560
agtgtaaaga agccctttt taagttattt ctttgaattt ctaaatgtat gccctgaata    7620
taagtaacaa gttaccatgt cttgtaaaat gatcatatca acaaacattt aatgtgcacc    7680
tactgtgcta gttgaatgtc tttatcctga taggagataa caggattcca catctttgac    7740
ttaagaggac aaaccaaata tgtctaaatc atttggggtt ttgatggata tctttaaatt    7800
gctgaaccta atcattggtt tcatatgtca ttgtttagat atctccggag catttggata    7860
atgtgacagt tggaatgcag tgatgtcgac tctttgccca ccgccatctc cagctgttgc    7920
caagacagag attgctttaa gtggcaaatc acctttatta gcagctactt ttgcttactg    7980
ggacaatatt cttggtccta gagtaaggca catttgggct ccaaagacag aacaggtact    8040
tctcagtgat ggagaaataa cttttcttgc caaccacact ctaaatggag aaatccttcg    8100
aaatgcagag agtggtgcta tagatgtaaa gttttttgtc ttgtctgaaa agggagtgat    8160
tattgtttca ttaatctttg atggaaactg gaatggggat cgcagcacat atggactatc    8220
aattatactt ccacagacag aacttagttt ctacctccca cttcatagag tgtgtgttga    8280
tagattaaca catataatcc ggaaaggaag aatatggatg cataaggtaa gtgattttc    8340 agcttattaa tcatgttaac ctatctgttg aaagcttatt ttctggtaca tataaatctt    8400
atttttttaa ttatatgcag tgaacatcaa acaataaatg ttatttattt tgcatttacc    8460
ctattagata caaatacatc tggtctgata cctgtcatct tcatattaac tgtggaaggt    8520
acgaaatggt agctccacat tatagatgaa aagctaaagc ttagacaaat aaagaaactt    8580
ttagaccctg gattcttctt gggagccttt gactctaata ccttttgttt ccctttcatt    8640
gcacaattct gtcttttgct tactactatg tgtaagtata acagttcaaa gtaatagttt    8700
cataagctgt tggtcatgta gcctttggtc tctttaacct ctttgccaag ttcccaggtt    8760
cataaaatga ggaggttgaa tggaatggtt cccaagagaa ttccttttaa tcttacagaa    8820
```

```
attattgttt tcctaaatcc tgtagttgaa tatataatgc tatttacatt tcagtatagt    8880
tttgatgtat ctaaagaaca cattgaattc tccttcctgt gttccagttt gatactaacc    8940
tgaaagtcca ttaagcatta ccagttttaa aaggcttttg cccaatagta aggaaaaata    9000
atatctttta aaagaataat tttttactat gtttgcaggc ttacttcctt ttttctcaca    9060
ttatgaaact cttaaaatca ggagaatctt ttaaacaaca tcataatgtt taatttgaaa    9120
agtgcaagtc attcttttcc ttttttgaaac tatgcagatg ttacattgac tgttttctgt    9180
gaagttatct tttttttcact gcagaataaa ggttgttttg attttatttt gtattgttta    9240
tgagaacatg catttgttgg gttaatttcc taccctgcc cccatttttt ccctaaagta    9300
gaaagtattt ttcttgtgaa ctaaattact acacaagaac atgtctattg aaaaataagc    9360
aagtatcaaa atgttgtggg ttgttttttt aaataaattt tctcttgctc aggaaagaca    9420
agaaaatgtc cagaagatta tcttagaagg cacagagaga atggaagatc aggtatatgc    9480
aaattgcata ctgtcaaatg ttttctcac agcatgtatc tgtataaggt tgatggctac    9540
atttgtcaag gccttggaga catacgaata agcctttaat ggagctttta tggaggtgta    9600
cagaataaac tggaggaaga tttccatatc ttaaacccaa agagttaaat cagtaaacaa    9660
aggaaaatag taattgcatc tacaaattaa tatttgctcc ctttttttt ctgtttgccc    9720
agaataaatt ttggataact tgttcatagt aaaaataaaa aaaattgtct ctgatatgtt    9780
ctttaaggta ctacttctcg aacctttccc tagaagtagc tgtaacagaa ggagagcata    9840
tgtacccctg aggtatctgt ctggggtgta ggcccaggtc cacacaatat ttcttctaag    9900
tcttatgttt tatcgttaag actcatgcaa tttacatttt attccataac tattttagta    9960
ttaaaatttg tcagtgatat ttcttaccct ctcctctagg aaaatgtgcc atgtttatcc    10020
cttggctttg aatgcccctc aggaacagac actaagagtt tgagaagcat ggttacaagg    10080
gtgtggcttc ccctgcggaa actaagtaca gactatttca ctgtaaagca gagaagttct    10140
tttgaaggag aatctccagt gaagaaagag ttcttcactt ttacttccat ttcctcttgt    10200
gggtgaccct caatgctcct tgtaaaactc caatatttta aacatggctg ttttgccttt    10260
ctttgcttct ttttagcatg aatgagacag atgatacttt aaaaaagtaa ttaaaaaaaa    10320
aaacttgtga aaatacatgg ccataataca gaacccaata caatgatctc ctttaccaaa    10380
ttgttatgtt tgtacttttg tagatagctt tccaattcag agacagttat tctgtgtaaa    10440
ggtctgactt aacaagaaaa gatttccctt tacccaaaga atcccagtcc ttatttgctg    10500
gtcaataagc agggtcccca ggaatggggt aactttcagc accctctaac ccactagtta    10560
ttagtagact aattaagtaa acttatcgca agttgaggaa acttagaacc aactaaaatt    10620
ctgcttttac tgggattttg ttttttcaaa ccagaaacct ttacttaagt tgactactat    10680
taatgaattt tggtctctct tttaagtgct cttcttaaaa atgttatctt actgctgaga    10740
agttcaagtt tgggaagtac aaggaggaat agaaacttaa gagattttct tttagagcct    10800
cttctgtatt tagccctgta ggatttttt tttttttttt tttttggtg ttgttgagct    10860
tcagtgaggc tattcattca cttatactga taatgtctga gatactgtga atgaaatact    10920
atgtatgctt aaacctaaga ggaaatattt tcccaaaatt attcttcccg aaaggagga    10980
gttgccttt gattgagttc ttgcaaatct cacaacgact ttattttgaa caatactgtt    11040
tggggatgat gcattagttt gaaacaactt cagttgtagc tgtcatctga taaaattgct    11100
tcacagggaa ggaaatttaa cacgatcta gtcattattc ttgttagatt gaatgtgtga    11160
attgtaattg taaacaggca tgataattat tactttaaaa actaaaaaca gtgaatagtt    11220
```

```
agttgtggag gttactaaag gatggttttt ttttaaataa aactttcagc attatgcaaa    11280
tgggcatatg gcttaggata aaacttccag aagtagcatc acatttaaat tctcaagcaa    11340
cttaataata tggggctctg aaaaactggt taaggttact ccaaaaatgg ccctgggtct    11400
gacaaagatt ctaacttaaa gatgcttatg aagactttga gtaaaatcat ttcataaaat    11460
aagtgaggaa aaacaactag tattaaattc atcttaaata atgtatgatt taaaaaatat    11520
gtttagctaa aaatgcatag tcatttgaca atttcattta tatctcaaaa aatttactta    11580
accaagttgg tcacaaaact gatgagactg gtggtggtag tgaataaatg agggaccatc    11640
catatttgag acactttaca tttgtgatgt gttatactga attttcagtt tgattctata    11700
gactacaaat ttcaaaatta caatttcaag atgtaataag tagtaatatc ttgaaatagc    11760
tctaaaggga atttttctgt tttattgatt cttaaaatat atgtgctgat tttgatttgc    11820
atttgggtag attatacttt tatgagtatg gaggttaggt attgattcaa gttttcctta    11880
cctatttggt aaggatttca aagtcttttt gtgcttggtt ttcctcattt ttaaaatga    11940 aatatattga tgacctttaa caaatttttt ttatctcaaa ttttaaagga gatcttttct    12000
aaaagaggca tgatgactta atcattgcat gtaacagtaa acgataaacc aatgattcca    12060
tactctctaa agaataaaag tgagctttag ggccgggcat ggtcagaaat ttgacaccaa    12120
cctggccaac atggcgaaac cccgtctcta ctaaaaatac aaaaatcagc cgggcatggt    12180
ggcggcacct atagtcccag ctacttggga ggatgagaca ggagagtcac ttgaacctgg    12240
gaggagaggt tgcagtgagc tgagatcacg ccattgcact ccagcctgag caatgaaagc    12300
aaaactccat ctcaaaaaaa aaaaagaaa agaaagaata aaagtgagct ttggattgca    12360
tataaatcct ttagacatgt agtagacttg tttgatactg tgtttgaaca aattacgaag    12420
tattttcatc aaagaatgtt attgtttgat gttatttta tttttttattg cccagcttct    12480 ctcatattac gtgatttct tcacttcatg tcactttatt gtgcagggtc agagtattat    12540
tccaatgctt actggagaag tgattcctgt aatggaactg ctttcatcta tgaaatcaca    12600
cagtgttcct gaagaaatag atgtaagttt aaatgagagc aattatacac tttatgagtt    12660 ttttgggggtt atagtattat tatgtatatt attaatattc taattttaat agtaaggact    12720
ttgtcataca tactattcac atacagtatt agccacttta gcaaataagc acacacaaaa    12780
tcctggattt tatggcaaaa cagaggcatt tttgatcagt gatgacaaaa ttaaattcat    12840
tttgtttatt tcattacttt tataattcct aaaagtggga ggatcccagc tcttatagga    12900
gcaattaata tttaatgtag tgtcttttga aacaaaactg tgtgccaaag tagtaaccat    12960
taatggaagt ttacttgtag tcacaaattt agtttcctta atcatttgtt gaggacgttt    13020
tgaatcacac actatgagtg ttaagagata cctttaggaa actattcttg ttgttttctg    13080
attttgtcat ttaggttagt ctcctgattc tgacagctca gaagaggaag ttgttcttgt    13140
aaaaattgtt taacctgctt gaccagcttt cacatttgtt cttctgaagt ttatggtagt    13200
gcacagagat tgttttttgg ggagtcttga ttctcggaaa tgaaggcagt gtgttatatt    13260
gaatccagac ttccgaaaac ttgtatatta aaagtgttat ttcaacacta tgttacagcc    13320
agactaattt ttttattttt tgatgcattt tagatagctg atacagtact caatgatgat    13380
gatattggtg acagctgtca tgaaggcttt cttctcaagt aagaattttt cttttcataa    13440
aagctggatg aagcagatac catcttatgc tcacctatga caagatttgg aagaaagaaa    13500
ataacagact gtctacttag attgttctag ggacattacg tatttgaact gttgcttaaa    13560
```

```
tttgtgttat ttttcactca ttatatttct atatatattt ggtgttattc catttgctat    13620
ttaaagaaac cgagtttcca tcccagacaa gaaatcatgg cccttgctt gattctggtt     13680 tcttgtttta cttctcatta aagctaacag aatcctttca tattaagttg tactgtagat    13740
gaacttaagt tatttaggcg tagaacaaaa ttattcatat ttatactgat cttttttccat   13800 ccagcagtgg agtttagtac ttaagagttt gtgcccttaa accagactcc ctggattaat    13860
gctgtgtacc cgtgggcaag gtgcctgaat tctctataca cctatttcct catctgtaaa   13920
atggcaataa tagtaatagt acctaatgtg tagggttgtt ataagcattg agtaagataa    13980
ataatataaa gcacttagaa cagtgcctgg aacataaaaa cacttaataa tagctcatag    14040
ctaacatttc ctatttacat ttcttctaga aatagccagt atttgttgag tgcctacatg    14100
ttagttcctt tactagttgc tttacatgta ttatcttata ttctgtttta aagtttcttc    14160
acagttacag attttcatga aattttactt ttaataaaag agaagtaaaa gtataaagta    14220 ttcacttta tgttcacagt cttttccttt aggctcatga tggagtatca gaggcatgag     14280
tgtgtttaac ctaagagcct taatggcttg aatcagaagc actttagtcc tgtatctgtt    14340
cagtgtcagc ctttcataca tcatttaaaa tcccatttga ctttaagtaa gtcacttaat    14400
ctctctacat gtcaatttct tcagctataa aatgatggta tttcaataaa taatacatt     14460 aattaaatga tattatactg actaattggg ctgttttaag gctcaataag aaaatttctg    14520
tgaaaggtct ctagaaaatg taggttccta tacaaataaa agataacatt gtgcttatag    14580
cttcggtgtt tatcatataa agctattctg agttatttga agagctcacc tactttttt    14640 tgttttagt ttgttaaatt gttttatagg caatgttttt aatctgtttt ctttaactta    14700
cagtgccatc agctcacact tgcaaacctg tggctgttcc gttgtagtag gtagcagtgc    14760
agagaaagta aataaggtag tttattttat aatctagcaa atgatttgac tctttaagac    14820
tgatgatata tcatggattg tcatttaaat ggtaggttgc aattaaaatg atctagtagt    14880
ataaggaggc aatgtaatct catcaaattg ctaagacacc ttgtggcaac agtgagtttg    14940
aaataaactg agtaagaatc atttatcagt ttattttgat agctcggaaa taccagtgtc    15000
agtagtgtat aaatggtttt gagaatatat taaaatcaga tatataaaaa aaattactct    15060
tctatttccc aatgttatct ttaacaaatc tgaagatagt catgtacttt tggtagtagt    15120
tccaaagaaa tgttatttgt ttattcatct tgatttcatt gtcttcgctt tccttctaaa    15180 tctgtcccttt ctagggagct attgggatta agtggtcatt gattattata ctttattcag   15240
taatgtttct gacccttttcc ttcagtgcta cttgagttaa ttaaggatta atgaacagtt    15300
acatttccaa gcattagcta ataaactaaa ggatttttgca cttttcttca ctgaccatta    15360
gttagaaaga gttcagagat aagtatgtgt atctttcaat ttcagcaaac ctaattttt     15420 aaaaaaagtt ttacatagga aatatgttgg aaatgatact ttacaaagat attcataatt    15480 ttttttttgta atcagctact ttgtatattt acatgagcct taatttatat ttctcatata    15540
accatttatg agagcttagt ataccgtgtt cattatattg catctacgaa ctagtgacct    15600
tattccttct gttacctcaa acaggtggct ttccatctgt gatctccaaa gccttaggtt    15660
gcacagagtg actgccgagc tgctttatga agggagaaag gctccatagt tggagtgttt    15720
tttttttttt ttttaaacat ttttcccatc ctccatcctc ttgagggaga atagcttacc    15780
ttttatcttg ttttaatttg agaaagaagt tgccaccact ctaggttgaa aaccactcct    15840
ttaacataat aactgtggat atggtttgaa tttcaagata gttacatgcc ttttatttt     15900 tcctaataga gctgtaggtc aaatattatt agaatcagat ttctaaatcc cacccaatga    15960
```

```
cctgcttatt ttaaatcaaa ttcaataatt aattctcttc tttttggagg atctggacat    16020
tctttgatat ttcttacaac gaatttcatg tgtagaccca ctaaacagaa gctataaaag    16080
ttgcatggtc aaataagtct gagaaagtct gcagatgata taattcacct gaagagtcac    16140
agtatgtagc caaatgttaa aggttttgag atgccataca gtaaatttac caagcatttt    16200
ctaaatttat ttgaccacag aatccctatt ttaagcaaca actgttacat cccatggatt    16260
ccaggtgact aaagaatact tatttcttag gatatgtttt attgataata acaattaaaa    16320
tttcagatat ctttcataag caaatcagtg gtcttttttac ttcatgtttt aatgctaaaa   16380 tatttttcttt tatagatagt cagaacatta tgccttttttc tgactccagc agagagaaaa  16440
tgctccaggt tatgtgaagc agaatcatca tttaaatatg agtcagggct ctttgtacaa    16500
ggcctgctaa aggtatagtt tctagttatc acaagtgaaa ccacttttct aaaatcattt    16560
ttgagactct ttatagacaa atcttaaata ttagcattta atgtatctca tattgacatg    16620
cccagagact gacttccttt acacagttct gcacatagac tatatgtctt atggatttat    16680
agttagtatc atcagtgaaa caccatagaa taccctttgt gttccaggtg ggtccctgtt    16740
cctacatgtc tagcctcagg acttttttttt ttttaacaca tgcttaaatc aggttgcaca   16800
tcaaaaataa gatcatttct ttttaactaa atagatttga attttattga aaaaaatttt    16860
taaacatctt taagaagctt ataggattta agcaattcct atgtatgtgt actaaaatat    16920
atatatttct atatataata tatattagaa aaaaattgta ttttctttt atttgagtct     16980 actgtcaagg agcaaaacag agaaatgtaa attagcaatt atttataata cttaaaggga    17040
agaaagttgt tcaccttgtt gaatctatta ttgttatttc aattatagtc ccaagacgtg    17100
aagaaatagc tttcctaatg gttatgtgat tgtctcatag tgactacttt cttgaggatg    17160
tagccacggc aaaatgaaat aaaaaaattt aaaaattgtt gcaaatacaa gttatattag    17220
gcttttgtgc atttttcaata atgtgctgct atgaactcag aatgatagta tttaaatata   17280
gaaactagtt aaaggaaacg tagtttctat ttgagttata catatctgta aattagaact    17340
tctcctgtta aaggcataat aaagtgctta atacttttgt ttcctcagca ccctctcatt    17400
taattatata attttagttc tgaaagggac ctataccaga tgcctagagg aaatttcaaa    17460
actatgatct aatgaaaaaa tatttaatag ttctccatgc aaatacaaat catatagttt    17520
tccagaaaat acctttgaca ttatacaaag atgattatca cagcattata atagtaaaaa   17580
aatggaaata gcctctttct tctgttctgt tcatagcaca gtgcctcata cgcagtaggt    17640
tattattaca tggtaactgg ctaccccaac tgattaggaa agaagtaaat ttgttttata    17700
aaaatacata ctcattgagg tgcatagaat aattaagaaa ttaaaagaca cttgtaattt    17760
tgaatccagt gaatacccac tgttaatatt tggtatatct cttttctagtc tttttttccc   17820 ttttgcatgt attttctttta agactcccac ccccactgga tcatctctgc atgttctaat   17880 ctgcttttttt cacagcagat tctaagcctc tttgaatatc aacacaaact tcaacaactt   17940
catctataga tgccaaataa taaattcatt tttatttact taaccacttc ctttggatgc    18000
ttaggtcatt ctgatgtttt gctattgaaa ccaatgctat actgaacact tctgtcacta    18060
aaactttgca cacactcatg aatagcttct taggataaat ttttagagat ggatttgcta    18120
aatcagagac catttttttaa aattaaaaaa caattattca tatcgtttgg catgtaagac   18180
agtaaatttt cctttttattt tgacaggatt caactggaag ctttgtgctg cctttccggc   18240
aagtcatgta tgctccatat cccaccacac acatagatgt ggatgtcaat actgtgaagc    18300
```

```
agatgccacc ctgtcatgaa catatttata atcagcgtag atacatgaga tccgagctga   18360
cagccttctg gagagccact tcagaagaag acatggctca ggatacgatc atctacactg   18420
acgaaagctt tactcctgat ttgtacgtaa tgctctgcct gctggtactg tagtcaagca   18480
atatgaaatt gtgtctttta cgaataaaaa caaaacagaa gttgcattta aaagaaaga    18540 aatattacca gcagaattat gcttgaagaa acatttaatc aagcattttt ttcttaaatg   18600
ttcttctttt tccatacaat tgtgtttacc ctaaaatagg taagattaac ccttaaagta   18660
aatatttaac tatttgttta ataaatatat attgagctcc taggcactgt tctaggtacc   18720
gggcttaata gtggccaacc agacagcccc agccccagcc cctacattgt gtatagtcta   18780
ttatgtaaca gttattgaat ggacttatta acaaaaccaa agaagtaatt ctaagtcttt   18840
tttttcttga catatgaata taaaatacag caaaactgtt aaaatatatt aatggaacat   18900 tttttttactt tgcattttat attgttattc acttcttatt ttttttttaaa aaaaaaagcc   18960 tgaacagtaa attcaaaagg aaaagtaatg ataattaatt gttgagcatg gacccaactt   19020
gaaaaaaaaa atgatgatga taaatctata atcctaaaac cctaagtaaa cacttaaaag   19080
atgttctgaa atcaggaaaa gaattatagt atactttgt gtttctcttt tatcagttga    19140
aaaaaggcac agtagctcat gcctgtaaga acagagcttt gggagtgcaa ggcaggcgga   19200
tcacttgagg ccaggagttc cagaccagcc tgggcaacat agtgaaaccc catctctaca   19260
aaaaataaaa aagaattatt ggaatgtgtt tctgtgtgcc tgtaatccta gctattccga   19320
aagctgaggc aggaggatct tttgagccca ggagtttgag gttacaggga gttatgatgt   19380
gccagtgtac tccagcctgg ggaacaccga gactctgtct tatttaaaaa aaaaaaaaaa   19440
aaaatgcttg caataatgcc tggcacatag aaggtaacag taagtgttaa ctgtaataac   19500
ccaggtctaa gtgtgtaagg caatagaaaa attggggcaa ataagcctga cctatgtatc   19560
tacagaatca gtttgagctt aggtaacaga cctgtggagc accagtaatt acacagtaag   19620
tgttaaccaa aagcatagaa taggaatatc ttgttcaagg acccccagc cttatacatc     19680 tcaaggtgca gaaagatgac ttaatatagg acccattttt tcctagttct ccagagtttt   19740
tattggttct tgagaaagta gtaggggaat gttttagaaa atgaattggt ccaactgaaa   19800
ttacatgtca gtaagttttt atatattggt aaattttagt agacatgtag aagttttcta   19860
attaatctgt gccttgaaac atttctttt tccctaaagt gcttagtatt ttttccgttt      19920
tttgattggt tacttgggag cttttttgag gaaatttagt gaactgcaga atgggtttgc   19980
aaccatttgg tattttgtt ttgtttttta gaggatgtat gtgtattta acatttctta       20040 atcattttta gccagctatg tttgtttgc tgatttgaca aactacagtt agacagctat     20100
tctcattttg ctgatcatga caaaataata tcctgaattt ttaaattttg catccagctc   20160 taaatttct aaacataaaa ttgtccaaaa aatagtattt tcagccacta gattgtgtgt    20220
taagtctatt gtcacagagt cattttactt ttaagtatat gttttacat gttaattatg     20280 tttgttattt ttaattttaa cttttaaaa taattccagt cactgccaat acatgaaaaa     20340
ttggtcactg gaattttttt tttgactttt attttaggtt catgtgtaca tgtgcaggtg   20400
tgttatacag gtaaattgcg tgtcatgagg gtttggtgta caggtgattt cattacccag   20460
gtaataagca tagtacccaa taggtagttt tttgatcctc acccttctcc caccctcaag   20520
taggccctgg tgttgctgtt tccttctttg tgtccatgta tactcagtgt ttagctccca   20580
cttagaagtg agaacatgcg gtagttggtt ttctgttcct ggattagttc acttaggata   20640
atgacctcta gctccatctg gttttttatgg ctgcatagta ttccatggtg tatatgtatc   20700
```

```
acatttctt tatccagtct accattgata ggcatttagg ttgattccct gtctttgtta    20760
tcatgaatag tgctgtgatg aacatacaca tgcatgtgtc tttatggtag aaaaatttgt    20820
attcctttag gtacatatag aataatgggg ttgctagggt gaatggtagt tctattttca    20880
gttatttgag aaatcttcaa actgcttttc ataatagcta aactaattta cagtcccgcc    20940
agcagtgtat aagtgttccc ttttctccac aaccttgcca acatctgtga tttttgact    21000
ttttaataat agccattcct agagaattga tttgcaattc tctattagtg atattaagca    21060
tttttcata tgcttttag ctgtctgtat atattcttct gaaaaatttt catgtccttt    21120
gcccagtttg tagtggggtg ggttgttttt tgcttgttaa ttagttttaa gttccttcca    21180
gattctgcat atcctttgt tggatacatg gtttgcagat attttctcc cattgtgtag    21240
gttgtctttt actctgttga tagtttcttt tgccatgcag gagctcgtta ggtcccattt    21300
gtgtttgttt ttgttgcagt tgcttttggc gtcttcatca taaaatctgt gccagggcct    21360
atgtccagaa tggtatttcc taggttgtct tccagggttt ttacaatttt agattttacg    21420
tttatgtctt taatccatct tgagttgatt tttgtatatg gcacaaggaa ggggtccagt    21480
ttcactccaa ttcctatggc tagcaattat cccagcacca tttattgaat acggagtcct    21540
ttccccattg cttgttttt gtcaacttg ttgaagatca gatggttgta agtgtgtggc    21600
tttatttctt ggctctctat tctccattgg tctatgtgtc tgtttttata acagtaccct    21660
gctgttcagg ttcctatagc cttttagtat aaaatcggct aatgtgatgc ctccagcttt    21720
gttcttttg cttaggattg ctttggctat ttgggctcct ttttgggtcc atattaattt    21780
taaaacagtt ttttctggtt ttgtgaagga tatcattggt agtttatagg aatagcattg    21840
aatctgtaga ttgctttggg cagtatggcc atttttaacaa tattaattct tcctatctat    21900
gaatatggaa tgttttttcca tgtgtttgtg tcatctcttt atacctgatg tataaagaaa    21960
agctggtatt attcctactc aatctgttcc aaaaaattga ggaggaggaa ctcttcccta    22020
atgaggccag catcattctg ataccaaaac ctggcagaga cacaacagaa aaaagaaaac    22080
ttcaggccaa tatccttgat gaatatagat gcaaaaatcc tcaacaaaat actagcaaac    22140
caaatccagc agcacatcaa aaagctgatc tactttgatc aagtaggctt tatccctggg    22200
atgcaaggtt ggttcaacat acacaaatca ataagtgtga ttcatcacat aaacagagct    22260
aaaaacaaaa accacaagat tatctcaata ggtagagaaa aggttgtcaa taaaatttaa    22320
catcctccat gttaaaaacc ttcagtaggt caggtgtagt gactcacacc tgtaatccca    22380
gcactttggg aggccaaggc gggcatatct cttaagccca ggagttcaag acgagcctag    22440
gcagcatggt gaaacccat ctctacaaaa aaaaaaaaa aaaaaatta gcttggtatg    22500
gtgacatgca cctatagtcc cagctattca ggaggttgag gtgggaggat tgtttgagcc    22560
cgggaggcag aggttggcag cgagctgaga tcatgccacc gcactccagc ctgggcaacg    22620
gagtgagacc ctgtctcaaa aagaaaaat cacaaacaat cctaaacaaa ctaggcattg    22680
aaggaacatg cctcaaaaaa ataagaacca tctatgacag acccatagcc aatatcttac    22740
caaatgggca aaagctggaa gtattctcct tgagaaccgt aacaagacaa ggatgtccac    22800
tctcaccact ccttttcagc atagttctgg aagtcctagc cagagcaatc aggaaagaga    22860
aagaaagaaa gacattcaga taggaagaga agaagtcaaa ctatttctgt ttgcaggcag    22920
tataattctg tacctagaaa atctcatagt ctctgcccag aaactcctaa atctgttaaa    22980
aatttcagca aagttttggc attctctata ctccaacacc ttccaaagtg agagcaaaat    23040
```

```
caagaacaca gtcccattca caatagccgc aaaacgaata aaatacctag gaatccagct   23100
aaccagggag gtgaaagatc tctatgagaa ttacaaaaca ctgctgaaag aaatcagaga   23160
tgacacaaac aaatggaaat gttcttttttt aacaccttgc tttatctaat tcacttatga   23220
tgaagatact cattcagtgg aacaggtata ataagtccac tcgattaaat ataagcctta   23280
ttctctttcc agagcccaag aagggcact atcagtgccc agtcaataat gacgaaatgc    23340
taatattttt cccctttacg gtttctttct tctgtagtgt ggtacactcg tttcttaaga   23400
taaggaaact tgaactacct tcctgtttgc ttctacacat acccattctc ttttttttgcc  23460 actctggtca ggtataggat gatccctacc actttcagtt aaaaactcct cctcttacta   23520
aatgttctct taccctctgg cctgagtaga acctagggaa aatggaagag aaaaagatga   23580
aagggaggtg gggcctggga agggaataag tagtcctgtt tgtttgtgtg tttgctttag   23640
cacctgctat atcctaggtg ctgtgttagg cacacattat tttaagtggc cattatatta   23700
ctactactca ctctggtcgt tgccaaggta ggtagtactt tcttggatag ttggttcatg   23760
ttacttacag atggtgggct tgttgaggca aacccagtgg ataatcatcg gagtgtgttc   23820
tctaatctca ctcaaatttt tcttcacatt ttttggtttg ttttggtttt tgatggtagt   23880
ggcttatttt tgttgctggt ttgttttttg ttttttttg agatggcaag aattggtagt    23940
tttatttatt aattgcctaa gggtctctac tttttttaaa agatgagagt agtaaaatag   24000
attgatagat acatacatac ccttactggg gactgcttat attctttaga gaaaaaatta   24060
catattagcc tgacaaacac cagtaaaatg taaatatatc cttgagtaaa taatgaatg    24120 tatattttgt gtctccaaat atatatatct atattcttac aaatgtgttt atatgtaata   24180
tcaatttata agaacttaaa atgttggctc aagtgaggga ttgtggaagg tagcattata   24240
tggccatttc aacatttgaa ctttttttctt ttcttcattt tcttcttttc ttcaggaata   24300
tttttcaaga tgtcttacac agagacactc tagtgaaagc cttcctggat caggtaaatg   24360
ttgaacttga gattgtcaga gtgaatgata tgacatgttt tcttttttaa tatatcctac   24420
aatgcctgtt ctatatattt atattcccct ggatcatgcc ccagagttct gctcagcaat   24480
tgcagttaag ttagttacac tacagttctc agaagagtct gtgagggcat gtcaagtgca   24540
tcattacatt ggttgcctct tgtcctagat ttatgcttcg ggaattcaga cctttgttta   24600
caatataata aatattattg ctatcttttta aagatataat aataagatat aaagttgacc   24660
acaactactg ttttttgaaa catagaattc ctggtttaca tgtatcaaag tgaaatctga   24720
cttagctttt acagatataa tatatacata tatatatcct gcaatgcttg tactatatat   24780
gtagtacaag tatatatata tgtttgtgtg tgtatatata tatagtacga gcatatatac   24840
atattaccag cattgtagga tatatatatg tttatatatt aaaaaaagt tataaactta    24900 aaaccctatt atgttatgta gagtatatgt tatatatgat atgtaaaata tataacatat   24960
actctatgat agagtgtaat atatttttta tatatatttt aacatttata aaatgataga   25020
attaagaatt gagtcctaat ctgttttatt aggtgctttt tgtagtgtct ggtctttcta   25080
aagtgtctaa atgattttc cttttgactt attaatgggg aagagcctgt atattaacaa    25140
ttaagagtgc agcattccat acgtcaaaca acaaacattt taattcaagc attacctat    25200 aacaagtaag tttttttttt tttttgaga aagggaggtt gtttatttgc ctgaaatgac    25260
tcaaaaatat ttttgaaaca tagtgtactt attttaaataa catctttatt gtttcattct  25320
tttaaaaaat atctacttaa ttacacagtt gaaggaaatc gtagattata tggaacttat   25380
ttcttaatat attacagttt gttataataa cattctgggg atcaggccag gaaactgtgt   25440
```

```
catagataaa gctttgaaat aatgagatcc ttatgtttac tagaaatttt ggattgagat   25500
ctatgaggtc tgtgacatat tgcgaagttc aaggaaaatt cgtaggcctg gaatttcatg   25560
cttctcaagc tgacataaaa tccctcccac tctccacctc atcatatgca cacattctac   25620
tcctacccac ccactccacc ccctgcaaaa gtacaggtat atgaatgtct caaaaccata   25680
ggctcatctt ctaggagctt caatgttatt tgaagatttg ggcagaaaaa attaagtaat   25740
acgaaataac ttatgtatga gttttaaaag tgaagtaaac atggatgtat tctgaagtag   25800
aatgcaaaat ttgaatgcat ttttaaagat aaattagaaa acttctaaaa actgtcagat   25860
tgtctgggcc tggtggctta tgcctgtaat cccagcactt tgggagtccg aggtgggtgg   25920
atcacaaggt caggagatcg agaccatcct gccaacatgg tgaaaccccg tctctactaa   25980
gtatacaaaa attagctggg cgtggcagcg tgtgcctgta atcccagcta cctgggaggc   26040
tgaggcagga gaatcgcttg aacccaggag gtgtaggttg cagtgagtca gatcgcgcc   26100 actgcacttt agcctggtga cagagctaga ctccgtctca aaaaaaaaaa aaaatatcag   26160
attgttccta cacctagtgc ttctatacca cactcctgtt aggggcatc agtggaaatg   26220 gttaaggaga tgtttagtgt gtattgtctg ccaagcactg tcaacactgt catagaaact   26280
tctgtacgag tagaatgtga gcaaattatg tgttgaaatg gttcctctcc ctgcaggtct   26340
ttcagctgaa acctggctta tctctcagaa gtactttcct tgcacagttt ctacttgtcc   26400
ttcacagaaa agccttgaca ctaataaaat atatagaaga cgatacgtga gtaaaactcc   26460 tacacgaag aaaaaccttt gtacattgtt tttttgtttt gtttccttg tacatttct   26520 atatcataat ttttgcgctt cttttttttt tttttttttt tttttttcca ttattttag   26580 gcagaaggga aaaagccct ttaaatctct tcggaacctg aagatagacc ttgatttaac   26640
agcagagggc gatcttaaca taataatggc tctggctgag aaaattaaac caggcctaca   26700
ctcttttatc tttggaagac ctttctacac tagtgtgcaa gaacgagatg ttctaatgac   26760
tttttaaatg tgtaacttaa taagcctatt ccatcacaat catgatcgct ggtaaagtag   26820
ctcagtggtg tggggaaacg ttcccctgga tcatactcca gaattctgct ctcagcaatt   26880
gcagttaagt aagttacact acagttctca caagagcctg tgaggggatg tcaggtgcat   26940
cattacattg ggtgtctctt ttcctagatt tatgcttttg ggatacagac ctatgtttac   27000
aatataataa atattattgc tatcttttaa agatataata ataggatgta aacttgacca   27060
caactactgt tttttgaaa tacatgattc atggtttaca tgtgtcaagg tgaaatctga   27120 gttggcttt acagatagtt gactttctat cttttggcat tctttggtgt gtagaattac   27180
tgtaatactt ctgcaatcaa ctgaaaacta gagcctttaa atgatttcaa ttccacagaa   27240
agaaagtgag cttgaacata ggatgagctt tagaaagaaa attgatcaag cagatgttta   27300
attggaattg attattagat cctactttgt ggatttagtc cctgggattc agtctgtaga   27360
aatgtctaat agttctctat agtccttgtt cctggtgaac cacagttagg gtgttttgtt   27420
tattttattg ttcttgctat tgttgatatt ctatgtagtt gagctctgta aaggaaatt   27480 gtatttatg ttttagtaat tgttgccaac ttttaaatt aatttcatt atttttgagc   27540 caaattgaaa tgtgcacctc ctgtgccttt tttctcctta gaaatctaa ttacttggaa   27600 caagttcaga tttcactggt cagtcatttt catcttgttt tcttcttgct aagtcttacc   27660
atgtacctgc tttggcaatc attgcaactc tgagattata aaatgcctta gagaatatac   27720
taactaataa gatctttttt tcagaaacag aaaatagttc cttgagtact tccttcttgc   27780
```

```
atttctgcct atgttttcga agttgttgct gtttgcctgc aataggctat aaggaatagc    27840
aggagaaatt ttactgaagt gctgttttcc taggtgctac tttggcagag ctaagttatc    27900
ttttgttttc ttaatgcgtt tggaccattt tgctggctat aaaataactg attaatataa    27960
ttctaacaca atgttgacat tgtagttaca caaacacaaa taaatatttt atttaaaatt    28020
ctggaagtaa tataaaaggg aaaatatatt tataagaaag ggataaaggt aatagagccc    28080
ttctgccccc cacccaccaa atttacacaa caaaatgaca tgttcgaatg tgaaaggtca    28140
taatagcttt cccatcatga atcagaaaga tgtggacagc ttgatgtttt agacaaccac    28200
tgaactagat gactgttgta ctgtagctca gtcatttaaa aaatatataa atactacctt    28260
gtagtgtccc atactgtgtt ttttacatgg tagattctta tttaagtgct aactggttat    28320
tttctttggc tggtttattg tactgttata cagaatgtaa gttgtacagt gaaataagtt    28380
attaaagcat gtgtaaacat tgttatatat cttttctcct aaatggagaa ttttgaataa    28440
aatatatttg aaattttgcc tctttcagtt gttcattcag aaaaaaatac tatgatattt    28500
gaagactgat cagcttctgt tcagctgaca gtcatgctgg atctaaactt tttttaaaat    28560
taattttgtc ttttcaaaga aaaaatattt aaagaagctt tataatataa tcttatgtta    28620
aaaaaacttt ctgcttaact ctctggattt cattttgatt tttcaaatta tatattaata    28680
tttcaaatgt aaaatactat ttagataaat tgttttttaaa cattcttatt attataaat    28740
taatataacc taaactgaag ttattcatcc caggtatcta atacatgtat ccaaagtaaa    28800
aatccaagga atctgaacac tttcatctgc aaagctagga ataggtttga cattttcact    28860
ccaagaaaaa gttttttttt gaaaatagaa tagttgggat gagaggtttc tttaaaagaa    28920
gactaactga tcacattact atgattctca agaagaaac caaaacttca tataatacta    28980
taaagtaaat ataaaatagt tccttctata gtatatttct ataatgctac agtttaaaca    29040
gatcactctt atataatact attttgattt tgatgtagaa ttgcacaaat tgatatttct    29100
cctatgatct gcagggtata gcttaaagta acaaaaacag tcaaccacct ccatttaaca    29160
cacagtaaca ctatgggact agttttatta cttccatttt acaaatgagg aaactaaagc    29220
ttaaagatgt gtaatacacc gcccaaggtc acacagctgg taaaggtgga tttcatccca    29280
gacagttaca gtcattgcca tgggcacagc tcctaactta gtaactccat gtaactggta    29340
ctcagtgtag ctgaattgaa aggagagtaa ggaagcaggt tttacaggtc tacttgcact    29400
attcagagcc cgagtgtgaa tccctgctgt gctgcttgga gaagttactt aacctatgca    29460
aggttcattt tgtaaatatt ggaaatggag tgataatacg tacttcacca gaggatttaa    29520
tgagaccta tacgatcctt agttcagtac ctgactagtg cttcataaat gcttttcat     29580
ccaatctgac aatctccagc ttgtaattgg ggcatttaga acatttaata tgattattgg    29640
catggtaggt taaagctgtc atcttgctgt tttctatttg ttcttttgt tttctcctta    29700
cttttggatt ttttattct actatgtctt ttctattgtc ttattaacta tactctttga    29760
tttatttag tggttgtttt agggttatac ctctttctaa tttaccagtt tataaccagt    29820
ttatatacta cttgacatat agcttaagaa acttactgtt gttgtctttt tgctgttatg    29880
gtcttaacgt ttttatttct acaaacatta taaactccac actttattgt tttttaattt    29940
tacttataca gtcaattatc ttttaaagat atttaaatat aaacattcaa aacaccccaa    30000
t                                                                   30001

<210> SEQ ID NO 3
<211> LENGTH: 1031
```

```
<212> TYPE: DNA
<213> ORGANISM: homo sapiens

<400> SEQUENCE: 3
attcccggga tacgtaacct acggtgtccc gctaggaaag agaggtgcgt caaacagcga     60
caagttccgc ccacgtaaaa gatgacgctt ggtgtgtcag ccgtccctgc tgcccggttg    120
cttctctttt gggggcgggg tctagcaaga gcaggtgtgg gtttaggaga tatctccgga    180
gcatttggat aatgtgacag ttggaatgca gtgatgtcga ctctttgccc accgccatct    240
ccagctgttg ccaagacaga gattgcttta agtggcaaat cacctttatt agcagctact    300
tttgcttact gggacaatat tcttggtcct agagtaaggc acatttgggc tccaaagaca    360
gaacaggtac ttctcagtga tggagaaata acttttcttg ccaaccacac tctaaatgga    420
gaaatccttc gaaatgcaga gagtggtgct atagatgtaa agttttttgt cttgtctgaa    480
aagggagtga ttattgtttc attaatcttt gatggaaact ggaatgggga tcgcagcaca    540
tatggactat caattatact tccacagaca gaacttagtt tctacctccc acttcataga    600
gtgtgtgttg atagattaac acatataatc cggaaggaa gaatatggat gcataaggaa     660
agacaagaaa aatgtccaga agattatctt agaaggcaca gagagaatgg aagatcaggg    720
tcagagtatt attccaatgc ttactggaga agtgattcct gtaatggaaa ctgctttcct    780
ctatgaaatt cccccgggtt cctggaggaa atagatatag gctgatacag ttacccaatg    840
atggatgaat attgggggac cgcctggtca ttgaaaggct ttcttttctc caggaaagaa    900 attttttttcc ttttccataa aaagcttggg aatggaagac aacaattccc attcttttt     960 tgcgttccac ccctatgtga caacagaaat ttttggggaa caacaacga aaaattttta    1020 tcccgcgcgc a                                                        1031

<210> SEQ ID NO 4
<211> LENGTH: 3244
<212> TYPE: DNA
<213> ORGANISM: homo sapiens

<400> SEQUENCE: 4
gggcggggct gcggttgcgg tgcctgcgcc cgcggcggcg gaggcgcagg cggtggcgag     60
tggatatctc cggagcattt ggataatgtg acagttggaa tgcagtgatg tcgactcttt    120
gcccaccgcc atctccagct gttgccaaga cagagattgc tttaagtggc aaatcacctt    180
tattagcagc tacttttgct tactgggaca atattcttgg tcctagagta aggcacattt    240
gggctccaaa gacagaacag gtacttctca gtgatggaga ataacttttt cttgccaacc    300
acactctaaa tggagaaatc cttcgaaatg cagagagtgg tgctatagat gtaaagtttt    360
ttgtcttgtc tgaaaaggga gtgattattg tttcattaat ctttgatgga aactggaatg    420
gggatcgcag cacatatgga ctatcaatta cttccacaga cagaacttag tttctacc     480 tcccacttca tagagtgtgt gttgatagat taacacatat aatccggaaa ggaagaatat    540
ggatgcataa ggaaagacaa gaaaatgtcc agaagattat cttagaaggc acagagagaa    600
tggaagatca gggtcagagt attattccaa tgcttactgg agaagtgatt cctgtaatgg    660
aactgctttc atctatgaaa tcacacagtg ttcctgaaga aatagatata gctgatacag    720
tactcaatga tgatgatatt ggtgacagct gtcatgaagg cttttcttctc aatgccatca    780 gctcacactt gcaaacctgt ggctgttccg ttgtagtagg tagcagtgca gagaaagtaa    840
ataagatagt cagaacatta tgcctttttc tgactccagc agagagaaaa tgctccaggt    900
```

```
tatgtgaagc agaatcatca tttaaatatg agtcagggct ctttgtacaa ggcctgctaa    960
aggattcaac tggaagcttt gtgctgcctt tccggcaagt catgtatgct ccatatccca   1020
ccacacacat agatgtggat gtcaatactg tgaagcagat gccaccctgt catgaacata   1080
tttataatca gcgtagatac atgagatccg agctgacagc cttctggaga gccacttcag   1140
aagaagacat ggctcaggat acgatcatct acactgacga aagctttact cctgatttga   1200
atattttca agatgtctta cacagagaca ctctagtgaa agccttcctg gatcaggtct    1260
ttcagctgaa acctggctta tctctcagaa gtactttcct tgcacagttt ctacttgtcc   1320
ttcacagaaa agccttgaca ctaataaaat atatagaaga cgatacgcag aagggaaaaa   1380
agccctttaa atctcttcgg aacctgaaga tagaccttga tttaacagca gagggcgatc   1440
ttaacataat aatggctctg gctgagaaaa ttaaaccagg cctacactct tttatctttg   1500
gaagaccttt ctacactagt gtgcaagaac gagatgttct aatgactttt taaatgtgta   1560
acttaataag cctattccat cacaatcatg atcgctggta aagtagctca gtggtgtggg   1620
gaaacgttcc cctggatcat actccagaat tctgctctca gcaattgcag ttaagtaagt   1680
tacactacag ttctcacaag agcctgtgag gggatgtcag gtgcatcatt acattgggtg   1740
tctcttttcc tagattatg cttttgggat acagacctat gttacaata taataaatat     1800
tattgctatc ttttaaagat ataataatag gatgtaaact tgaccacaac tactgttttt   1860
ttgaaataca tgattcatgg tttacatgtg tcaaggtgaa atctgagttg gcttttacag   1920
atagttgact ttctatcttt tggcattctt tggtgtgtag aattactgta atacttctgc   1980
aatcaactga aaactagagc ctttaaatga tttcaattcc acagaaagaa agtgagcttg   2040
aacataggat gagctttaga aagaaaattg atcaagcaga tgtttaattg gaattgatta   2100
ttagatccta ctttgtggat ttagtccctg ggattcagtc tgtagaaatg tctaatagtt   2160
ctctatagtc cttgttcctg gtgaaccaca gttagggtgt tttgtttatt ttattgttct   2220
tgctattgtt gatattctat gtagttgagc tctgtaaaag gaaattgtat tttatgttt    2280
agtaattgtt gccaactttt taaattaatt ttcattattt ttgagccaaa ttgaaatgtg   2340
cacctcctgt gccttttttc tccttagaaa atctaattac ttggaacaag ttcagatttc   2400
actggtcagt cattttcatc ttgttttctt cttgctaagt cttaccatgt acctgctttg   2460
gcaatcattg caactctgag attataaaat gccttagaga atatactaac taataagatc   2520
ttttttcag aaacagaaaa tagttccttg agtacttcct tcttgcattt ctgcctatgt    2580
ttttgaagtt gttgctgttt gcctgcaata ggctataagg aatagcagga gaaattttac   2640
tgaagtgctg ttttcctagg tgctactttg gcagagctaa gttatctttt gttttcttaa   2700
tgcgtttgga ccatttgct ggctataaaa taactgatta atataattct aacacaatgt    2760
tgacattgta gttacacaaa cacaaataaa tattttattt aaaattctgg aagtaatata   2820
aaagggaaaa tatatttata agaaagggat aaagtaata gagcccttct gcccccacc     2880
caccaaattt acacaacaaa atgacatgtt cgaatgtgaa aggtcataat agctttccca   2940
tcatgaatca gaaagatgtg gacagcttga tgttttagac aaccactgaa ctagatgact   3000
gttgtactgt agctcagtca tttaaaaaat atataaatac taccttgtag tgtcccatac   3060
tgtgtttttt acatggtaga ttcttattta agtgctaact ggttattttc tttggctggt   3120
ttattgtact gttatacaga atgtaagttg tacagtgaaa taagttatta aagcatgtgt   3180
aaacattgtt atatatcttt tctcctaaat ggagaatttt gaataaaata tatttgaaat   3240
tttg                                                                3244
```

<210> SEQ ID NO 5
<211> LENGTH: 761
<212> TYPE: DNA
<213> ORGANISM: homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5

```
cacgaggctt tgatatttct tacaacgaat tcatgtgta gacccactaa acagaagcta      60
taaaagttgc atggtcaaat aagtctgaga aagtctgcag atgatataat tcacctgaag    120
agtcacagta tgtagccaaa tgttaaaggt tttgagatgc catacagtaa atttaccaag    180
cattttctaa atttatttga ccacagaatc cctattttaa gcaacaactg ttacatccca    240
tggattccag gtgactaaag aatacttatt tcttaggata tgttttattg ataataacaa    300
ttaaaatttc agatatcttt cataagcaaa tcagtggtct ttttacttca tgtttttaatg   360
ctaaaatatt ttcttttata gatagtcaga acattatgcc ttttctgac tccagcagag    420
agaaaatgct ccaggttatg tgaagcagaa tcatcattta aatatgagtc agggctcttt    480
gtacaaggcc tgctaaagga ttcaactgga agctttgtgc tgccttttccg gcaagtcatg   540
tatgctccat atcccaccac acacatagat gtggatgtca atactgtgaa gcagatgcca    600
ccctgtcatg aacatattta taatcagcgt agatacatga gatccgagct gacagccttc    660
tggagagcca cttcagaaga agacatggct cangatacga tcatctacac tgacgaaagc    720
tntactcctg atttgaatat ttttcaagat gtcttacaca g                        761
```

<210> SEQ ID NO 6
<211> LENGTH: 1901
<212> TYPE: DNA
<213> ORGANISM: homo sapiens

<400> SEQUENCE: 6

```
acgtaaccta cggtgtcccg ctaggaaaga gaggtgcgtc aaacagcgac aagttccgcc     60
cacgtaaaag atgacgcttg atatctccgg agcatttgga taatgtgaca gttggaatgc    120
agtgatgtcg actctttgcc caccgccatc tccagctgtt gccaagacag agattgcttt    180
aagtggcaaa tcacctttat tagcagctac ttttgcttac tgggacaata ttcttggtcc    240
tagagtaagg cacatttggg ctccaaagac agaacaggta cttctcagtg atggagaaat    300
aactttctct gccaaccaca ctctaaatgg agaaatcctt cgaaatgcag agagtggtgc    360
tatagatgta aagtttttg tcttgtctga aaagggagtg attattgttt cattaatctt    420
tgatggaaac tggaatgggg atcgcagcac atatggacta tcaattatac ttccacagac    480
agaacttagt ttctacctcc cacttcatag agtgtgtgtt gatagattaa cacatataat    540
ccggaaagga agaatatgga tgcataagga aagacaagaa aatgtccaga agattatctt    600
agaaggcaca gagagaatgg aagatcaggg tcagagtatt attccaatgc ttactggaga    660
agtgattcct gtaatggaac tgctttcatc tatgaaatca cacagtgttc ctgaagaaat    720
agatatagct gatacagtac tcaatgatga tgatattggt gacagctgtc atgaaggctt    780
tcttctcaag taagaatttt tcttttcata aaagctggat gaagcagata ccatcttatg    840
```

```
ctcacctatg acaagatttg gaagaaagaa aataacagac tgtctactta gattgttcta    900
gggacattac gtatttgaac tgttgcttaa atttgtgtta ttttttcactc attatatttc   960
tatatatatt tggtgttatt ccatttgcta tttaaagaaa ccgagtttcc atcccagaca   1020
agaaatcatg gccccttgct tgattctggt ttcttgtttt acttctcatt aaagctaaca   1080
gaatcctttc atattaagtt gtactgtaga tgaacttaag ttatttaggc gtagaacaaa   1140
attattcata tttatactga tcttttttcca tccagcagtg gagtttagta cttaagagtt   1200
tgtgcccctta aaccagactc cctggattaa tgctgtgtac ccgtgggcaa ggtgcctgaa   1260
ttctctatac acctattccc tcatctgtaa aatggcaata atagtaatag tacctaatgt   1320
gtagggttgt tataagcatt gagtaagata aataatataa agcacttaga acagtgcctg   1380
gaacataaaa acacttaata atagctcata gctaacattt cctatttaca tttcttctag   1440
aaatagccag tatttgttga gtgcctacat gttagttcct ttactagttg ctttacatgt   1500
attatcttat attctgtttt aaagtttctt cacagttaca gatttttcatg aaatttttact  1560
tttaataaaa gagaagtaaa agtataaagt attcactttt atgttcacag tcttttcctt   1620
taggctcatg atggagtatc agaggcatga gtgtgtttaa cctaagagcc ttaatggctt   1680
gaatcagaag cactttagtc ctgtatctgt tcagtgtcag cctttcatac atcattttaa   1740
atcccatttg actttaagta agtcacttaa tctctctaca tgtcaatttc ttcagctata   1800
aaatgatggt atttcaataa ataaatacat taattaaatg atattatact gactaattgg   1860
gctgttttaa ggcaaaaaaa aaaaaaaaa aaaaaaaaa a                          1901
```

<210> SEQ ID NO 7
<211> LENGTH: 562
<212> TYPE: DNA
<213> ORGANISM: homo sapiens
<220> FEATURE:
<221> NAME/KEY: misc_feature
<222> LOCATION: (166)..(166)
<223> OTHER INFORMATION: n is a, c, g, or t

<400> SEQUENCE: 7

```
agacgtaacc tacggtgtcc cgctaggaaa gagagatatc tccggagcat ttggataatg     60
tgacagttgg aatgcagtga tgtcgactct ttgcccaccg ccatctccag ctgttgccaa    120
gacagagatt gctttaagtg gcaaatcacc tttattagca gctacntttt gcttactggg    180
acaatattct tggtcctaga gtaaggcaca tttgggctcc aaagacagaa caggtacttc    240
tcagtgatgg agaaataact tttcttgcca accacactct aaatggagaa tccttcgaa    300
atgcagagag tggtgctata gatgtaaagt ttttgtctt gtctgaaaag ggagtgatta    360
ttgtttcatt aatctttgat ggaaactgga atggggatcg cagcacatat ggactatcaa    420
ttatacttcc acagacagaa cttagtttct acctcccact tcatagagtg tgtgttgata    480
gattaacaca tataatccgg aaaggaagaa tatggatgca taaggaagaa caagaaaatg    540
tccagaagat tatcttagaa gg                                             562
```

<210> SEQ ID NO 8
<211> LENGTH: 798
<212> TYPE: DNA
<213> ORGANISM: homo sapiens

<400> SEQUENCE: 8

```
gggctctctt tggggggcgg ggtctagcaa gagcagatat ctccggagca tttggataat     60
gtgacagttg gaatgcagtg atgtcgactc tttgcccacc gccatctcca gctgttgcca    120
```

| | |
|---|---|
| agacagagat tgctttaagt ggcaaatcac ctttattagc agctacttttt gcttactggg | 180 |
| acaatattct tggtcctaga gtaaggcaca tttgggctcc aaagacagaa caggtacttc | 240 |
| tcagtgatgg agaaataact tttcttgcca accacactct aaatggagaa atccttcgaa | 300 |
| atgcagagag tggtgctata gatgtaaagt tttttgtctt gtctgaaaag ggagtgatta | 360 |
| ttgtttcatt aatctttgat ggaaactgga atggggatcg cagcacatat ggactatcaa | 420 |
| ttatacttcc acagacagaa cttagtttct acctcccact tcatagagtg tgtgttgata | 480 |
| gattaacaca tataatccgg aaaggaagaa tatggatgca taaggaaaga caagaaaatg | 540 |
| tccagaagat tatcttagaa ggcacagaga gaatggaaga tcagggtcag agtattattc | 600 |
| caatgcttac tggagaagtg attcctgtaa tgggactgct ttcatctatg aaatcacaca | 660 |
| gtgttcctga agaaatagat atagctgata cagtactcca tgatgatgat atttggtgac | 720 |
| agctgtcatg aaaggctttc ttctcaagta ggaatttttt cttttcataa aagctgggat | 780 |
| gaagccagat tcccatct | 798 |

```
<210> SEQ ID NO 9
<211> LENGTH: 169
<212> TYPE: DNA
<213> ORGANISM: homo sapiens

<400> SEQUENCE: 9
```

| | |
|---|---|
| aaacagcgac aagttccgcc cacgtaaaag atgatgcttg gtgtgtcagc cgtccctgct | 60 |
| gcccggttgc ttctcttttg ggggcgggggt ctagcaagag cagatatctc cggagcattt | 120 |
| ggataatgtg acagttggaa tgcggtgatg tcgactcttt gcccaccgc | 169 |

```
<210> SEQ ID NO 10
<211> LENGTH: 176
<212> TYPE: DNA
<213> ORGANISM: homo sapiens

<400> SEQUENCE: 10
```

| | |
|---|---|
| aaaacgtcat cgcacataga aaacagacag acgtaaccta cggtgtcccg ctaggaaaga | 60 |
| gaggtgcgtc aaacagcgac aagttccgcc cacgtaaaag atgacgcttg atatctccgg | 120 |
| agcatttgga taatgtgaca gttggaatgc agtgatgtcg actctttgcc caccgc | 176 |

```
<210> SEQ ID NO 11
<211> LENGTH: 30001
<212> TYPE: DNA
<213> ORGANISM: macaca mulatta
<220> FEATURE:
<221> NAME/KEY: misc_feature
<222> LOCATION: (26113)..(26155)
<223> OTHER INFORMATION: n is a, c, g, or t
<220> FEATURE:
<221> NAME/KEY: misc_feature
<222> LOCATION: (28797)..(29186)
<223> OTHER INFORMATION: n is a, c, g, or t

<400> SEQUENCE: 11
```

| | |
|---|---|
| aatctctaag caattttttg gggaagaaag aattgcaatt agggcatacg tgtagatcag | 60 |
| atggtcttcg gtatatccaa cgacaaagaa aaggtgggag gtttcgttaa aaaagagaaa | 120 |
| tgttacatag tactttagga gaaaattcac tggcactatt aagggtctga ggagctggta | 180 |
| agtttcaatt ggtgagtgat ggtggtagat aaaattagag ctgcagcagg tcatttcagc | 240 |
| aactatcaga taaaactggt ctcaggtcac aacgggcagt ttcagcagct agacttgaaa | 300 |

```
gaattacact gcgggagcaa tgtcatttgt cctgcatgct tttctacccc ctaccccac      360 ttttttagtt gggtataaca agaacgaccc aaattgtatg atcaactttc acaaagcata     420
gaacagtagg aaaagggtct gtttctgcag aagatgtaga cgttgagagc cattttatgt    480
atttatttct ccctttcttc atcggtgaat gattaaaatg ttctgtatga ttttagtga     540 tgagaaaggt taaacgccac tcatctgtag taagtgtaat ctacacactt gcagaccaaa    600
aggcataagg tttaaaaaac ctttgttttt ttacacatca aacagagtgg tataaatgct    660
actcatctgt agtaagtgaa atctatacac ctgcagacca acgacgcaag gtttcaaaaa    720
tctttgtgtt ttttacacat caaacagaat ggtacatttt tcaaaagttt aaaaaaaaaa    780
aaaatccaca tatcacaact agcaaaaatg acattcccca gtgtgaaaat catgcttgag    840
agaattctta catgtaaagg caaaattgca gtgactttac aagggacctg ggattcccg     900 cccacagtgt ggagctgtcc cctaccaggg tttgcggcgg agttttgaat gtacttaaca    960
gtgtctcacg gtaaaaacaa aacttcatcc accaaatatt tgttgagcgc ccactgcctg   1020
ccaagcacaa acaaaaccat tcaaaaccac gaaatcgtct gcactttctc cggatccagc   1080
agcctctgcg attaaggttt gcacacgcta ttgcgccaac gctcctccag agcgcgtctt   1140
aagataaaag aatgggacaa gttgcccctc ccctttcac gggcctcgtg cgtcaacgtc    1200
atcgcatata gaaaacacac agacgtaacc tacggtgtcc cgctaggaaa gagaggcgcg   1260
tcaaacagcg acaagttccg cccacgtaaa agatgacgct tggtgcgtca gccgtccctg   1320
ctgcccggtt ccttctctct gggggcgggg cctggctaga gcaggtgtgg gtttaggagg   1380
tgtgtgtttt tgttttttcct accctctccc ctctacttgc tctcacagta ctcgctgagg  1440
gtgaacaaga aaagacctga taaagattaa ccagaagaaa acaaagaggg aaacaactgc   1500
agcctgtagc gggctctgga gcttaagaga ggcgcgctag gcgccgggcc gtgggcgtgg   1560
tcgggcgggg gtcgggccag gggcggggct gcggttgcgg tccctgcgcc cgcggcggcg   1620
gcggcggcgg cagcggaggc gcaggcgtg gcgagtgggt gagtgaagag gcggcgtcct   1680
ggcgggtgtc tgtttggcgt ccggttgccg ggaagagacg cgggtagcag ccggggctct   1740
cctcagagct cgacacattt ttactttccc tctcgtttct ctgaccgaag tcgggtgtcc   1800
ggctttcgcc tctagcgact ggtggaattg cctgcatctg ggccccgggc ttcgcggcgg   1860
cgcagggacg agggatggga atctggcctc ttcctcgctt tcccgcccgc agtgcgctgc   1920
cccagctgtc tccttcccgg ggacctgctg ggagcgctgc cgctacagac tcgagagaaa   1980
ggagcctcgg gcactgagag gcctcgcccg ggggaaggcc ggagggcggg cggcgggcgg   2040
cgagcggctc ctgcggacca agtctgggtt ctctgggaac ccgagacggt ccctgatggc   2100
gaggagatca tgcggggtgc tatggggtg tggagacgtc tgcagaattt tagcccaagc   2160
ttctaaggag tgctgatgac ttgcatatga gggcagcaat gccagtcggt gtactcccta   2220
ttctgtggga catgatgtgg ttgcttcaca gctccgagat gacacagact tgcttaaagg   2280
aagtgaccat tgtgacttgg gcatcacttg actgatggta atcagttgca gacagaagtg   2340
cacagattac atgtctgtgt ccacactgga tcagtctggc cacgaggaac accacaggct   2400
ttgtattgag aaacaggagg gaggtcctgc actttcccag gaggggtggc cctttcagat   2460
gcaatcgaga ttgttaggct ctggtagagt ggttgcctgg ttgtggcagt tggcaaattc   2520
ctattcaaac tgttgccgtg cgtcaccagt taacaacaag ggtacacgat ctgtctggca   2580
ttacttctac tttgtacaaa ggatcaaaaa tactgttaga tatgattttt ctcagacttt   2640
gggaaacttt taacgtaatc tgtgaatatc acagaagcaa gactgtcata tagaggatat  2700
```

```
taataacctg gagtcagaat acttgaaata tggtgtcatt tgacacgggc tctgttatca   2760
ccacctttgc caagccctt  cacttgagga aaaccctcaa tcagttggaa actgcctcat   2820
gctgacagta catctgaaac aaaaacgaga gtagttacca cattccagat tgttcactaa   2880
ggcagcattt atctgctcca ggaaaacatt acaagcaact tatgaagttg ataaaatatt   2940
ttgtttggct atgttggtac tccaaaagtt gctttcagag aaacaaagta aaccaaggag   3000
gacttctgtt gttcacgtct gcccttgggc tctattctac gttaattagg tagttcccag   3060
gaggactaga ttagcctacc tattgtctga gaaacttgga tctgtgagaa atggccagat   3120
agtgatacga acttcacctc ccagtctttc ctgatgttta agattgagaa agtgttgtga   3180
actttctggt gctgtaagca gttcactgtc cttaaagtgg tcctgggcag ctcctgttgt   3240
ggaaagtgga ccgatttagg attctgcttg gctttggact gggagaaaat aaactgcatg   3300
gttacaagta ttgagagcca agttggagaa ggtggcttac acctataatg ccagagcctt   3360
aggaggcagg ggcaagagga tcactggaag tcaggagttc aagcccaacc tgggcagcct   3420
agaccctgtc tctacaaaaa attaaaaact tagccgggcg cggtggtgtg cacctgtagt   3480
cctagctact gggaggctg  aggcaggagg gtcttttgag cccaggagtt tgaagttaca   3540
gggagctatg atcctgccag tgcactccag cctggatggc aaaacgagac cctgtctcta   3600
aaaaacaaga agtgagggct ttatgatcgt agaaattttg cttacaatag cagtggacca   3660
accacctttc taaataccaa tcagggaaga catagttgat ttttaacaaa catttaaaga   3720
aaaagcaaaa cctcaaactt agcactctac taacagtttt agccgatgct aattaaggta   3780
atcatgtctg catatatggg attactttca gaaagtgtat tgggaaacct ctcatgaacc   3840
ctgtgcaacc ctgagcaagc caccgtctca ctcagtttga atcttggctt ccctcaaaag   3900
actctgtggc taatgtttgg taactctctg gagtagccag cactgcatgt acataggata   3960
ggtacataaa acaattattg gttttgagct gattttttc  agctgcattt gcgtgtatgg   4020 attttctca ccaaagacaa tgacttcaag tgttaataaa ataattgtac agctctccta   4080
attatacttc tctgtaacat ttcatttctc agactatttc ttttggtagg atttaaaact   4140
aaacaattca gtatgatctt tgttcttcat tttctttctt attcttttt  ttttcgagac   4200 agagtctccc tctgttgtgc catctcagcc cattgcaacc tccgccacct gggttcaagt   4260
gattctcctg cctcagcctc ctgagtagct gggattacag gtgcccgcca ccacacctac   4320 ctaattttt  gtattttag  tagaggcggg gtttcaccat gttggctagg ctggtcttaa   4380
actcctgacc tcagatgatc cacctgcctc ggcctcccaa agagctggga tgataggcgt   4440
gacccaccat gcccgcccca ttttttttct tattctgtta ggagtgagag tgtaactagc   4500
agtctataat agttcaattt tcacaacgtg gtaaaaattt tccctgtaat tcaacgagat   4560
tttgcttcag ggctcagttc tgttttagga atacttttta ttttcagttt gatgatgaaa   4620
tattagagtt gtgatattgc ctttatgatt acctaccttt ttaacctaaa agaatgaaag   4680
aaaaatatgt ttacagtata attgtatggt tgcgtgttaa cttaattcat tatgttggcc   4740
tccagtttgc tgttgttcgt tatgacagca gtagtgtcat taccatttca attcagatta   4800
cattcctgta tttgatcatt gtaaactgat tgcttaaatt gtattaaaaa cagtggatat   4860
tttaaacaag ctgtactgct tatatccagt gctgtctcct aagactatta aattgatata   4920
acatatttaa aagtaaatat ttcctaaatg aattttgaa  attaaaaata cacgtgttaa   4980
aactgtcttt gtgttcaacc atttctgtac gtacttagag ttaactgttt tgccaggctc   5040
```

-continued

```
tgtatgccta ctcataatgt gataaaagca ctcatctaat gctctataaa tagaagtcag    5100
tgctttccat cagactgaac actcttggca agatgtggat aaaattattt aagtaaaatt    5160
gtttactttg tcatacattt acagatcaaa tgttagctcc caaagcaatc atatggcaaa    5220
gataggcata tcataatttg cctattagct gctttgtatt gctattatga tagatttcac    5280
agttttagat ctgcttagat gaaaatgtaa ttcttttttac tgtcagtctt agatataagt    5340
cttcaattat agtacagtca cacattgctt aggaatgcat cattaggcga ttttgtcatt    5400
atgcaaacat catagagtat acttacataa acctatatag tacagccttt acgtacgtag    5460
gccatatggt atagtctatt gctcctaggc tacaaatctg tacagctgtt actgtactga    5520
atactataga cagttgtaac acagtggtat ttatttatct aaatatatcc aaacatagaa    5580
aaggtacagt taaagtatgg tataaaaaat aatgatatac ctatataggc cacttaccgt    5640
gaatggagct tgcaggacta aagttgctc tgggtgagtc agtaagtaag tggtgaatga    5700
atgtgaaggc ctagaacatt actgtacaca ctgtagactt tataaacaca gtatgcttaa    5760
gctacaccaa atttatcttt acagttttc ttcaataaaa aattaatgtg aacctactat    5820
aactttttaa ctttgtaaac ttttttaattt tttaactttt aaaatactta gcttgaaaca    5880
caaacacgca tagctataca aaaatatttt ttctttatat ccttattcta gaagcttttt    5940 cctatttta acttttttt ttttacttgt tagtcgtttt tgttaaaaac taaaacacac    6000
acactttcac ctaagcatag acaggattag gatcatcagt ttcactccct tccacctcac    6060
tgccttccac ctccacatct tgtcccactg gaacgttttt aggggaata acacacatgt    6120 agctgtcacc tgctatgata acagtgcttt ctgttgaata cctcctgaag gacctgcctg    6180
aggctgtttt acatttaact taaaaaaaaa aataagtaga aggagtacac tctaaaataa    6240
caataaaagg tatagtctag tgaatacata accagcaac atagtagttt attatcaagt    6300
gttgtatact gtaataattg tatgtgctat actttaaatg acttgaaaaa ttgtactaag    6360 acctgttatgat ggttacagtg tcactaaggc gatagcatat tttcaggtcc attgtaatct    6420
aatgggacca ccatcatata tgcagtccac cattgactga aatgttacat ggtacgtaac    6480
tgtatttgca agaatgatttt gttttacatt aatatcacat aggatgtacc tttttagagt    6540
gatatgttta tgtggattaa gatgtacaag tggagcaagg ggacaagagc ccttggttct    6600
gtcttggatg tgagcttta tgctcttctc atcatgtctg ttttcttatt aaattcaaag    6660
gcttggacag gccctattta gcccttgttt tctatgtgtt ctaaataact aaagcttta    6720 aattctagcc atttagtgga gaactctctt tgcaatggta aaatgctgta ttggtttctt    6780
gactagcata ttaaatatat ttatctttgt cttgatattt caatgtcatt ttaaacatca    6840
ggattgggct ttagtattct cataccccaga gagttcactg aggatacagg actgtttgcc    6900 catttttgt tatggctcca gacttgtggt atttcgatgt cttttttttt tttttttttt    6960
tttaaccttt tagcagcttt aaagtatttc tgttgttagg tgttgtatta cttttctaag    7020
attactgtaa caaagcacca caaactgagt ggctttaaac aacagcaatt tattctctca    7080
caattctaga agctagaagt ccgaaatgga agtgttgatg gggcatgatc ctcaaaagag    7140
agaagactct ttccttgcct cttcctggct tctggtggtt accagcaatc ctgagcgttc    7200
ctttcttgct tcgtagtttc agcagtccag tatctgcctt ttgtcttcac atggatgtct    7260
accccttgtc tctgtgtctc cagatctctc tccttataaa cacagaagtt actggattag    7320
gccccactct aatccagtat gaccccattt taacacgatt acacctattt ctaaataagg    7380
tcacattcac atataccaag ggttaggaat tgagcatatc ttttgcaggg acacaattca    7440
```

```
acccacaagt gtcagtctct agctgagcct ttcccttcct ggttttctcc tttttagttg   7500
ctgtgggtta ggggccaaat ctccagtcat actagacttg cacatggact ggagatttgg   7560
gaatactgcg ggtctattct atgagcttta gtatgtaaca tttaatatca gtgtaaagaa   7620 gccattttt cagttcacta tttctttgaa tttcttaatg tatgccctga ataagtaa     7680 caagttacta tgtctcataa aatgatcata tcaacaaaca tttaatgtgc acctactgtg   7740
ctagttgaat gtctttatcc tgataggaga taacaggctt ccgcatcttt gacttaagag   7800
gacaaaccaa gtatgtctga atcatttggg gttttgatgg atatctttaa attgctgaac   7860
ctaatcattg gttttatatg tcattgttta gatatctcag gagcatttgg ataatgtgac   7920
agttggaatg cagtgatgtc gactcttttgc ccaccgccat ctccagctgt tgccaagaca   7980
gagattgctt taagtggtga atcacccttta ttagcagcta cttttgctta ctgggacaat   8040
attcttggtc ctagagtaag gcacatttgg gctccaaaga cagaacaggt acttctcagt   8100
gatggagaaa taacttttct tgccaaccac actctaaatg gagaaatcct tcgaaatgca   8160
gagagtggtg ctatagatgt aaagtttttt gtcttgtctg aaaagggagt gattattgtt   8220
tcattaatct ttgatggaaa ctggaatggg gatcgcagca catacggact atcaattata   8280
cttccacaga cagaacttag tttctacctc ccacttcata gagtgtgtgt tgatagatta   8340
acacatataa tccggaaagg aagaatatgg atgcataagg taagtgattt ttcagcttat   8400
taatcatgtt aacctatctt ttgaaagctt attttctgat acatataaat cttatttta    8460 aattatatgc agtgaacatc aaacaataga tattatttat tttgcattta tcctgttaga   8520
tacaaataca tctggtctga tgcctgtcat cttcatatta actgtggaag gtaggaaatg   8580
gtagctccac attacagatg aaaagctaaa gcttaaacaa atgcagaaac ttttagatcc   8640
tggattcttc ttgggagcct ttgactctaa tacctttttgt ttccctttca ttgcacaatc   8700
ctgtctttcg cttactacta tgtgtaagta taacagttca aaaaaatagt ttcataagct   8760
gttggttatg tagcctttgg tctctttaac ctctttgcca agttcccagg ttcataaaat   8820
gaggaggttg aaccgcatgg ttcccaagag aattccttt aatttacag aaattattgt    8880 tttccccgaa gtcctatagt tcaatatata atgatattta catttcagta tagttttggc   8940
atatctaaag aacacattaa gttctccttc ctgtgttcca gtttgatact aacctggaag   9000
tccattaagc attaccaatt ttaaaaggct tttgccccaat agtaaggaaa aataatatct   9060
tttaaaagaa taatttttta ctatgtttgc aggcttactt ccttttttct cacattatga   9120
aactcttaaa atcaggagaa tcttttaaac atcataatgt ttaatttgaa aagtgcaagt   9180
cattcttttc cttttgaaa ctatgcagat gttacattga ctattttctg tgaagttatc    9240 tttttttcc ctgcagaata aagggtgttt tgattttatt ttgtgttgtt tataagaaca    9300
tacattcgtt gggttaattt cctgcccctg ccccgtttt ttccctaaag tagaaagtat    9360
ttttcttgtg aactaaatta ctacacaaga acatgtctat tgaaaaataa gtatcaaaat   9420
gttgtgggtt gtttttttaa ataaattctt tcttgctcag gaaagacaag aaaatgtcca   9480
gaagattatc ttagaaggca cagagagaat ggaagatcag gtatatgcag attgcatact   9540
gtcaaatatt attctcatgg catgtatctg tgtaaagttg atggctacat ttgtgaaggc   9600
cttggggaca tacagagtaa gccttaatgg agcttttatg gaggtgtaca gaataaacta   9660
gaggaagatt tccatatctt agacctgaag agtaaaatca gtaaacaaag gaaaatagta   9720
attgcatcta caaattaata tttgctccct ttttttttct gtttgaacag aataaatttt   9780
```

```
ggataacttg ttactagtaa aaaatttaaa aattgtctgt gatatgttct ttaaggtact    9840
acttctcgaa cttttttccta gaagtagctg taacaggagg agagcatatg tacccctaag    9900
gtatctgggg tataggccca tgtccaaaca atatttcttt taagtcttgt gttgtatctt    9960
taagactcat gcaatttaca ttttattcca tgatataact attttaatat taaaatttgt   10020
cagtgatatt tcttaccctc tcctctagga aaatgtgcca tgtttatact ttggctttga   10080
gtgcccctga ggaacagaca ctagagtttg agaagcatgg ttacacaggc gtggcttccc   10140
ctgcagaaat taagtacaga ctatttcagt gtaaagcaga gaagttcttt tgaaggggaa   10200
tctccagtga agaaagggtt cttcactttt acttccattt cctcttgagg gtgaccctca   10260
ttgctccttg taaaactccg atattttaaa catggctgtt ttgctttcct ctggttctttt   10320 ttaacatgag tgagacagat gatactttaa aaagtaattt taaaaaaaag tgttaaaata   10380
tatggccata atgcagaacc ctatgctgtg atctccttta ccaaattgtt gtgtttgtac   10440
ttttgtagat agcttccag tccagagaca gttattctgt gtaaaggtct gactcaacaa   10500
gaaaagattt ccctttaccc aaagaatgcc agtcttatt tgctggtcaa taagcagggt   10560
ccccaggaaa ggggtaactt tcaccaccct ctaacccact ggttattagt aaactaatta   10620
agtagactta tctcaagatg aggaaactta aaaccaagta aaattctgct tttactggga   10680
tttttatttt tgaaaccaga aacgttact taagttgact actattaatg aattttggtc   10740
tctcttttaa gtactcttct taaaaatgtt atcctactgc tgagaagttc aagtttgaga   10800
agtacaagga ggaatagaaa cttgagagat tttcttttc ttttagagcc tcttctgtat   10860
ttagccctgt aggaattttt ttttttccccc aagattcttc ttcgtgaaaa ggaggagttg   10920 cctttttgatt gagttcttgc aaatctcaca acgactttat tttgaacaat actgtttggg   10980
gatgatgcat gagtctgaaa caacttcagt tgtagctgtc atctgataaa attgcttcac   11040
agggaaggaa atttagcacg gatctagtca ttattcttgt tagattgaat gtgttaatca   11100
taattgtaaa caggcatgat aattattact ttaaaaactg aaaacagtga atagttagtt   11160
gtggaggtta ctaaagcatg attttttttaa aataaaactt tcagcatttt gcaaatatgc   11220 atatggtttta ggatagaact tccagaggta gcatcacatt taaattctca agcaacttag   11280
taatacgagg ctctgaaaaa ctggttaaag ttactccaga aatggccctg ggtctgacag   11340
acattctaac ttaaagatgc atatgaagac tttgaataaa atcatttcat atgaagacat   11400
tgaataaaat catttcataa aataagtgag gaaaaacaac tactattgaa ttcatcttaa   11460
tgtatgattt taaaaatatg tttagctaaa aattcataga catttgacaa tttcgtttat   11520
atctcaaaaa gttgacttac ccaagttgat cacaaaactg atgagactgg tggtggtagt   11580
gaataaatga gggaccaccc atatttgaga cactttacat ttgtgatgtg ttatactgaa   11640
ttttcagttt gattctataa actaccaatt tcaaaattac aatttcaagg tgtaataagt   11700
agtggtatta tcttgaaata ggtctaaagg gaacttttct gttttaaaat attcttaaac   11760
tatatgtgct gattttgatt tgcatttggg tagattatac tcttatgaat cgggggggctg   11820 ggtattgatt caggttttcc ttacctattt ggtaaggatt tcaaagtctt tttgtgcttg   11880 atttttcctcg ttttttaaata tgaaacatat tgatgacttt taattaacaa atgtttttat   11940
ctcgaataaa ttttaaagga gatcttttct aaaagaggta tgatgactta attattgcat   12000
ataacaataa atgagaaacc agtgattcca tactctctaa agaataaaag tgagctttag   12060
gcccaggcat ggtggctcat gcctgtaatc ccagcacttt ggaaggccga ggcaggcgga   12120
tcacctgagg tcaggaattc gacaccagcc tggccaaatg gcaaaaccct gtctctacta   12180
```

```
caaatacaaa aattagctgg gcatggtggc agcccctata gtcccagcta cttggaagac    12240
tgagacagga gagtcactcg aacccgagag gcagaggttg cagtaagctg aaatcacacc    12300
attgcactcc agcctgggca acaagagcaa aactccgtct caaaaaaaaa aaaaaaaaaa    12360
aaaaagaata aaagtgagct ttggattgcg tataaatcct ttagacaagt agtagacttg    12420
tttgatactg tgtttgaaca aattacaaag tattttcatc aaagaatgtt attgtttgct    12480
gttattttta ttttttattg cccagcttct ctcatattca ttatgtgatt ttcttcactt    12540
catgttactt tattgtgcag ggtcagagta ttattccaat gcttactgga gaagtgattc    12600
ctgtaatgga actgctttca tctatgaaat cacacagtgt tcctgaagaa atagatgtaa    12660 gttttatat ttttaaatga gagcaattat acccttatc agttttttgg ggttatatta    12720
ttattatgta tattattaat attctaattt taatactaag cacttcgtcg tacgtactat    12780
ccacatgcag tattagccac ttgaacagat aagcacacac aaaatcctgg attttatggc    12840
ataacagagg catttttgat cagtgatgac aaaactaaat ttattttgtt tatttcacta    12900
cttttataat tcctaaaagt gggaggatcc cagctcttat aggagcaatt aatatttaat    12960
gcagtacctt ttgaaacaaa actgtgtgcc aaagcagtaa ccattaatgg aagttgactt    13020
atagtcacaa atttagtttc cttaatcatt tgttgaggat gttttgaatc acacactatg    13080
agtgttaaga gatatcttta ggacactatt cttgttgttt tattgtcatt taggttagtc    13140
tcctgtctga cagctcagaa gaggaagttg ttcttgtaaa aattgtttac acaacctgat    13200
tgaccagctt tcacatttgt tcttctgaaa gctgatggta gtgcacagat tgtttttatgg    13260 ggagtcttga ttctcagaaa tgaaggcagt gtgttatatt gaatccagac ttcagaaaac    13320
ttgtatatta aaagtgtttt ttcaacacta tgttatagcc agactaattt ttttatttt    13380 ttgatgcatt ttagatagct gatacagtac tcaatgatga tgatattggt gacagttgtc    13440
atgaaggctt tcttctcaag taagaatttt tcttttcata aaacctggat gaagcatatg    13500
ttcacctatg acaagatttg gaaggaagaa aataacagac tgtctactta gattgttcta    13560
gggacaacat tgcatatttg aattgttgct taaattgtg ttatttttca ttcgttatat    13620
ttctataata tatttgatgt tattccattt gctatttaaa gaaactgagt ttccatattt    13680
cccagacaag aaatcatggc cccttgcttg attctggttt cttgtttac ttctcattaa    13740 agctaaaaga accctttcaa attaagttgt actgtagatg aacttaagtt atttaggcct    13800
agaaaaaaaa aattcatatt tatactgatc ttttttccatc cagcagtgga gtttagtact    13860
taagagtttg tgcccttaaa ccagactccc tgggttaatg ctgtgtacct gtgggcaagg    13920
tccctgaatt ctctatacac ctatttcctc atctgtaaaa tggcaataat aataatagta    13980
cctaatgtat agagttgtta taagcattga gtaagataaa taatataaag cacttagaac    14040
agtgcctgga acataagaac acttaataat agctaacatt ttctatttac atttcttcta    14100
aggaaaaggt taacagaaat agccaatatt tgttcagtgc ctacatgtta gttcctatac    14160
taagtgcttt acatgtatta tcttatattc tattttaatg tttcttcaca gttgcagatt    14220
atcatgaaat tttattttt aaaaaagaga agtaaaagga taaagtattc acttttatgt    14280
ccacagtctt ttcctttagg ctcatgatgg agtatcagag gcatgaatgt gtttaaccta    14340
agagccttaa tggcttgaat cagaagcact ttagtcctgt atctgttcag tgtcagcctt    14400
tcaaacatca ttttaaatcc catttgactt taagtaaatc acttaatctc tctacatgtc    14460
aatttcttca gctataaaat gatggtattt caataaataa atacattaat taaatgatat    14520
```

```
tttacaaact aattgggctg ttttaaggct caataagaaa atttctgtga aaggtctcta   14580
gcaaatgtag ggttctatac aaataaaaga taacattatg cttatatctt cggtgtttat   14640
catgcaaagc tcttctgagt tttttgaaga gctcacctac tattttttgt ttttagtttg   14700
ttaaattgtt ttataggcaa tgttttaat ctgttttctt taacttacag tgccatcagc    14760
tcacacttgc aaacctgtgg ctgttccgtt gtagtaggta gcagtgcaga gaaagtaaat   14820
aaggtagttt attttataat ctagcaaatg atttgactct ttaagactga tgatatatca   14880
tggattgtca tttaaatggt aggttgcaat taaaatgatc taatagtata aggaggcaat   14940
gtaatctcat cgaattgctg agacaacttg tggcaacagt gagtttgaaa taaagtgaat   15000
aggagtcatt tatcagttta ttttgataac ttgtaaatac cagtgtcaga tgtgtataaa   15060
tggttttgag aatatattaa aatcaggtat ttaaaaaaac actattcttc tatttcccaa   15120
tgtaatcttt aacaaatctg aaggtagtca tgtactttcg gtactagttc tgaagaaatg   15180
ttatttgttt attcatcttg atttcattgt cttggctttc cttctaaatc tatcccttct   15240
tgggagctat tgggattaag tggtcattga tgattatact ttattcagta atgtttctga   15300
cccctttcct tcagtgctact tgagttaata aaggattaat gaacagttac atttccaagc   15360
attagctaat aaactaaagg attttgcact tttcttcact gaccattagt taaaaacagt   15420
tcagagataa gtacatgtat ctttcaattc tagcaaacct aattttttaa aagaagttt   15480 acataggaaa tatgttggaa atgattattt actttacaaa gatattcata atttattttt   15540
tctgtaacta gctactttgt atatttacat gagccttaat ttatcaaaat tatatttctc   15600
atataaccat ttatgagagc ttagtattcc tctgtcatta tattgcgtct acggactagt   15660
gatcttacta cttctgttac ctcgaacaag tggcttcccg tctgtgacct ccaaagccgt   15720
aggttccaca gagtgactgc tgagctgctt tatgaaggga gaaaggctcc atagttgggt   15780
ttttggtttt gcttttgttt ttgttttaa cattttttcct atcctccatc ctcttgaggc    15840
agagtagctt acctttatc ttgttttaat ttgagaaaga agttgccact gctctagatt    15900
gaaaaccact gctttaacat aataactctg aatatggttt gaatttcaag atagtgacat   15960 gccttttat ttttactaat agagctgtag gtcgaatatt attagatttc taaaccccac    16020
ccaatgacct cctttattta aatcaaattt aataattaat tatcttctta ttggaggatc   16080
tggacattct ttgatgtttc ttacaatgaa tttcacatgt agacccacta aacagaagtt   16140
ataaaggttc catggtcaaa taagtctgag aaagtctgca tattatataa ttcacctaaa   16200
gagtcacagt atgtacccaa atgttaaagg ttttgagatg ccatacagta aatttaccaa   16260
gcattttcta aatttatttg accacagaat ccctatttta agcaacaact gttatatccc   16320
ataggttcca ggtgactaaa gaatacttat tgcttaggat atgttttatt gataataaca   16380
attaaaatgt cagatatctt tcataagcag atcagtggtc tttttaaaac tttgtatttt   16440
aatgctaaaa tctttctttt tgtagatagt cagaacatta tgccttttt tgactgcagc   16500 agagagaaaa tgctccaggt tatgtgaagc agaatcatca tttaaatatg agtcagggct   16560
ctttgtacag ggcctgctaa aggtatagtt tctacttatc acaagggaaa ccaatttcct   16620
aaaatcattt tgagactct ttgtagacaa atattaaata ttagcattta atgtatctca    16680
tattgacatg cccagtgact gacttccttt gcacagttct gcgcatagac tatatgtctt   16740
atggatttat agttagtatc atcagtgtaa caccatagaa taccctttgt tttccaggtg   16800
ggtccctgta cctacatgtc tagcatcagg tgttgttttt ttttttttt tttaaaacat    16860 atgcttaaat caggttgcac atctaaaata agatcatttc tttttaacta aatagatttg   16920
```

```
aattttattg aaaaaaattt taaaacatct ttaagaagca tataggattt aagcagttac   16980
tatgtatgtg tactaaaata tatatatatt cctaaatata tattcctata tataatatat   17040
gtatttctat atataatata tattagaaaa aacttagagt tttctttcat ttgagtctac   17100
tgttcaagga gcaaaacaga gaaatgtaaa ttagcaatta tttacaataa ttaaagggaa   17160
gaaagttgtt caccttgttg gatctattat tgttgtttta attatagtcc caagacgtga   17220
agaaatagct ttcctaatgg ttatgtgatt gtctcatagt gactactttc ttgaggatgt   17280
agccacagca aaatgaaatt taaaaaattt aaaaattgtt gcaaataaaa gttatattag   17340
gcttttgtgc aatttcaata atgtgctgct atgaactcag aatgatagta tttaaatata   17400
gaaactagtt aaaggaaaca cagtttctat ttgagttata caaatctgta aattagaact   17460
tctcctgtta aggcattata aagtgcttaa tactttttgtt tcctcagcac cctctcattt   17520
aattatataa ttttagctct gaaagggacc tataccagat gtgtagagga aatttcaaaa   17580
ctatgatcta atgaaaaaat atttaatagt tctccatgca aatacaaatt atatagtttt   17640
ctggaaaata cctttgacat tatacaaaga tgattatcac agcattataa tagtgaaaaa   17700
atggaaatag cctctttctt ctgttctgtt cacagcatat ggcacagtac ctcatatgca   17760
gtaggttatt atgacctggt aactggctcc cccaactgat taggaaagaa gtaaatttgt   17820
tatttataaa aatacgtgtt cattgagatg catagaataa ttaagaaatt aaaagacact   17880
tgtaatttca aatccagtga atacccactg ttaatatttg gcatatctct ttctagtctt   17940
tttttccctt ttgcatgtat tttctttaag actcccaccc ccactggatc atctctgcat   18000
attctaatct gcttttttca cagcagattc taagcctttt tgcatatcaa cacaaacttc   18060
aacaacttca tctttagatg ctaaataatg aattcatttt tatttactta accactttct   18120
ttggatgctc aggttattct gatgttttgc cattaaaacc aatgctatac tgaacacttc   18180
tgtcactaaa acttgaacac actcatgaat aatttcttag gataaatttt tagagatgga   18240
tttgctaaat caaagaccat ttttttaaaa ttgaaaaaca attatatcgt ttggcatgta   18300
agacagtaca ttttccttttt attttgacag gattcaactg gaagctttgt gctgcctttc   18360
cggcaagtca tgtatgctcc atatcccacc acacacatag atgtggatgt caatactgtg   18420
aagcagatgc caccctgtca tgaacatatt tataatcagc gtagatacat gagatccgag   18480
ctgacagcct tctggagagc cacttcagaa gaagacatgg ctcaggatac gatcatctac   18540
actgacgaaa gctttactcc tgatttgtac gtaatgctct gcgtgctggt actgtagtca   18600
agcaatatga aactgtgtct tttatgaata aaaacaaaac agaagttgca ttcaaaagaa   18660
aagaaatatt actagcagaa ttatgcttga agaaacattt aatcaagcat tttttttctta   18720
aatgttcttc ttttccata cgattgtgtt taccctaaaa taagtaagat taaccccttaa   18780
agtgaatatt taactatttg tttaataaat atatattgag ctcctaagca ctgttctagg   18840
tactgggctt aatagtggct aaccacacag ctccagcccc tacattgcat atagtctatt   18900
gtataagtta ctgaatggac ttactaacaa aaccagagaa gtaattctaa gtcttttttt   18960
tcttgacata tgaatataaa atacaacaaa actggtaaaa tatattaata gagcattctt   19020
ttactttgca ttttatattg ttactcactt cgtatttaag aaaaacagtc tgatcaggaa   19080
attcaaaagg aaaagtaatg ataattaatt gagcatagac ccaacttgaa aagaaaaaaa   19140
aggatgatga taaatctata atcctaaaac cctaagtaaa cacttaaatg atgttctgaa   19200
atcaggaaaa gaattatagt atattttttgt ggttctctttt tattagttga aaaaaggcac   19260
```

```
agtagctcat gcctataaga acagagcttt gggattccaa ggcaggcaga tcacttgagg    19320
ccaggagttc cagaccagcc tgggcaacat agtgaaaccc catctctaca aaaataaaaa    19380
agaattagtt gaatgtgttt ctgtgtgcct ataatcctag ctattcagaa agctgaggca    19440
ggaggatctc ttgagcccag gagtttgagg ttacatggag ttatgatgtg ccagtgtact    19500
ccagcctgcg ggacaatgag actctgtctt gttaaaaaaa aaagtgcttg gaataatgtt    19560
tggcatatag aaggtaacaa cagtaaatgt taactgtaat aacccaggta taagtgtgta    19620
aggtgataga aaaattgggg caaacaaccc tgacctgtgt ctctacagaa taagtttgag    19680
ttgaggcaac agacatgtgg agcaccagta attacacact aaatgttaac caaaagcgtt    19740
gaatagtaac atcttattca agggacccca agccttatat atctcaaggt gcagaaagat    19800
gacttaatat aggacccatt ttttccgagt tctccagagt ttttattggt tcttgagaaa    19860
gtagtggggg aattgtttta gaaaatgaat tggtcaaact gaaattccat gtcagtaagt    19920
ttttacatat tggtaaattt tgatagacat gtagaagttt tctaattaat ctgcgccttg    19980
aaacattttc cttttttccta aagtgcttag tattttttcc cttttttgat tggttgcttg    20040
ggagcttttt tgaggaaatt tagtgaactg cagaatgagt ttgcaaccat ttagtatttt    20100
tgttttgtgt tttagaggag gtatgtgtat tttaacatttt cttaatcatt tttagccagc    20160
tatgtttgtt ttgctgattg acaaactata attaaacagc tattctcatt ttgctgatca    20220
tgacaaagta atatcctgaa ttttaaatt ttgcatccag ctctaaattt tctaaattt     20280 ctaaacataa aattgttcaa aaaatagtat ttttagccac tagattgtgt gttgttaagt    20340
ctgttgtcac agactcattt tacttttcag tgtgtgtttt tacatgttaa ttatgtttgt    20400 cattttaat tttaactttt taaaataatt ccagtcactg ccaaaacatg aaaaattggt     20460
cactggaaat tttttttta acttttattt taggttcatg tgtacatgtg caggtttgtt    20520
atacaggtaa attgcgtgtc gtgagggttt ggtgtaccca ggtaataagg gtagtaccca    20580
ataggtagtt ttttgatcct tacccttctc ccacccttct ttcacccctcg agtaggcctt    20640 ggtgttgctg tttccttctt tgtgtccatg tgtactcaat ggttagctcc tacttagaag    20700
tgagaacatg cggtatttgg ttttctgttc ctggattagt tcactcagga taatggcctc    20760
tagctccatc tgttttttat ggctgcatag tattccatgg tgtatatgta tcatgttttc    20820
tttatccagt ctaccattga tagacattta ggttgattct ctgtctttac tatcatgaat    20880
agcgctgtga tgaacatata cacatgcatg tgtccttatg gtggaacaat ttgtattcct    20940
ttaagtatat acagaataat ggggttgcta gggtgaatgg tagttctatt gtaagttatt    21000
tgtgaaatct tcaaactgct tttcacaata gctaaactaa tttacagtcc caccagcagt    21060
gtataagtgt tcccttttct ccacaacctt gccaacatgt tatttttta cttttcaata    21120 ataggcattc ctagagaatt gatttgcaat tctctaatga ttagtgatat tgagcatttt    21180
ttcgtatgct ttttagctgt gtgtatatat tcttttgaaa aatgttaatg tcctttgccc    21240
agtttgtaat ggggttgttt gttttttgctt gttaattaaa gttccttcca gattctggat    21300
atccctttgt cagatgcgtg gtttgcagat atttttctcc ccttgtgtag ttgtcttttt    21360
tactctgttg atagtttctt ttgccgggca ggagctcatt aggtctcatt tgtgtttgtt    21420
tttgttgcag ttgcttttgg cgtcttcatc ataaaatctg tgccagggcc tatgtccaga    21480
atggtatttc ctagttttgtc ttccagggtt tttacaattt tagattttac gtttatgtct    21540
ttaatccgtc ttgagttgat taaggaaggg gtccagtttc actctaattc ctatggctaa    21600
caattatccc agcaccattt attgaatacg gagtcctttc cccattgctt gttttttgtca    21660
```

```
attttgttga agatctgatg gttgtaggtg ctatgtggct ttatttcttg gctctctatt   21720
ctccactggt ctgtctgttt ttataccagt accctgctgt taaggttcct atagccttt    21780
agtataaggt cggctaatgt gatgcctcca gctttgttct ttttgcttag gattgctttg   21840
gctatttggg ctccttttg gttccatatt aattttaaaa tagttttttc tagttttgtg    21900
aagaatgtca ttgatagttt agaggaatag cgttgaatct gtagattgct ttgggcaaat   21960
ggccatttta acaatattga ttcttcctat ctatgaacat ggaatgtttt tccatgtgtt   22020
tgtgtcatct ctttataccct gatgtataaa gaaaaaccag tattattgct actcaatctg  22080
ttccaaaaaa ttgaggagga ggaactcttc cctaatgaga ccggcttcct tctgatacca   22140
aaacctggca gagatacaac agaaaaaaga aaacttcagg ccaatatcct tgatgaatat   22200
agatgcaaaa atcctcaaca aaatactagc aaccaaatcc agcagtacgt caaaaagcta   22260
atctacttta agtaggcttt atccctggga tgcaaggttg gttcaacata cacaaatcaa   22320
taagtgtgat tcatcacata aacagagcta aaaacaaaaa ccacaagatt atctcaatag   22380
gtgcagaaaa ggcttttcaat acaatttaac atccttcatg ttaaaaacct tcagtaggtc  22440
aggtgcagtg actcacacct gtaatcccag cactttggga ggccaaggcg gacgtatatc   22500
ttaagcccag gagttcaaga ccagcctagg cagcatggtg aaaccccatc tctacaggaa   22560
aaaaaaaaaa aaaaaaaaa aaaaaaaaaa agcttaatat ggcggcatgc acctatagtc    22620
ccagctactc aggaggttga ggtggggagga ttgcttgagc ccaggaggca gaggttgcag  22680
cgagctgaga tcgtgccact gcactccaac ctgggcaata agtgagacc ctgtctcaaa    22740
aagaaaaaca aaaataatcc taaaccaact aggcattgaa ggaatatgcc tcaaaaaaat   22800
aagaaccatc tatgcagac ccacagccaa tatcttacca aatgggcaaa agctggaagt    22860
attctccttg agaaccgtaa caagacaagg atacacactc tcatccctcc ttttcagcat   22920
agttctggaa gtcctcgcca gagcagtcag gaaagagaaa gaaagaaaag gcattcagat   22980
aggaagagaa gaagtcaaac tatttctgtt tgcaggcagt ataattctat acctagaaaa   23040
tgccatagtt tctgcccaga agctcctaca tctgttaaaa atttcagcaa agttttagca   23100
ttgtctgtat tccaacagct tccagggtga gagtgaaatc aggaacacag tcccgttcac   23160
aatagccgca aaaagaataa ataccttgg aatccagcta accagggagg tgaaacatct    23220
ctacgagaat tacaaaacgc tgctgaaaga atcagagat gacacaaaca aatgaaatg     23280
ttgttttaa caccttgctt tatctaattc acttataact aagatattca ttcagtggaa   23340
caggtataat aagaccactc gacttaaata taagccttat tctctttcca gagcccaaga  23400
aggggcacta tcagtgccca gtcaataatg ataaaatgct gatatttttc cccttttactg  23460
tttctttctt ctgtagtgtg gtacactcat ttccttaagat tagaaaactt gacctacctt  23520
cctgtttgct tctacacacc cccattctct ttttttgcca ctccggtcag gtataggatg   23580
atccctacca cttttagtta aaacctcctt cccttattaa atgttctctt accactctgg   23640
cctgagtaga acctagggaa aatggaagag aaaagatgaa agggaggtgg gggctgggaa   23700
gggaatagtc ttgtttgtgt gtttgcttta gcacctacta tatcctaggt gctgtgttag   23760
gcacacatta ttttaagtgg ccattatatt gctacatctc actctggtca ttgccaaggt   23820
aggtagtact ttcttggata gttggttcat gttacttata ggtggtggac ttgttgaggc   23880
aacccccaatg gataatcatc tgagtgtgtt ctctaatctc agattttctc tcatattttt  23940
tggtttgttt tggtttttga tggtggtggt tgtgtgctta ttttgttgc tggcttgttt    24000
```

```
ttttgttttg ttttttgatat ggcaagaatt ggtagtttta tttattaatt gcctaagggt   24060
ctctactttt tttaaaagat gagagtacta aaatagattg ataggtacat atatacccttt   24120 atgggggact gcttatattc cttagagaaa aaaattactt attagcctga caaacaccag   24180
taaaatgtaa atatatccgt gagtaaataa atgaatgtat gctttgtatc tccaaatata   24240
tacatctata ttcttacaaa tatgttttta tgtaatacca atttataaga acttaaaatg   24300
ttggctcaag tgagggatgg tggaaagtag cattatatag ccatttcaac atttgaactt   24360
ttttcttcat tttcttcttt tcttcaggaa tattttttcaa gatgtcttac acagagacac   24420
tctagtgaaa gccttcctgg atcaggtaaa tgttgaactt gagattgtca gagtgaatga   24480
tatgacatgt tttctttttt aatatatctt acaatgcctg ttctctctct ctatatatat   24540
atatttatat atttccctgg atcatgcccc agagttctgc tgagcaattg cagttaagtt   24600
agttacacta cagttctcac aagagtctgt gaggggatgt caggtgcatc attacattgg   24660
atgcctcttg tcctagattt atgtttcggg aattcagacc tatgtttaca atataataaa   24720
tattgttgct gcctttttaca gataaaataa taagatataa acttgaccac aactactgtt   24780
ttttgaaaca tagagttcat ggtttacatg tatcaaagtg aaatctgagt tagcttttac   24840
agatataata tatacatata tatatcctac aatgcttgta ctatatatgt agtacaagta   24900
tatatatgtg tgtgtgtgtg tgtatatata ttatggcact gtagtatata tatgtttata   24960
tgttaaaaaa tatataaata tatgttacat atttaacata aacatatata catatatgtt   25020
aaatatataa catatactct atatatgaca aatagagtat aatatatatt tttattttttt   25080 atatatatat aaaacatgat agaattaaga attaagtcct aatctgtttt attaggtgct   25140
ttttgtagtg ttcagtcttt ctaaagtgtc taaatgattt ttccttttga cttattaatg   25200
gggaagagcc tctatattaa caattaaggc tgcagcattg attacttcaa acaacaaaca   25260
ttttaattca agcattaacc tataactcaa gtaagttttt tttttttttt ttttgagaaa   25320
gggaggttgt ttatttgcct gaattgagtc aaaaatattt ttgaaacatc atgtactcat   25380
ttaaatgata acatctttat tgtttcattc ttttaaaaaa tatctactta attacacagt   25440
tgaaggaaat tgtagattat atggaactta tttcttaata tattacagtt ttgttataat   25500
aacattctgg ggatcaggcc aggaaactgt gtcatagata aagctttgaa ataatgagat   25560
ccttatgttt actagaaatt ttggattgag atctatgtgg tctgtgacat attgcaaagt   25620
tcaaggaaaa ttcgtaggca tggaatttct caaactgaaa atccctccca ctgtccacct   25680
catcacatgc acacattcta ctcttaccca cccactccac cccttgcaaa agtacagata   25740
tatgaatgtc tcaaaaccat gggctcatct tctagaagct tcaatgttat ttgaagattt   25800
gggcagagga agttaagaaa tatgaaatag cttacatatg agtttttaata gtgaaacaaa   25860 catggatgta ttctgaagta gaatgcaaaa tttgagtgca tttttttttt tttgagactg   25920
agtctggctc tgtcgcccag gctggagtgc agtggccgga tctcagctca ctgcaagctc   25980
cacctcccgg gtttacgcca ttctcctgcc tcagcctccc gagtagctgg gaccacaggc   26040
gcccgccact tcgcccggct agtttgtttg tatttttttag tagagatggg gtttcaccgt   26100
gttagccagg gannnnnnnn nnnnnnnnnn nnnnnnnnnn nnnnnnnnnn nnnnnccatt   26160
gagtgcattt ttaaagataa atcagaaaac ttcgaaaaac tatcagattg gccggacatg   26220
gtggcttatg cctgtaatcc tagcactttg ggaggctgag gtgggtggat cacgaggtca   26280
ggagatcgag accatcctgc caacatggtg aaaccccatc tctactaagt atacaaaaat   26340
tagctgggcg tgacagcacg tgcctgtaat cccagcactc tgggaggctg aggcaggaga   26400
```

```
atcgcttgaa cccgggaggt ggaggttgca gtgagtcaag atcacaccac tgcacttcag   26460
cttggtgaca gagctagact ccatatcaaa aaaaaaaaaa aaaaaaagaa gtcagattgt   26520
tcctacaccc agtgcttcta taccacactc ctactagggg gcatcagtgg aaatggttaa   26580
ggagatgttt agtgtgtatt gtctgccaag cactgttaac actgtcctag aaacattgct   26640
gtacaagtag aatgtgagca aattatgtat tgaaatggtt cctctccctg caggtctttc   26700
agctgaaacc tggcttatct ctcaggagta ctttccttgc acagttttta cttgtccttc   26760
acagaaaagc cttgacacta ataaaatata tagaagatga tacgtgagta caactcctac   26820
atggaggaaa aaccttttgt acgttgtttt ttgtttatt cctttgtac attttctgta    26880 tcataatttt tgctttttt ttttttttt tttctccat tactttcagg cagaagggaa    26940 aaaagcccctt taaatctctt cggaacctga agatagacct tgatttaaca gcagagggcg   27000
atcttaacat aataatggct ctggctgaga aaattaaacc aggcctacac tcttttatct   27060
ttggaagacc tttctacact agtgtacaag aacgagatgt tctaatgact tttaaatgt    27120 gtaacttaat aagcctattc catcacaatc gtgatcgctg ctaaagtagc tcggtggtgt   27180
ggggaaacat tcccctggat catactccag agctctgctc ggcagttgca gttaagttag   27240
ttacactaca gttctcacaa gagtctgtga ggggatgtca ggtgcatcat tacattggat   27300
gtctcttttc ctagatttat gcttttggga tacagaccta tgtttacaat ataataggta   27360
ttattgctgt cttttaaata tataataata ggatataaac ttgaccacaa ctgctgtttt   27420
tttgaaatat atgattcatg gtttacatgt attaaggtga aatccgagtt cgcttttaca   27480
gatattagtt gactttctat cttttggcat tctttggtgt gtggaattac tgtaatactt   27540
ctgcaatcaa ctgaaaatta gagcctttaa atgatttcag ttccacagaa agaaagtgag   27600
cttcaacata ggataagctt tagaaagaga attgatcaag cagatgttta attggaattg   27660
attattagat cctgctttgt ggatttagcc ctcgggattc agtctgtaga aatgtctgat   27720
agttctctat agtccctgct catggtgaac cacagttagg atgttttgtt tgttttattg   27780
ttgttgctat tgttgatgtt ctatatagtt gagctctata aaaggaaatt gtattttatg   27840
ttttagtagt tgttgccaac tttttaaatt aattttcatt attttttgagc caaattgaaa   27900 tgtgcacctc ctgtgccttt ttttttccttg gaaaatcgaa ttacttggaa gaagttcaga   27960
tttcactggt cagtcgtttt catcttgttt tcttcttgca gagtcttacc atgtacctgc   28020
tttggcaatc attgtaactc tgagattata aaatgcatta gagaatatat taactaataa   28080
gatctttttt ttcaggaaca gaaaatagtt ccttgagtac ttccttctta catttctgcc   28140 catgttttg aagttgttgc catttgcctg caataggcta taaggaatag caggagaaat    28200
tttactgaag tgctatttt ctaggtgcta ctttggcaga gctaagtggt ctgtttcttt    28260
tgtttcctta atgcgtttgg accattttgc tggctgtaaa ataactgatt aatataattc   28320
taacacaata ttgacattgt agtgtacaca aacacaaata ttttatttaa aactggaagt   28380
aacataaaag ggaaaatata tttataagaa aggaataaag gtaatagagc tcttctgtcc   28440
cccagccacc aaatttacac aacaaaatca tatgttctaa tgtgaaaggt cataatagct   28500
ttcccatcat taatcagaaa gatgtggcag cttgattttt tagacaaccc ctgaactaga   28560
tgactgttgt actgtagctc agtcatttaa aaaatatata aatactatct cgtagtgtcc   28620
catactatgt ttttacatg atagattctt atttaagtgc taactggtta ttttcttttgg   28680 ctggtttatt gtactgttat atagaatgta agttgtacag tgaaataagt tattaaagca   28740
```

-continued

```
tgtgtaaaca ttgttatata tcttttctcc tagatggaga attttgaata aaatatnnnn    28800
nnnnnnnnnn nnnnnnnnnn nnnnnnnnnn nnnnnnnnnn nnnnnnnnnn nnnnnnnnnn    28860
nnnnnnnnnn nnnnnnnnnn nnnnnnnnnn nnnnnnnnnn nnnnnnnnnn nnnnnnnnnn    28920
nnnnnnnnnn nnnnnnnnnn nnnnnnnnnn nnnnnnnnnn nnnnnnnnnn nnnnnnnnnn    28980
nnnnnnnnnn nnnnnnnnnn nnnnnnnnnn nnnnnnnnnn nnnnnnnnnn nnnnnnnnnn    29040
nnnnnnnnnn nnnnnnnnnn nnnnnnnnnn nnnnnnnnnn nnnnnnnnnn nnnnnnnnnn    29100
nnnnnnnnnn nnnnnnnnnn nnnnnnnnnn nnnnnnnnnn nnnnnnnnnn nnnnnnnnnn    29160
nnnnnnnnnn nnnnnnnnnn nnnnnnagaa gactaattga tcatatcact atgattctca    29220
aagaagaacc aaaacttcat ataatactac aaatatgaga tagttacttc tgtagtatat    29280
ttctgtaatg ctacaggtta aacaggtcac tcttatataa cactattttg attttgatgt    29340
agaattgcac aaattgatat ttcttctatg atctgtaggg tatagcttaa agtagcaaaa    29400
acagtccacc acctccagtt aacacacagt aacactatgg gactagtatt attatttcca    29460
ttttacaaag gaggaaacta aagcttaaag atgtgtaata tacagcccaa ggtcacacag    29520
ctggtaaagg tagatttcat cccagacagt tacagtcatt gccgtgggca cagctcctaa    29580
cttattaact ccatgtaact ggtactcagt ttagttgaat tgaaaggaga gtagggaagc    29640
aggtctgttt gcactattca gagcccaagt gtgaatccct gctgtgctgc ttggagaagt    29700
tacttaacct atgcaaggtt cattttttaa atatttgaaa cggaatgata atacatactc    29760
caccagtggg tttaatgaga ccttataaga tcgttagttc agtacctgac cagtgcttca    29820
taaatgcttt ttcatccaat ctgacaatct ctagcttgta attggggcat ttagaacatt    29880
taatatgatt attggcatgg taggttaaag ttgtcatctt gctgttttct ctttgttctt    29940
ttttctcctt tcttttggat ttttttttaa ttttactgtg tcttctctgt tgtcttatta    30000
a                                                                    30001
```

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
gggtctagca agagcaggtg                                                 20

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
gtcttggcaa cagctggaga t                                               21

<210> SEQ ID NO 14
<211> LENGTH: 24
<212> TYPE: DNA
<213> ORGANISM: Artificial sequence
<220> FEATURE:
<223> OTHER INFORMATION: Probe

<400> SEQUENCE: 14
tgatgtcgac tctttgccca ccgc                                            24

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
tgtgacagtt ggaatgcagt ga                                            22

<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
gccacttaaa gcaatctctg tcttg                                         25

<210> SEQ ID NO 17
<211> LENGTH: 21
<212> TYPE: DNA
<213> ORGANISM: Artificial sequence
<220> FEATURE:
<223> OTHER INFORMATION: Probe

<400> SEQUENCE: 17
tcgactcttt gcccaccgcc a                                             21

<210> SEQ ID NO 18
<211> LENGTH: 783
<212> TYPE: DNA
<213> ORGANISM: Homo sapiens

<400> SEQUENCE: 18
gcctctcagt acccgaggct cccttttctc gagcccgcag cggcagcgct cccagcgggt    60
ccccgggaag gagacagctc gggtactgag ggcgggaaag caaggaagag gccagatccc   120
catcccttgt ccctgcgccg ccgccgccgc cgccgccgcc gggaagcccg ggccccggat   180
gcaggcaatt ccaccagtcg ctagaggcga aagcccgaca cccagcttcg gtcagagaaa   240
tgagagggaa agtaaaaatg cgtcgagctc tgaggagagc ccccgcttct acccgcgcct   300
cttcccggca gccgaacccc aaacagccac ccgccaggat gccgcctcct cactcaccca   360
ctcgccaccg cctgcgcctc cgccgccgcg ggcgcaggca ccgcaaccgc agccccgccc   420
cgggcccgcc cccgggcccg ccccgaccac gccccggccc cggccccggc cccggccccg   480
gcccctagcg cgcgactcct gagttccaga gcttgctaca ggctgcggtt gtttccctcc   540
ttgttttctt ctggttaatc tttatcaggt cttttcttgt tcaccctcag cgagtactgt   600
gagagcaagt agtggggaga gagggtggga aaaacaaaaa cacacacctc ctaaacccac   660
acctgctctt gctagacccc gccccaaaaa gagaagcaac cgggcagcag ggacggctga   720
cacaccaagc gtcatctttt acgtgggcgg aacttgtcgc tgtttgacgc acctctcttt   780
cct                                                                783

<210> SEQ ID NO 19

<400> SEQUENCE: 19

000

<210> SEQ ID NO 20

<400> SEQUENCE: 20

000

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
gccttactct aggaccaaga                                               20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ccggccccta gcgcgcgact                                               20

<210> SEQ ID NO 23
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 23
cggcccctag cgcgcgact                                                19

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24
ccggccccta gcgcgcgac                                                19

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ccctagcgcg cgactcctga                                               20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
cccctagcgc gcgactcctg                                               20

```
<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
gcccctagcg cgcgactcct                                                    20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
ggcccctagc gcgcgactcc                                                    20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
cggcccctag cgcgcgactc                                                    20

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
cctagcgcgc gactcctg                                                      18

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 31
ccctagcgcg cgactcct                                                      18

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
cccctagcgc gcgactcc                                                      18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 33 gccectagcg cgcgactc                                                       18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
ggcccctagc gcgcgact                                                       18

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
cggcccctag cgcgcgac                                                       18

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
aggctgcggt tgtttccctc                                                     20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
caggctgcgg ttgtttccct                                                     20

<210> SEQ ID NO 38
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 38
ggctgcggtt gtttccctc                                                      19

<210> SEQ ID NO 39
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 39
aggctgcggt tgtttccct                                                      19

<210> SEQ ID NO 40
<211> LENGTH: 19

<212> TYPE: DNA
<213> ORGANISM: Artificial sequence
<220> FEATURE:
<223> OTHER INFORMATION: Synthetic oligonucleotide

<400> SEQUENCE: 40
caggctgcgg ttgtttccc                                            19

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 41
gctgcggttg tttccctc                                             18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
ggctgcggtt gtttccct                                             18

<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
aggctgcggt tgtttccc                                             18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 44
caggctgcgg ttgtttcc                                             18

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tctgtctttg gagcccaaat                                           20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46

```
ctgcgatccc cattccagtt                                              20

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
gccttactct aggaccaa                                                18

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
tctgtctttg gagcccaa                                                18

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggttaatctt tatcaggtct                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tggttaatct ttatcaggtc                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ctggttaatc tttatcaggt                                              20

<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 52
gttaatcttt atcaggtc                                                18

<210> SEQ ID NO 53
<211> LENGTH: 18
<212> TYPE: DNA
<213> ORGANISM: Artificial sequence
```

```
<220> FEATURE:
<223> OTHER INFORMATION: Synthetic oligonucleotide

<400> SEQUENCE: 53
ggttaatctt tatcaggt                                                 18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
tggttaatct ttatcagg                                                 18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55
ctagcgcgcg actcctga                                                 18

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
gggacactac aaggtagtat                                               20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
tacaggctgc ggttgtttcc                                               20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
cccggcccct agcgcgcgac                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
ggtaacttca aactcttggg                                               20
```

```
<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide
<400> SEQUENCE: 60
aatctttatc aggtcttttc                                              20
```